United States Patent
Cooper et al.

(10) Patent No.: US 11,866,499 B2
(45) Date of Patent: Jan. 9, 2024

(54) MONOSPECIFIC AND MULTISPECIFIC ANTI-TMEFF2 ANTIBODIES AND THEIR USES

(71) Applicant: Janssen Biotech, Inc., Horsham, PA (US)

(72) Inventors: Philip Cooper, Philadelphia, PA (US); Robin Ernst, Kintnersville, PA (US); Rajkumar Ganesan, Blue Bell, PA (US); Colleen Kane, Flourtown, PA (US); Michael Russell, West Chester, PA (US); Sanjaya Singh, Blue Bell, PA (US); Sathyadevi Venkataramani, Blue Bell, PA (US); Sheng-Jiun Wu, Broomall, PA (US)

(73) Assignee: Janssen Biotech, Inc., Horsham, PA (US)

( * ) Notice: Subject to any disclaimer, the term of this patent is extended or adjusted under 35 U.S.C. 154(b) by 284 days.

(21) Appl. No.: 16/417,889

(22) Filed: May 21, 2019

(65) Prior Publication Data
US 2019/0359711 A1    Nov. 28, 2019

Related U.S. Application Data

(60) Provisional application No. 62/675,957, filed on May 24, 2018.

(51) Int. Cl.
C07K 16/28 (2006.01)
A61P 35/00 (2006.01)
A61K 45/06 (2006.01)

(52) U.S. Cl.
CPC .......... *C07K 16/2809* (2013.01); *A61P 35/00* (2018.01); *A61K 45/06* (2013.01)

(58) Field of Classification Search
CPC ...... C07K 16/2809; A61K 45/06; A61P 35/00
See application file for complete search history.

(56) References Cited

U.S. PATENT DOCUMENTS

| | | |
|---|---|---|
| 4,683,195 A | 7/1987 | Mullis et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,571,698 A | 11/1996 | Ladner et al. |
| 5,580,717 A | 12/1996 | Dower et al. |
| 5,885,793 A | 3/1999 | Griffiths et al. |
| 5,969,108 A | 10/1999 | McCafferty et al. |
| 6,150,584 A | 11/2000 | Kucherlapati et al. |
| 6,172,197 B1 | 1/2001 | McCafferty et al. |
| 6,180,370 B1 | 1/2001 | Queen et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,818,749 B1 | 11/2004 | Kashmiri et al. |
| 7,709,226 B2 | 5/2010 | Foote |
| 8,242,247 B2 | 8/2012 | Klein et al. |
| 8,748,356 B2 | 6/2014 | Raghunathan |
| 9,850,310 B2 | 12/2017 | Gaudet et al. |
| 2007/0014796 A1 | 1/2007 | Carr et al. |
| 2007/0287170 A1 | 12/2007 | Davis et al. |
| 2009/0182127 A1 | 7/2009 | Kjaergaard et al. |
| 2010/0015133 A1 | 1/2010 | Igawa et al. |
| 2010/0028637 A1 | 2/2010 | Tavsanli et al. |
| 2010/0261620 A1 | 10/2010 | Almagro et al. |
| 2011/0123532 A1 | 5/2011 | Gurney et al. |
| 2012/0149876 A1 | 6/2012 | Spreter Von Kreudenstein et al. |
| 2013/0195849 A1 | 8/2013 | Spreter Von Kreudenstein et al. |
| 2014/0273092 A1 | 9/2014 | Flikweert et al. |
| 2015/0030602 A1 | 1/2015 | Sillaber et al. |
| 2019/0352421 A1* | 11/2019 | Adams ................... C07K 16/30 |

FOREIGN PATENT DOCUMENTS

| | | |
|---|---|---|
| JP | 2006-502092 | 1/2006 |
| WO | WO 1988/01649 A1 | 3/1988 |
| WO | WO 1990/04036 A1 | 4/1990 |
| WO | WO 1990/007861 A1 | 7/1990 |
| WO | WO 1992/01047 A1 | 1/1992 |
| WO | WO 1992/22653 A1 | 12/1992 |
| WO | WO 1994/13804 A1 | 6/1994 |
| WO | WO 1998/44001 A1 | 10/1998 |
| WO | WO 1999/45962 A1 | 9/1999 |
| WO | WO 2002/043478 A1 | 6/2002 |
| WO | WO 2002/066630 A1 | 8/2002 |
| WO | WO 2003/075855 | 9/2003 |
| WO | WO 2007/027713 | 3/2007 |
| WO | WO 2009/018386 A1 | 2/2009 |

(Continued)

OTHER PUBLICATIONS

Chelius et al., Formation of Pyroglutamic Acid from N-Terminal Glutamic Acid in Immunoglobulin Gamma Antibodies, Anal. Chem. 2006, 78, 2370-2376, Publication Date: Feb. 24, 2006 (Year: 2006).*
Labrijn et al., Efficient generation of stable bispecific IgG1 by controlled Fab-arm exchange, PNAS, 110 (13); 5145-5150 and Supporting Information; Publication Date: Mar. 26, 2013 (Year: 2013).*
Almagro & Fransson, Humanization of antibodies, Frontiers in Bioscience 2008; 13: 1619-33 (Year: 2008).*
Sela-Culang et al., The structural basis of antibody-antigen recognition, Frontiers in immunology 4 (2013): 302 (Year: 2013).*

(Continued)

*Primary Examiner* — Peter J Reddig
*Assistant Examiner* — Cheng Lu
(74) *Attorney, Agent, or Firm* — J. Jason Galvez

(57) ABSTRACT

The disclosure provided herein relates to monospecific and multispecific anti-TMEFF2 antibodies, and methods of producing and using the described antibodies.

23 Claims, 10 Drawing Sheets
Specification includes a Sequence Listing.

(56) References Cited

FOREIGN PATENT DOCUMENTS

| WO | WO 2009/052249 | | 4/2009 |
|---|---|---|---|
| WO | WO 2009/080251 | A1 | 7/2009 |
| WO | WO 2009/080252 | A1 | 7/2009 |
| WO | WO 2009/080254 | A1 | 7/2009 |
| WO | WO 2009/085462 | A1 | 7/2009 |
| WO | WO 2011/131746 | A2 | 10/2011 |
| WO | WO 2013/093122 | A2 | 6/2013 |
| WO | WO 2014/093908 | A2 | 6/2014 |
| WO | WO 2006/028936 | A2 | 3/2016 |
| WO | WO 2016/179003 | | 11/2016 |
| WO | WO 2016/204966 | | 12/2016 |
| WO | WO 2019/224717 | | 11/2019 |

OTHER PUBLICATIONS

Lin et al., "TMEFF2 Is a PDGF-AA Binding Protein with Methylation-Associated Gene Silencing in Multiple Cancer Types Including Glioma.", PLoS ONE, Apr. 2011, pp. 1-14, e18608, vol. 6(4).

Penning et al., "Induction of Apoptosis in Hematopoietic Cells with an Antibody Against Tomoregulin-1.", Anticancer Research, 2006, pp. 339-346, vol. 26.

Bargou et al., "Tumor Regression in Cancer Patients by Very Low Doses of a T Cell-Engaging Antibody.", Science, Aug. 15, 2008, pp. 974-977, vol. 321.

International Search Report of the International Searching Authority relating to corresponding International Patent Application No. PCT/IB2019/054184, filed May 21, 2019, dated Dec. 2, 2019.

Written Opinion of the International Searching Authority relating to corresponding International Patent Application No. PCT/IB2019/054184, filed May 21, 2019, dated Dec. 2, 2019.

Afar et al., "Preclinical validation of anti-TMEFF2-auristatin E-conjugated antibodies in the treatment of prostate cancer", (2004) Molecular Cancer Therapeutics, vol. 3 (8); 921.

Baert et al., "Influence of Immunogenicity on the Long-Term Efficacy of Infliximab in Crohn's Disease" (2003) New England Journal of Medicine, vol. 348:601-08.

Bedu-Addo et al., "Use of Biophysical Characterization in Preformulation Development of a Heavy-Chain Fragment of Botulinum Serotype B: Evaluation of Suitable Purification Process Conditions", (2004) Pharmaceutical Research, vol. 21, No. 8:1353-61.

Brüggemann and Taussig, "Production of human antibody repertoires in transgenic mice", (1997) Curr Opin Biotechnol, vol. 8:455-458.

Brüggemann et al., "Human antibody production in transgenic mice: expression from 100 kb of the human IgH locus", (1991) Eur. Journal of Immunology, vol. 21:1323-1326.

Cai et al., "C-Terminal Lysine Processing of Human Immunoglobulin G2 Heavy Chain In Vivo" (2011) Biotechnology and Bioenginerring vol. 108:404-412.

Chothia et al., "Canonical Structures for the Hypervariable Regions of Immunoglobulins", (1987), J Mol Biol vol. 196: 901-17.

E. Meyers and W. Miller, "Optimal alignments in linear space", (1988), Computer Appl Biosci vol. 4 No. 1:11-17.

Fishwild et al., "High-avidity human IgGκ monoclonal antibodies from a novel strain of minilocus transgenic mice", (1996) Nature Biotechnology vol. 14:845-851.

Gadi et al., "In vivo sensitization of ovarian tumors to chemotherapy by expression of E. coli purine nucleoside phosphorylase in a small fraction of cells", (2000) Gene Therapy. vol. 1738-1743.

Gery et al., "TMEFF2 is an androgen-regulated gene exhibiting antiproliferative effects in prostate cancer cells", (2002) Oncogene, vol. 21:4739-4746.

Glynne-Jones et al., "TENB2, A Proteoglycan Identified In Prostate Cancer That Is Associated with Disease Progression and Androgen Independence", (2001) International Journal of Cancer, vol. 94:178-184.

Goding, Monoclonal Antibodies: Principles and Practice, pp. 59-103 (Academic Press, 1986).

Green & Jakobovits, "Regulation of B Cell Development by Variable Gene Complexity in Mice Reconstituted with Human Immunoglobulin Yeast Artificial Chromosomes", (1998) Journal Exp. Med., vol. 188:483-95.

Green et al., "Antigen-specific human monoclonal antibodies from mice engineered with human Ig heavy and light chain YACs", (1994) Nature Genetics, vol. 7:13-21.

Green, Larry, "Antibody engineering via genetic engineering of the mouse: XenoMouse strains are a vehicle for the facile generation of therapeutic human monoclonal antibodies", (1999) Journal of Immunological Methods, vol. 231:11-23.

Gupta et al., "Development of a Multidose Formulation for a Humanized Monoclonal Antibody Using Experimental Design Techniques.", AAPS PharmSci,, 2003, pp. 1-9, 5E8.

Honegger and Pluckthun, "Yet Another Numbering Scheme for Immunoglobulin Variable Domains: An Automatic Modeling and Analysis Tool", (2001) J Mol Biol, vol. 309:657-70.

Hoogenboom and Winter, "By-passing Immunization Antibodies from Synthetic Repertoires of Germline VH Gene Segments Rearranged in Vitro", (1992) Journal of Molecular Biology, vol. 227:381-388.

Horie et al., "Identification and Characterization of TMEFF2, a Novel Survival Factor for Hippocampal and Mescencephalic Neurons", (2000) Genomics, vol. 67, 146-152.

Knappik et al., "Fully Synthetic Human Combinatorial Antibody Libraries *HuCAL) Based on Modular Consensus Frameworks and CDRs Randomized with Trinucleotides", (2000) J Mol Biol vol. 296:57-86.

Kohler and Milstein, "Continuous cultures of fused cells secreting antibody of predefined specificity", (1975) Nature, vol. 256:λ-497.

Krebs et al., "High-throughput generation and engineering of recombinant human antibodies", (2001) Journal of Immunological Methods, vol. 254:67-84.

Lefranc et al., "IMGT unique numbering for immunoglobulin and T cell receptor variable domains and Ig superfamily V-like domains.", Development and Comparative Immunology, 27 (2003), 55-77.

Liang et al., "The Gene for a Novel Transmembrane Protein Containing Epidermal Growth Factor and Follistatin Domains Is Frequently Hypermethylated in Human Tumor Cells", (2000) Cancer Research, vol. 60;4907-4912.

Lonberg and Huszar, "Human Antibodies from Transgenic Mice" (1995) International Reviews of Immunology vol. 13:65-93.

Lonberg et al., "Antigen-specific human antibodies from mice comprising four distinct genetic modifications", (1994) Nature vol. 368:856-9.

Maa et al., "Aggregation of recombinant human growth hormone induced by phenolic compounds", (1996) International Journal of Pharmaceutics, vol. 140:155-68.

MacLennan et al., "Structure-Function Relationship in the $Ca^{2+}$-Binding and Translocation Domain of SERCA1: physiological correlates in Brody disease", (1988) Acta Physiol Scand Suppl vol. 643:55-67.

Marks et al., "By-passing Immunization Human Antibodies from V-gene Libraries Displayed on Phage", (1991) Journal of Molecular Biology, vol. 222:581.

Martin and Thornton, Structural Families in Loops of Homologous Proteins: Automatic Classification, Modelling and Application to Antibodies (1996) Journal Molecular Biology, vol. 263: 800-15.

Mendez et al., "Functional transplant of megabase human immunoglobulin loci recapitulates human antibody response in mice" (1997) Nature Genetics, vol. 15:146-156.

Needleman and Wunsch "A General Method Applicable to the Search for Similarities in the Amino Acid Sequence of Two Proteins", (1970) Journal of Molecular Biology vol. 48:444-453.

Okayama and Berg, "A cDNA Cloning Vector That Permits Expression of cDNA Inserts in Mammalian Cells", (1983) Molecular and Cellular Biology, vol. 3, No. 2:280-289.

Osborn, et al., "High-Affinity IgG Antibodies Develop Naturally in I-g-Knockout Rats Carrying Germline Human IgH/Igκ/Igλ Loci Bearing the Rat CH Region", (2013) Journal of Immunology; vol. 190(4): 1481-1490.

Padlan, Eduardo, "A Possible Procedure for Reducing the Immunogenicity of Antibody Variable Domains While Preserving Their Ligand-Binding Properties", (1991) Molecular Immunology, vol. 28, No. 4/5:489-499.

(56) References Cited

OTHER PUBLICATIONS

Pascal et al., "HDX Workbench: Software for the Analysis of H/D Exchange MS Data", (2012), Journal of American Society Mass Spectrom, vol. 23 (9), 1512-1521.

Remmele et al., "Differential Scanning Calorimetry; A Practical Tool for Elucidating Stability of Liquid Biopharmaceuticals", (2000) Biopharm, vol. 13:36-46.

Remmele et al., "Interleukin-1 Receptor (IL-1R) Liquid Formulation Development Using Differential Scanning Calorimetry", (1998) Pharmaceutical Research, vol. 15, No. 2:200-8.

Sasaki et al., "Structure-Mutation Analysis of the ATPase Site of Dictyostelium Discoideum Myosin II", (1988) Adv Biophys, vol. 35:1-24.

Sheets et al., "Efficient construction of a large nonimmune phage antibody library: The production of high-affinity human single-chain antibodies to protein antigens", (1998) PITAS (USA) 95:6157-6162.

Shi et al., "De Novo Selection of High-Affinity Antibodies from Synthetic Fab Libraries Displayed on Phage as pIX Fusion Proteins", (2010) Journal of Molecular Biology, vol. 397:385-96.

Stickler et al., "The human G1m1 allotype associates with CD4+ T-cell responsiveness to a highly conserved IgG1 constant region peptide and confers an asparaginyl endopeptidase cleavage site", (2011) Genes and Immunity vol. 12:213-21.

Vaughan et al., "Human Antibodies with Sub-nanomolar Affinities Isolated from a Large Non-immunized Phage Display Library", (1996) Nature Biotechnology, vol. 14:309-314.

Wörn et al., "Stability Engineering of Antibody Single-chain Fv Fragments", (2001), Journal of Molecular Biology, vol. 305:989-1010.

Wu et al., "An analysis of the sequences o the variable regions of bence jones proteins and myeloma light chains and their implications for anti-body complementarity", (1970), Journal Exp. Med., vol. 132:211-50.

Yang et al., "Eradication of Established Tumors by a Fully Human Monoclonal Antibody to the Epidermal Growth Factor Receptor without Concomitant Chemotherapy", (1999) Cancer Research vol. 59:1236-1243.

Zhang et al., "Mechanism for Benzyl Alcohol-Induced Aggregation of Recombinant Human Interleukin-1 receptor Antagonist in Aqueous Solution", (2004) Journal of Pharmaceutical Science, vol. 93:3076-89.

* cited by examiner

FIG. 1

| | |
|---|---|
| 25 | EVQLLESGGGLVQR-GGSLRPSCAASGFTFS |
| 27 | EVQLLESGGGLVQPPGGSLRLSCAASGFTFS |
| 87 | EVQLLESGGGLVQP-GGSLRLSCAASGFTFS |
| 89 | EVQLLESGGGLVQP-GGSLRLSCAASGFTFS |
| | \*\*\*\*\*\*\*\*\*\*\*\*  \*\*\*\*\* \*\*\*\*\*\*\*\*\* |

| | |
|---|---|
| 25 | SYSMSWVRQAPGKGLEWVSVISGSGGFTDY |
| 27 | SYSMSWVRQAPGKGLEWVSVISGGGSFTSY |
| 87 | SYSMSWVRQAPGKGLEWVSVISGSGGFTDY |
| 89 | SYSMSWVRQAPGKGLEWVSVISGSGGFTDY |
| | \*\*\*\*\*\*\*\*\*\*\*\*\*\*\*\*\*\*\*\*\*.\*.\*\*.\* |

| | |
|---|---|
| 25 | ADSVKGRFTISRDNSKNTLYLHMNSLRAED |
| 27 | ADSVKGRFTISRDNSNNTLYLQMSSLRAED |
| 87 | ADSVKGRFTISRDNSKNTLYLQMNSLRAED |
| 89 | ADSVKGRFTISRDNSKNTLYLHMNSLRAED |
| | \*\*\*\*\*\*\*\*\*\*\*\*\*\*\*:\*\*\*\*\*:\*.\*\*\*\*\*\* |

| | |
|---|---|
| 25 | TAVYYCARMPLNSPHDYWGQGTLVTVSS |
| 27 | TAFYYCARMPLNSPHDCWGQGTLVTVSS |
| 87 | TAVYYCARMPLNSPHDYWGQGTLVTVSS |
| 89 | TAVYYCARMPLNSPHDYWGQGTLVTVSS |
| | \*\*.\*\*\*\*\*\*\*\*\*\*\*\*\*\* \*\*\*\*\*\*\*\*\*\* |

FIG. 2

| | |
|---|---|
| 28 | AIQMTQSPSSLSASVGDRVTITCRASQGIR |
| 30 | AIQMTQSPSSLSASVGDRVTITCRASQGIR |
| 88 | DIQMTQSPSSLSASVGDRVTITCRASQGIR |
| 90 | AIQMTQSPSSLSASVGDRVTITCRASQGIR |
| | ****************************** |

| | |
|---|---|
| 28 | NDLGWYQQKPGKAPKLLIYAASSLQSGVPS |
| 30 | NDLGWYQQKPGKAPKLLIYAASSLQSGVPS |
| 88 | NDLGWYQQKPGKAPKLLIYAASSLQSGVPS |
| 90 | NDLGWYQQKPGKAPKLLIYAASSLQSGVPS |
| | ****************************** |

| | |
|---|---|
| 28 | RFSGSGSGTDFTLTISSLQPEDFATYYCLQ |
| 30 | RFSGSGSGTDFTLTISSLQPEDFATYYCLQ |
| 88 | RFSGSGSGTDFTLTISSLQPEDFATYYCLQ |
| 90 | RFSGSGSGTDFTLTISSLQPEDFATYYCLQ |
| | ****************************** |

| | |
|---|---|
| 28 | DYNYALTFGGGTKVEIK |
| 30 | DYNYSLTFGGGTKVEIR |
| 88 | DYNYPLTFGGGTKVEIK |
| 90 | DYNYPLTFGGGTKVEIK |
| | **.*********: |

*p≤ 0.0001 for treatment vs. control, calculated by the Linear Mixed-Effects analysis followed by pairwise comparisons. Bar below the X-axis represents the dosing period.

MONOSPECIFIC AND MULTISPECIFIC ANTI-TMEFF2 ANTIBODIES AND THEIR USES

SEQUENCE LISTING

The instant application contains a Sequence Listing which has been submitted electronically in ASCII format and is hereby incorporated by reference in its entirety. Said ASCII copy, created on Jan. 31, 2019, is named JBI5160WOPCT1_SL.txt and is 144,156 bytes in size.

TECHNICAL FIELD

The disclosure provided herein relates to monospecific and multispecific anti-TMEFF2 antibodies, and methods of producing and using the described antibodies.

BACKGROUND

Prostate cancer is the second most common cancer in men worldwide, and the sixth leading cause of cancer-related death. Globally, there are approximately 1,100,000 new cases and 300,000 mortalities every year, comprising 4 percent of all cancer deaths. It is estimated that 1 in every 6 men will be diagnosed with the disease during his lifetime. Prostate cancer risk strongly correlates with age: around three-quarters of cases occur in men over 65 years old with the largest number of cases in those aged 70-74. It is estimated from post-mortem data that around a half of men in their fifties and 80% of men aged 80 have histological evidence of cancer in the prostate. At the early stages, the 5-year survival rate nears 100%. When the cancer has metastasized, however, the 5-year survival rate drops to 28%, and there remains a need for effective treatments for advanced-stage prostate cancer.

Testicular androgen deprivation therapy usually results in stabilization or regression of the disease (in 80% of patients). Current treatments for prostate cancer include surgery, radiation and hormone therapies. Typically, the cancer vaccine sipuleucel-T, a radiopharmaceutical agent (such as radium-223 chloride), secondary hormone therapies (such as abiraterone or enzalutamide), and/or chemotherapies (docetaxel and cabazitaxel) are added to the hormonal therapy in sequence. While each of these treatments can delay growth of the cancer for several months and palliate symptoms produced by the disease, progression of metastatic prostate cancer eventually develops. When prostate cancers grow despite the lowering of testosterone levels by hormone therapy, treatment options are limited.

Therefore, there is a need to develop additional therapeutics to treat prostate cancer.

SUMMARY OF THE INVENTION

The invention provides an isolated anti-TMEFF2 antibody or an antigen binding fragment thereof that binds to a membrane proximal region of SEQ ID NO: 110 of TMEFF2.

The invention also provides an isolated anti-TMEFF2 antibody or an antigen binding fragment thereof that binds to the membrane proximal region of TMEFF2, wherein the antibody or the antigen binding fragment thereof competes for binding to the membrane proximal region of TMEFF2 with a reference antibody comprising a heavy chain variable region (VH) of SEQ ID NO: 25 and a light chain variable region (VL) of SEQ ID NO: 28, the VH of SEQ ID NO: 26 and the VL of SEQ ID NO: 29, the VH of SEQ ID NO: 27 and the VL of SEQ ID NO: 30, the VH of SEQ ID NO: 26 and the VL of SEQ ID NO: 31, the VH of SEQ ID NO: 87 and the VL of SEQ ID NO: 88, or the VH of SEQ ID NO: 89 and the VL of SEQ ID NO: 90.

The invention also provides an isolated anti-TMEFF2 antibody or an antigen binding fragment thereof that binds to a membrane proximal region of TMEFF2, wherein the antibody or the antigen binding fragment thereof binds within residues HGKCEHSINMQEPSC (SEQ ID NO: 57) or DAGYTGQHCEKKDYSVL (SEQ ID NO: 58) to the membrane proximal region of TMEFF2.

The invention also provides an isolated anti-TMEFF2 antibody having certain heavy chain and light chain complementarity determining region sequences as described herein.

The invention also provides an isolated anti-TMEFF2 antibody having certain heavy chain variable region and light chain variable region sequences as described herein.

The invention also provides an isolated anti-TMEFF2 antibody having certain heavy chain and light chain sequences as described herein.

The invention also provides an isolated anti-TMEFF2 antibody or an antigen-binding fragment thereof, comprising
a HCDR1, a HCDR2, a HCDR3, a LCDR1, a LCDR2 and a LCDR3 of SEQ ID NOs: 10, 12, 15, 18, 20 and 22, respectively;
a VH of SEQ ID NO: 25 and a VL of SEQ ID NO: 28; and/or
a HC of SEQ ID NO: 32 and a LC of SEQ ID NO: 35.

The invention also provides an isolated anti-TMEFF2 antibody or an antigen-binding fragment thereof, comprising
a HCDR1, a HCDR2, a HCDR3, a LCDR1, a LCDR2 and a LCDR3 of SEQ ID NOs: 11, 13, 16, 19, 21 and 23, respectively;
a VH of SEQ ID NO: 26 and a VL of SEQ ID NO: 29; and/or
a HC of SEQ ID NO: 33 and a LC of SEQ ID NO: 36.

The invention also provides an isolated anti-TMEFF2 antibody or an antigen-binding fragment thereof, comprising
a HCDR1, a HCDR2, a HCDR3, a LCDR1, a LCDR2 and a LCDR3 of SEQ ID NOs: 10, 14, 17, 18, 20 and 24, respectively;
a VH of SEQ ID NO: 27 and a VL of SEQ ID NO: 30; and/or
a HC of SEQ ID NO: 34 and a LC of SEQ ID NO: 37.

The invention also provides an isolated anti-TMEFF2 antibody or an antigen-binding fragment thereof, comprising
a HCDR1, a HCDR2, a HCDR3, a LCDR1, a LCDR2 and a LCDR3 of SEQ ID NOs: 11, 13, 16, 18, 20 and 22, respectively;
a VH of SEQ ID NO: 26 and a VL of SEQ ID NO: 31; and/or
a HC of SEQ ID NO: 33 and a LC of SEQ ID NO: 38.

The invention also provides an isolated anti-TMEFF2 antibody or an antigen-binding fragment thereof, comprising
a HCDR1, a HCDR2, a HCDR3, a LCDR1, a LCDR2 and a LCDR3 of SEQ ID NOs: 10, 12, 15, 18, 20 and 86, respectively;
a VH of SEQ ID NO: 87 and a VL of SEQ ID NO: 88; and/or
a HC of SEQ ID NO: 91 and a LC of SEQ ID NO: 92.

The invention also provides an isolated anti-TMEFF2 antibody or an antigen-binding fragment thereof, comprising
a HCDR1, a HCDR2, a HCDR3, a LCDR1, a LCDR2 and a LCDR3 of SEQ ID NOs: 10, 12, 15, 18, 20 and 86, respectively;
a VH of SEQ ID NO: 89 and a VL of SEQ ID NO: 90; and/or a HC of SEQ ID NO: 93 and a LC of SEQ ID NO: 94.

The invention also provides a pharmaceutical composition comprising the anti-TMEFF2 antibody or the antigen-binding fragment thereof of the invention and a pharmaceutically acceptable carrier.

The invention also provides an isolated polynucleotide encoding the anti-TMEFF2 antibody or the antigen binding fragment thereof of the invention, encoding the anti-TMEFF2 antibody VH of SEQ ID NOs: 25, 26, 27, 87 or 89 and/or the VL of SEQ ID NOs: 28, 29, 30, 31, 88 or 90, or comprising a polynucleotide sequence of SEQ ID NOs: 39, 40, 41, 42, 43, 44, 45, 46, 47, 48, 49, 50, 51, 52, 95, 96, 97, 98, 99, 100, 101 or 102.

The invention also provides a vector comprising the polynucleotide of the invention.

The invention also provides a host cell comprising the vector of the invention.

The invention also provides a method of producing the anti-TMEFF2 antibody or the antigen binding fragment thereof of the invention, comprising culturing the host cell of the invention in conditions that the antibody or the anting binding fragment is expressed, and recovering the antibody or the antigen binding fragment thereof produced by the host cell.

The invention also provides a method of treating a TMEFF2 positive cancer in a subject in need thereof, comprising administering a therapeutically effective amount of the isolated anti-TMEFF2 antibody or the antigen binding fragment thereof of the invention or the pharmaceutical composition of the invention to the subject to treat the TMEFF2 positive cancer.

The invention also provides an anti-idiotypic antibody binding to the anti-TMEFF2 antibody of the invention.

The invention also provides a kit comprising the anti-TMEFF2 antibody or the antigen binding fragment thereof of the invention.

The invention also provides an isolated bispecific anti-TMEFF2/anti-CD3 antibody or an antigen binding fragment thereof comprising a first domain that binds TMEFF2 and a second domain that binds CD3.

The invention also provides an isolated bispecific anti-TMEFF2/anti-CD3 antibody or an antigen binding fragment thereof comprising a first domain that binds TMEFF2 and a second domain that binds CD3, wherein the antibody binds to a membrane proximal region of SEQ ID NO: 110 of TMEFF2.

The invention also provides an isolated bispecific anti-TMEFF2/anti-CD3 antibody or an antigen binding fragment thereof, wherein the antibody competes for binding to the membrane proximal region of TMEFF2 with a reference antibody comprising a heavy chain variable region (VH) of SEQ ID NO: 25 and a light chain variable region (VL) of SEQ ID NO: 28, the VH of SEQ ID NO: 26 and the VL of SEQ ID NO: 29, the VH of SEQ ID NO: 27 and the VL of SEQ ID NO: 30, the VH of SEQ ID NO: 26 and the VL of SEQ ID NO: 31, the VH of SEQ ID NO: 87 and the VL of SEQ ID NO: 88, or the VH of SEQ ID NO: 89 and the VL of SEQ ID NO: 90.

The invention also provides an isolated bispecific anti-TMEFF2/anti-CD3 antibody or an antigen binding fragment thereof, wherein the antibody binds an epitope of SEQ ID NO: 57 or SEQ ID NO: 58 on TMEFF2.

The invention also provides an isolated bispecific anti-TMEFF2/anti-CD3 antibody or an antigen binding fragment thereof comprising a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 22, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;

the first domain comprises a VH of SEQ ID NO: 25 and a VL of SEQ ID NO: 28, and the second domain comprises the VH of SEQ ID NO: 66 and the VL of SEQ ID NO: 67; and/or the bispecific anti-TMEFF2/anti-CD3 antibody or the antigen binding fragment thereof comprises a first heavy chain (HC1) of SEQ ID NO: 32, a first light chain (LC1) of SEQ ID NO: 35, a second heavy chain (HC2) of SEQ ID NO: 76 and a second light chain (LC2) of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 22, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;

the first domain comprises a VH of SEQ ID NO: 25 and a VL of SEQ ID NO: 28, and the second domain comprises the VH of SEQ ID NO: 74 and the VL of SEQ ID NO: 75; and/or the bispecific anti-TMEFF2/anti-CD3 antibody or the antigen binding fragment thereof comprises a HC1 of SEQ ID NO: 32, a LC1 of SEQ ID NO: 35, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 11, 13, 16, 19, 21, and 23, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;

the first domain comprises a VH of SEQ ID NO: 26 and a VL of SEQ ID NO: 29, and the second domain comprises the VH of SEQ ID NO: 66 and the VL of SEQ ID NO: 67; and/or the bispecific anti-TMEFF2/anti-CD3 antibody or the antigen binding fragment thereof comprises a HC1 of SEQ ID NO: 33, a LC1 of SEQ ID NO: 36, a HC2 of SEQ ID NO: 76 and a LC2 of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 11, 13, 16, 19, 21, and 23, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;

the first domain comprises a VH of SEQ ID NO: 26 and a VL of SEQ ID NO: 29, and the second domain comprises the VH of SEQ ID NO: 74 and the VL of SEQ ID NO:75; and/or the bispecific anti-TMEFF2/anti-CD3 antibody or the antigen binding fragment thereof comprises a HC1 of SEQ ID NO: 33, a LC1 of SEQ ID NO: 36, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
   the first domain comprises a HCDR1, a HCDR2, a HCDR3, a LCDR1, a LCDR2 and a LCDR3 of SEQ ID NOs: 10, 14, 17, 18, 20 and 24, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
   the first domain comprises a VH of SEQ ID NO: 27 and a VL of SEQ ID NO: 30, and the second domain comprises the VH of SEQ ID NO: 66 and the VL of SEQ ID NO: 67; and/or the bispecific anti-TMEFF2/anti-CD3 antibody or the antigen binding fragment thereof comprises a HC1 of SEQ ID NO: 34, a LC1 of SEQ ID NO: 37, a HC2 of SEQ ID NO: 76 and a LC2 of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein
   the first domain comprises a HCDR1, a HCDR2, a HCDR3, a LCDR1, a LCDR2 and a LCDR3 of SEQ ID NOs: 10, 14, 17, 18, 20 and 24, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
   the first domain comprises a VH of SEQ ID NO: 27 and a VL of SEQ ID NO: 30, and the second domain comprises the VH of SEQ ID NO: 74 and the VL of SEQ ID NO: 75; and/or
   the bispecific anti-TMEFF2/anti-CD3 antibody or the antigen binding fragment thereof comprises a HC1 of SEQ ID NO: 34, a LC1 of SEQ ID NO: 37, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
   the first domain comprises a HCDR1, a HCDR2, a HCDR3, a LCDR1, a LCDR2 and a LCDR3 of SEQ ID NOs: 11, 13, 16, 18, 20 and 22, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
   the first domain comprises a VH of SEQ ID NO: 26 and a VL of SEQ ID NO: 31, and the second domain comprises the VH of SEQ ID NO: 66 and the VL of SEQ ID NO: 67; and/or
   the bispecific anti-TMEFF2/anti-CD3 antibody or the antigen binding fragment thereof comprises a HC1 of SEQ ID NO: 33, a LC1 of SEQ ID NO: 38, a HC2 of SEQ ID NO: 76 and a LC2 of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein
   the first domain comprises a HCDR1, a HCDR2, a HCDR3, a LCDR1, a LCDR2 and a LCDR3 of SEQ ID NOs: 11, 13, 16, 18, 20 and 22, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
   the first domain comprises a VH of SEQ ID NO: 26 and a VL of SEQ ID NO: 31, and the second domain comprises the VH of SEQ ID NO: 74 and the VL of SEQ ID NO: 75; and/or
   the bispecific anti-TMEFF2/anti-CD3 antibody or the antigen binding fragment thereof comprises a HC1 of SEQ ID NO: 33, a LC1 of SEQ ID NO: 38, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
   the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
   the first domain comprises a VH of SEQ ID NO: 87 and a VL of SEQ ID NO: 88, and the second domain comprises the VH of SEQ ID NO: 66 and the VL of SEQ ID NO: 67; and/or
   the bispecific anti-TMEFF2/anti-CD3 antibody or the antigen binding fragment thereof comprises a HC1 of SEQ ID NO: 91, a LC1 of SEQ ID NO: 92, a HC2 of SEQ ID NO: 76 and a LC2 of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein
   the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
   the first domain comprises a VH of SEQ ID NO: 87 and a VL of SEQ ID NO: 88, and the second domain comprises the VH of SEQ ID NO: 74 and the VL of SEQ ID NO: 75; and/or
   the bispecific anti-TMEFF2/anti-CD3 antibody or the antigen binding fragment thereof comprises a HC1 of SEQ ID NO: 91, a LC1 of SEQ ID NO: 92, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
   the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
   the first domain comprises a VH of SEQ ID NO: 89 and a VL of SEQ ID NO: 90, and the second domain comprises the VH of SEQ ID NO: 66 and the VL of SEQ ID NO: 67; and/or
   the bispecific anti-TMEFF2/anti-CD3 antibody or the antigen binding fragment thereof comprises a HC1 of SEQ ID NO: 93, a LC1 of SEQ ID NO: 94, a HC2 of SEQ ID NO: 76 and a LC2 of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;

the first domain comprises a VH of SEQ ID NO: 89 and a VL of SEQ ID NO: 90, and the second domain comprises the VH of SEQ ID NO: 74 and the VL of SEQ ID NO: 75; and/or the bispecific anti-TMEFF2/anti-CD3 antibody or the antigen binding fragment thereof comprises a HC1 of SEQ ID NO: 93, a LC1 of SEQ ID NO: 94, a HC2 of SEQ ID NO: 78 and a LC2 of SEQ ID NO: 79.

The invention also provides a pharmaceutical composition comprising the bispecific anti-TMEFF2/anti-CD3 antibody or the antigen binding fragment thereof of the invention and a pharmaceutically acceptable carrier.

The invention also provides a polynucleotide encoding the bispecific anti-TMEFF2/anti-CD3 antibody or the antigen binding fragment thereof of the invention.

The invention also provides a method of producing a bispecific anti-TMEFF2/anti-CD3 antibody, comprising culturing the host cell of the invention in conditions that the antibody is expressed, and recovering and purifying the bispecific anti-TMEFF2/anti-CD3 antibody or the antigen binding fragment thereof produced by the host cell.

The invention also provides a method of producing the bispecific anti-TMEFF2/anti-CD3 antibody or the antigen binding fragment thereof, comprising:

combining a monospecific bivalent TMEFF2 antibody having two identical HC1 and two identical LC1 and a monospecific bivalent CD3 antibody having two identical HC2 and two identical LC2 in a mixture of about 1:1 molar ratio;

introducing a reducing agent into the mixture;

incubating the mixture about ninety minutes to about six hours;

removing the reducing agent; and purifying the bispecific anti-TMEFF2/anti-CD3 antibody or the antigen binding fragment thereof that comprises the HC1, the LC1, the HC2 and the LC2.

The invention also provides a method of treating a TMEFF2 positive cancer in a subject in need thereof, comprising administering a therapeutically effective amount of the bispecific anti-TMEFF2/anti-CD3 antibody or the antigen binding fragment thereof of the invention or the pharmaceutical composition of the invention to the subject to treat the TMEFF2 positive cancer.

The invention also provides an anti-idiotypic antibody binding to the bispecific anti-TMEFF2/anti-CD3 antibody or the antigen binding fragment thereof of the invention.

The invention also provides a kit comprising the bispecific anti-TMEFF2/anti-CD3 antibody of the invention.

BRIEF DESCRIPTION OF THE DRAWINGS

FIG. 1 shows the alignment of select anti-TMEFF2 antibody heavy chain variable regions (VH). The VH regions are identified by their SEQ ID NO: at the beginning of each row.

FIG. 2 shows the alignment of select anti-TMEFF2 antibody light chain variable regions (VL). The VH regions are identified by their SEQ ID NO: at the beginning of each row.

DETAILED DESCRIPTION OF THE INVENTION

Figure 3:
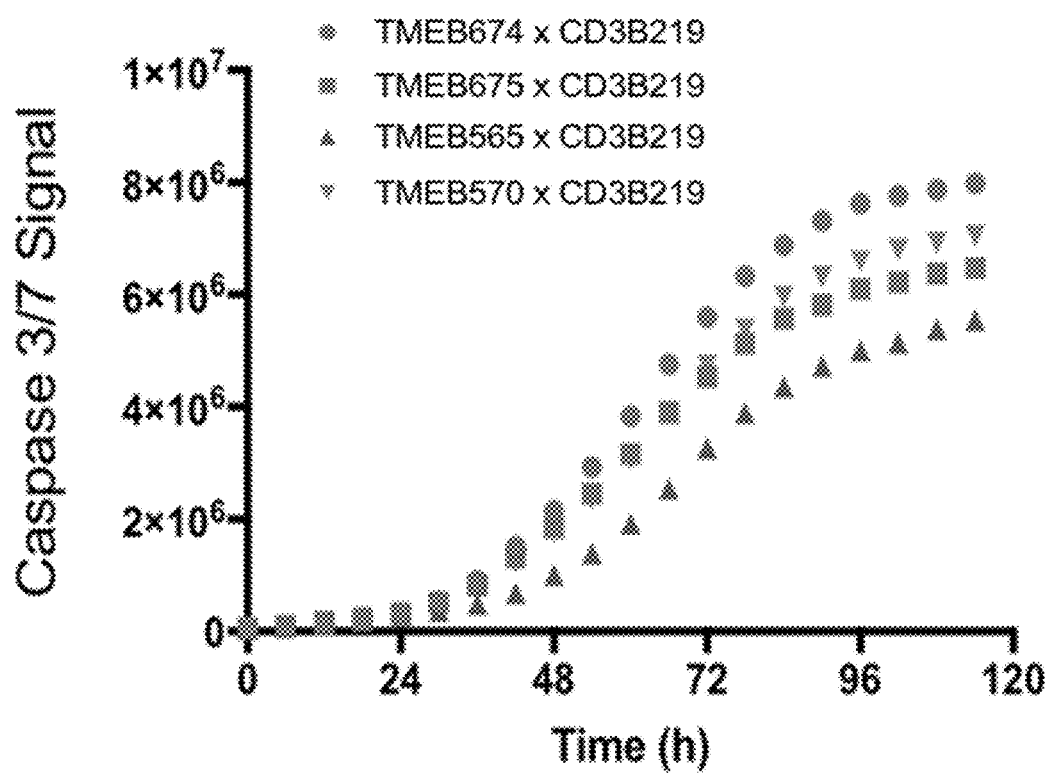
FIG. 3 shows killing of LnCaP cells over time as measured by increased caspase 3/7 activity by select bispecific anti-TMEFF2/anti-CD3 antibodies.

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

"Specific binding" or "specifically binds" or "specifically binding" or "binds" refers to an antibody binding to an antigen or an epitope within the antigen with greater affinity than for other antigens. Typically, the antibody binds to the antigen or the epitope within the antigen with an equilibrium dissociation constant ($K_D$) of about $5 \times 10^{-8}$ M or less, for example about $1 \times 10^{-9}$ M or less, about $1 \times 10^{-10}$ M or less, about $1 \times 10^{-11}$ M or less, or about $1 \times 10^{-12}$ M or less, typically with the $K_D$ that is at least one hundred-fold less than its $K_D$ for binding to a non-specific antigen (e.g., BSA, casein). The dissociation constant may be measured using protocols described herein. Antibodies that bind to the antigen or the epitope within the antigen may, however, have cross-reactivity to other related antigens, for example to the same antigen from other species (homologs), such as human or monkey, for example *Macaca fascicularis* (cynomolgus, cyno) or *Pan troglodytes* (chimpanzee, chimp). While a monospecific antibody binds one antigen or one epitope, a bispecific antibody binds two distinct antigens or two distinct epitopes.

"Antibodies" is meant in a broad sense and includes immunoglobulin molecules including monoclonal antibodies including murine, human, humanized and chimeric monoclonal antibodies, antigen binding fragments, multi-specific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are antibody regions that bind an antigen. CDRs may be defined using various delineations such as Kabat (Wu et al. (1970) *J Exp Med* 132: 211-50) (Kabat et al., *Sequences of Proteins of Immunological Interest*, 5th Ed. Public Health Service, National Institutes of Health, Bethesda, Md., 1991), Chothia (Chothia et al. (1987) *J Mol Biol* 196: 901-17), IMGT (Lefranc et al. (2003) *Dev Comp Immunol* 27: 55-77) and AbM (Martin and Thornton (1996) *J Bmol Biol* 263: 800-15). The correspondence between the various delineations and variable region numbering are described (see e.g. Lefranc et al. (2003) *Dev Comp Immunol* 27: 55-77; Honegger and Pluckthun, (2001) *J Mol Biol* 309:657-70; International ImMunoGeneTics (IMGT) database; Web resources, www.imgt.org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen binding fragment" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or synthetic HCDR3 incorporated into human immunoglobulin gene libraries displayed on phage, for example as described in Shi et al., (2010) J Mol Biol 397:385-96, and in Int. Patent Publ. No. WO2009/085462.

Antibodies in which at least one CDR is derived from a non-human species are not included in the definition of "human antibody".

"Recombinant" refers to DNA, antibodies and other proteins that are prepared, expressed, created or isolated by recombinant means when segments from different sources are joined to produce recombinant DNA, antibodies or proteins.

"Epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca cynomolgus* (cynomolgus, cyno) or *Pan troglodytes*, or may bind an epitope that is shared between two or more distinct antigens.

"Multispecific" refers to an antibody that specifically binds two or more distinct antigens or two or more distinct epitopes within the same antigen. The multispecific antibody may have cross-reactivity to other related antigens, for example to the same antigen from other species (homologs), such as human or monkey, for example *Macaca* cynomolgus (cynomolgus, cyno) or *Pan troglodytes*, or may bind an epitope that is shared between two or more distinct antigens.

"Variant" refers to a polypeptide or a polynucleotide that differs from a reference polypeptide or a reference polynucleotide by one or more modifications, for example one or more substitutions, insertions or deletions.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system, such as a cell, virus, animal, plant, and reconstituted biological systems utilizing biological components capable of duplicating a vector. The vector polynucleotide may be DNA or RNA molecules or a hybrid of these, single stranded or double stranded.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is an exemplary synthetic polynucleotide.

"Polypeptide" or "protein" refers to a molecule that comprises at least two amino acid residues linked by a peptide bond to form a polypeptide. Small polypeptides of less than 50 amino acids may be referred to as "peptides".

"TMEFF2" refers to human transmembrane protein with EGF like and two follistatin like domains 2, also called tomoregulin 2. The amino acid sequence of the full length human TMEFF2 is shown in SEQ ID NO: 1. The extracellular domain of TMEFF2 is shown in SEQ ID NO: 2 and spans residues 40-374 of the full length TMEFF2. TMEFF2 extracellular domain harbors three distinct subdomains, the Kazal-like 1 (residues 85-137), the Kazal-like 2 (residues 176-229) and the EGF domain (residues 261-301). The TMEFF2 EGF domain is shown in SEQ ID NO: 3. The TMEFF2 "membrane proximal region" refers to the TMEFF2 region of SEQ ID NO: 110, which encompasses the EGF domain and the N-C-terminal linker regions (e.g. residues 230-320 of full length human TMEFF2 of SEQ ID NO: 1). All references to proteins, polypeptides and protein fragments herein are intended to refer to the human version of the respective protein, polypeptide or protein fragment unless explicitly specified as being from a non-human species. Thus, "TMEFF2" means human TMEFF2 unless specified as being from a non-human species, e.g., "mouse TMEFF2" or "monkey TMEFF2" etc.

```
(full length human TMEFF2)
                                               SEQ ID NO: 1
MVLWESPRQCSSWTLCEGFCWLLLLPVMLLIVARPVKLAAFPTSLSDCQT

PTGWNCSGYDDRENDLFLCDTNTCKFDGECLRIGDTVTCVCQFKCNNDYV

PVCGSNGESYQNECYLRQAACKQQSEILVVSEGSCATDAGSGSGDGVHEG

SGETSQKETSTCDICQFGAECDEDAEDVWCVCNIDCSQTNFNPLCASDGK

SYDNACQIKEASCQKQEKIEVMSLGRCQDNTTTTTKSEDGHYARTDYAEN

ANKLEESAREHHIPCPEHYNGFCMHGKCEHSINMQEPSCRCDAGYTGQHC

EKKDYSVLYVVPGPVRFQYVLIAAVIGTIQIAVICVVVLCITRKCPRSNR

IHRQKQNTGHYSSDNTTRASTRLI (extracellular domain of human TMEFF2)
                                               SEQ ID NO: 2
FPTSLSDCQTPTGWNCSGYDDRENDLFLCDTNTCKFDGECLRIGDTVTCV

CQFKCNNDYVPVCGSNGESYQNECYLRQAACKQQSEILVVSEGSCATDAG

SGSGDGVHEGSGETSQKETSTCDICQFGAECDEDAEDVWCVCNIDCSQTN

FNPLCASDGKSYDNACQIKEASCQKQEKIEVMSLGRCQDNTTTTTKSEDG

HYARTDYAENANKLEESAREHHIPCPEHYNGFCMHGKCEHSINMQEPSCR

CDAGYTGQHCEKKDYSVLYVVPGPVRFQYVLIAAVIGTIQIAVICVVVLC

ITRKCPRSNRIHRQKQNTGHYSSDNTTRASTRLI

TMEFF2 EGF domain
                                               SEQ ID NO: 3
HHIPCPEHYNGFCMHGKCEHSINMQEPSCRCDAGYTGQHCE TMEFF2 membrane proximal region
                                             SEQ ID NO: 110
NTTTTTKSEDGHYARTDYAENANKLEESAREHHIPCPEHYNGFCMHGKCE

HSINMQEPSCRCDAGYTGQHCEKKDYSVLYVVPGPVRFQYV
```

"CD3" refers to an antigen which is expressed on T cells as part of the multimolecular T cell receptor (TCR) complex and which consists of a homodimer or heterodimer formed from the association of two or four receptor chains: CD3 epsilon, CD3 delta, CD3 zeta and CD3 gamma. Human CD3 epsilon comprises the amino acid sequence of SEQ ID NO: 4. All references to proteins, polypeptides and protein fragments herein are intended to refer to the human version of the respective protein, polypeptide or protein fragment unless explicitly specified as being from a non-human species. Thus, "CD3" means human CD3 unless specified as being from a non-human species, e.g., "mouse CD3" "monkey CD3," etc.

(Human CD3 epsilon)
SEQ ID NO: 4
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI (Human CD3 epsilon extracellular domain)
SEQ ID NO: 5
DGNEEMGGITQTPYKVSISGTTVILTCPQYPGSEILWQHNDKNIGGDEDD

KNIGSDEDHLSLKEFSELEQSGYYVCYPRGSKPEDANFYLYLRARVCENC

MEMD

"Bispecific anti-TMEFF2/anti-CD3 antibody", TMEFF2/CD3 antibody, TMEFF2×CD3 antibody and the like refer to an antibody that binds TMEFF2 and CD3.

"In combination with" means that two or more therapeutics are administered to a subject together in a mixture, concurrently as single agents or sequentially as single agents in any order.

"TMEFF2 positive cancer" refers to a cancer tissue or a cancer cell that displays measurable level of TMEFF2 protein. Level of TMEFF2 protein may be measured using well known assays using, for example ELISA, immunofluorescence, flow cytometry or radioimmunoassay on live or lysed cells.

"Sample" refers to a collection of similar fluids, cells, or tissues isolated from a subject, as well as fluids, cells, or tissues present within a subject. Exemplary samples are of biological fluids such as blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage, liquid solutions contacted with a subject or biological source, for example, cell and organ culture medium including cell or organ conditioned medium, lavage fluids and the like, tissue biopsies, fine needle aspirations or surgically resected tumor tissue.

A "cancer cell" or a "tumor cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid or uptake of exogenous nucleic acid, it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo (Freshney, Culture of Animal Cells: A Manual of Basic Technique (3rd ed. 1994)).

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is greater.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

"Treat" or "treatment" refers to both therapeutic treatment and prophylactic or preventative measures, wherein the object is to prevent or slow down (lessen) an undesired physiological change or disorder. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, Md. (1991), unless otherwise explicitly stated.

Conventional one and three-letter amino acid codes are used herein as shown in Table 1.

TABLE 1

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |

TABLE 1-continued

| Amino acid | Three-letter code | One-letter code |
|---|---|---|
| Tryptophan | Trp | W |
| Tyrosine | Tyr | Y |
| Valine | Val | V |

Compositions of Matter

The present invention provides anti-TMEFF2 antibodies or antigen binding fragments thereof, multispecific antibodies comprising the antigen binding fragments of the anti-TMEFF2 antibodies of the invention, and bispecific anti-TMEFF2/anti-CD3 antibodies or antigen-binding fragments thereof. The present invention provides polypeptides and polynucleotides encoding the antibodies of the invention or complementary nucleic acids thereof, vectors, host cells, and methods of making and using them.

Anti-TMEFF2 Antibodies

TMEFF2 expression is significantly enriched in prostatic tissue and prostate adenocarcinoma relative to other normal tissues. Membranous TMEFF2 is retained throughout disease progression, serving as a possible target for anti-tumor therapeutics. TMEFF2 is known to be cleaved by protease, resulting in soluble forms of the antigen. In the instant invention antibodies directed to the membrane proximal region of TMEFF2 were generated to maximize antibody binding to membrane TMEFF2 and minimize the possibility of the resulting antibodies binding soluble TMEFF2 forms.

The invention provides an isolated anti-TMEFF2 antibody or an antigen binding fragment thereof that binds to a membrane proximal region of SEQ ID NO: 110 of TMEFF2. The anti-TMEFF2 antibodies of the invention binding the membrane proximal region of TMEFF2 are not internalized by cells. While wishing not to be bound by any particular theory, it can be expected that non-internalizing anti-TMEFF2 antibodies have improved oncogenic effect mediated by antibody effector functions resulting from lack of internalization and degradation of TMEFF2 when compared to internalizing anti-TMEFF2 antibodies.

"Binds to a membrane proximal region" means that 90% of antibody epitope residues identified using hydrogen/deuterium exchange (H/D exchange) reside within the membrane proximal region of TMEFF2. The epitope residues are those which are protected by the test antibody by at least 5% difference in deuteration levels through H/D exchange. Exemplary such antibodies are TMEB675, TMEB570, TMEB674, TMEB565, TMEB762 and TMEB757 as described herein.

In some embodiments, the isolated anti-TMEFF2 antibody or the antigen binding fragment thereof binds within residues HGKCEHSINMQEPSC (SEQ ID NO: 57) or DAGYTGQHCEKKDYSVL (SEQ ID NO: 58) to the membrane proximal region of TMEFF2. An exemplary anti-TMEFF2 antibody binding within residues HGKCEHSINMQEPSC (SEQ ID NO: 57) is TMEB570. An exemplary anti-TMEFF2 antibody binding within residues DAGYTGQHCEKKDYSVL (SEQ ID NO: 58) is TMEB675. TMEB675 variants TMEB762 and TMEB757 are also expected to bind the membrane proximal region of TMEFF2 within residues DAGYTGQHCEKKDYSVL (SEQ ID NO: 58).

In an H/D exchange assay, recombinantly expressed TMEFF2 ECD is incubated in the presence or absence of the antibody in deuterated water for predetermined times resulting in deuterium incorporation at exchangeable hydrogen atoms which are unprotected by the antibody, followed by protease digestion of the protein and analyses of the peptide fragments using LC-MS. H/D exchange assay can be performed using known protocols. An exemplary protocol is described in Example 5.

The invention also provides an isolated anti-TMEFF2 antibody or an antigen binding fragment thereof, wherein the antibody or the antigen binding fragment thereof competes for binding to the membrane proximal region of TMEFF2 with a reference antibody comprising a heavy chain variable region (VH) of SEQ ID NO: 25 and a light chain variable region (VL) of SEQ ID NO: 28, the VH of SEQ ID NO: 26 and the VL of SEQ ID NO: 29, the VH of SEQ ID NO: 27 and the VL of SEQ ID NO: 30, the VH of SEQ ID NO: 26 and the VL of SEQ ID NO: 31, the VH of SEQ ID NO: 87 and the VL of SEQ ID NO: 88, or the VH of SEQ ID NO: 89 and the VL of SEQ ID NO: 90.

Competition for binding of a test antibody to the membrane proximal region of TMEFF2 with the reference antibody may be assayed in vitro using well known methods. For example, binding of MSD Sulfo-Tag™ NHS-ester-labeled test antibody to the membrane proximal region of TMEFF2 in the presence of an unlabeled reference antibody may be assessed by ELISA, or Biacore analyses or flow cytometry may be used to demonstrate competition. The test antibody competes for binding to TMEFF2 with the reference antibody when the test antibody inhibits binding of the reference antibody to the membrane proximal region of TMEFF2 by 85% or more, for example 90% or more, or 95% or more.

The invention also provides an isolated anti-TMEFF2 antibody or an antigen binding fragment thereof comprising a heavy chain complementarity determining region 1 (HCDR1), a HCDR2, a HCDR3, a light chain complementarity determining region 1 (LCDR1), a LCDR2 and a LCDR3 of SEQ ID NOs: 10, 12, 15, 18, 20 and 22, respectively;
SEQ ID NOs: 11, 13, 16, 19, 21, and 23, respectively;
SEQ ID NOs: 10, 14, 17, 18, 20 and 24, respectively;
SEQ ID NOs: 11, 13, 16, 18, 20 and 22, respectively; or
SEQ ID NOs: 10, 12, 15, 18, 20 and 86, respectively.

In some embodiments, the isolated anti-TMEFF2 antibody or the antigen binding fragment thereof of the invention binds to the membrane proximal region of TMEFF2 with an equilibrium dissociation constant ($K_D$) of about $0.4 \times 10^{-9}$ M or less, wherein the $K_D$ is measured using surface plasmon resonance in acetate buffer at pH 4.5-5.0 at room temperature.

In some embodiments, the isolated anti-TMEFF2 antibody or the antigen binding fragment thereof binds to the membrane proximal region of TMEFF2 with the $K_D$ of between about $0.1 \times 10^{-10}$ M and about $0.4 \times 10^{-9}$ M.

The affinity of an antibody to the membrane proximal region of TMEFF2 may be determined experimentally using any suitable method. An exemplary method utilizes ProteOn XPR36, Biacore 3000 or KinExA instrumentation, ELISA or competitive binding assays known to those skilled in the art. The measured affinity of an antibody to TMEFF2 may vary if measured under different conditions (e.g., osmolarity, pH). Thus, measurements of affinity and other binding parameters (e.g., $K_D$, $K_{on}$, and Koff) are typically made with standardized conditions and a standardized buffer, such as the buffer described herein. Skilled in the art will appreciate that the internal error for affinity measurements for example using Biacore 3000 or ProteOn (measured as standard deviation, SD) can typically be within 5-33% for measurements within the typical limits of detection. Therefore, the term "about" when referring to a $K_D$ value reflects the typical standard deviation in the assay. For example, the typical SD for a $K_D$ of $1\times10^{-9}$ M is up to $+0.33\times10^{-9}$ M.

The invention also provides an isolated anti-TMEFF2 antibody or an antigen binding fragment thereof that binds to the membrane proximal region of TMEFF2, comprising a heavy chain variable region (VH) framework derived from VH3_3-23 (SEQ ID NO: 53) or VH1_1-69 (SEQ ID NO: 54).

The invention also provides an isolated anti-TMEFF2 antibody or an antigen binding fragment thereof that binds to the membrane proximal region of TMEFF2, comprising a light chain variable region (VL) framework derived from VKI_L11 (SEQ ID NO: 55) or VKIIII_A27 (SEQ ID NO: 56).

The invention also provides an isolated anti-TMEFF2 antibody or an antigen binding fragment thereof that binds to the membrane proximal region of TMEFF2, comprising a VH framework and a VL framework derived from VH3_3-23 of SEQ ID NO: 53 and VKI_L11 of SEQ ID NO: 55, respectively.

The invention also provides an isolated anti-TMEFF2 antibody or an antigen binding fragment thereof that binds to the membrane proximal region of TMEFF2, comprising a VH framework and a VL framework derived from VH1_1-69 of SEQ ID NO: 54 and VKIII_A27 of SEQ ID NO: 56, respectively.

The invention also provides an isolated anti-TMEFF2 antibody or an antigen binding fragment thereof that binds to the membrane proximal region of TMEFF2, comprising a VH framework and a VL framework derived from VH1_1-69 of SEQ ID NO: 54 and VKI_L11 of SEQ ID NO: 55, respectively.

Antibodies comprising heavy or light chain variable regions "derived from" a particular framework or germline sequence refer to antibodies obtained from a system that uses human germline immunoglobulin genes, such as from transgenic mice, rats or chicken or from phage display libraries as discussed herein. An antibody containing particular framework derived from germline sequence may contain amino acid differences as compared to the sequence it was derived from, due to, for example, naturally-occurring somatic mutations or intentional substitutions.

The invention also provides an isolated anti-TMEFF2 antibody or an antigen binding fragment thereof, comprising a HCDR1, a HCDR2, a HCDR3, a LCDR1, a LCDR2 and a LCDR3 of SEQ ID NOs: 10, 12, 15, 18, 20 and 22, respectively.

In some embodiments, the isolated anti-TMEFF2 antibody or the antigen-binding fragment thereof comprises a VH of SEQ ID NO: 25 and a VL of SEQ ID NO: 28.

In some embodiments, the VH is encoded by a polynucleotide of SEQ ID NO: 39 and the VL is encoded by a polynucleotide of SEQ ID NO: 42.

In some embodiments, the isolated anti-TMEFF2 antibody or the antigen binding fragment thereof comprises a HC of SEQ ID NO: 32 and a LC of SEQ ID NO: 35.

In some embodiments, the HC is encoded by a polynucleotide of SEQ ID NO: 46 and the VL is encoded by a polynucleotide of SEQ ID NO: 49.

The invention also provides an isolated anti-TMEFF2 antibody or an antigen binding fragment thereof comprising a HCDR1, a HCDR2, a HCDR3, a LCDR1, a LCDR2 and a LCDR3 of SEQ ID NOs: 11, 13, 16, 19, 21 and 23, respectively.

In some embodiments, the isolated anti-TMEFF2 antibody or the antigen-binding fragment thereof comprises a VH of SEQ ID NO: 26 and a VL of SEQ ID NO: 29.

In some embodiments, the VH is encoded by a polynucleotide of SEQ ID NO: 40 and the VL is encoded by a polynucleotide of SEQ ID NO: 43.

In some embodiments, the isolated anti-TMEFF2 antibody or the antigen binding fragment thereof comprises a HC of SEQ ID NO: 33 and a LC of SEQ ID NO: 36.

In some embodiments, the HC is encoded by a polynucleotide of SEQ ID NO: 47 and the LC is encoded by a polynucleotide of SEQ ID NO: 50.

The invention also provides an isolated anti-TMEFF2 antibody or an antigen binding fragment thereof comprising a HCDR1, a HCDR2, a HCDR3, a LCDR1, a LCDR2 and a LCDR3 of SEQ ID NOs: 10, 14, 17, 18, 20 and 24, respectively.

In some embodiments, the isolated anti-TMEFF2 antibody or the antigen binding fragment thereof comprises a VH of SEQ ID NO: 27 and a VL of SEQ ID NO: 30.

In some embodiments, the VH is encoded by a polynucleotide of SEQ ID NO: 41 and the VL is encoded by a polynucleotide of SEQ ID NO: 44.

In some embodiments, the isolated anti-TMEFF2 antibody or the antigen binding fragment thereof comprises a HC of SEQ ID NO: 34 and a LC of SEQ ID NO: 37.

In some embodiments, the HC is encoded by a polynucleotide of SEQ ID NO: 48 and the LC is encoded by a polynucleotide of SEQ ID NO: 51.

The invention also provides an isolated anti-TMEFF2 antibody or an antigen binding fragment thereof comprising a HCDR1, a HCDR2, a HCDR3, a LCDR1, a LCDR2 and a LCDR3 of SEQ ID NOs: 11, 13, 16, 18, 20 and 22, respectively.

In some embodiments, the isolated anti-TMEFF2 antibody or the antigen binding fragment thereof comprises a VH of SEQ ID NO: 26 and a VL of SEQ ID NO: 31.

In some embodiments, the VH is encoded by a polynucleotide of SEQ ID NO: 40 and the VL is encoded by a polynucleotide of SEQ ID NO: 45.

In some embodiments, the isolated anti-TMEFF2 antibody or the antigen binding fragment thereof comprises a HC of SEQ ID NO: 33 and a LC of SEQ ID NO: 38.

In some embodiments, the HC is encoded by a polynucleotide of SEQ ID NO: 47 and the LC is encoded by a polynucleotide of SEQ ID NO: 52.

The invention also provides an isolated anti-TMEFF2 antibody or an antigen binding fragment thereof comprising a HCDR1, a HCDR2, a HCDR3, a LCDR1, a LCDR2 and a LCDR3 of SEQ ID NOs: 10, 12, 15, 18, 20 and 86, respectively.

In some embodiments, the isolated anti-TMEFF2 antibody or the antigen-binding fragment thereof comprises a VH of SEQ ID NO: 87 and a VL of SEQ ID NO: 88.

In some embodiments, the VH is encoded by a polynucleotide of SEQ ID NO: 95 and the VL is encoded by a polynucleotide of SEQ ID NO: 96.

In some embodiments, the isolated anti-TMEFF2 antibody or the antigen binding fragment thereof comprises a HC of SEQ ID NO: 91 and a LC of SEQ ID NO: 92.

In some embodiments, the HC is encoded by a polynucleotide of SEQ ID NO: 97 and the LC is encoded by a polynucleotide of SEQ ID NO: 98.

The invention also provides an isolated anti-TMEFF2 antibody or an antigen binding fragment thereof comprising a HCDR1, a HCDR2, a HCDR3, a LCDR1, a LCDR2 and a LCDR3 of SEQ ID NOs: 10, 12, 15, 18, 20 and 86, respectively.

In some embodiments, the isolated anti-TMEFF2 antibody or the antigen binding fragment thereof comprises a VH of SEQ ID NO: 89 and a VL of SEQ ID NO: 90.

In some embodiments, the VH is encoded by a polynucleotide of SEQ ID NO: 99 and the VL is encoded by a polynucleotide of SEQ ID NO: 100.

In some embodiments, the isolated anti-TMEFF2 antibody or the antigen binding fragment thereof comprises a HC of SEQ ID NO: 93 and a LC of SEQ ID NO: 94.

In some embodiments, the HC is encoded by a polynucleotide of SEQ ID NO: 101 and the LC is encoded by a polynucleotide of SEQ ID NO: 102.

In some embodiments, the isolated anti-TMEFF2 antibody or the antigen binding fragment thereof is a multispecific antibody.

In some embodiments, the isolated anti-TMEFF2 antibody or the antigen binding fragment thereof is a bispecific antibody.

In some embodiments, the isolated anti-TMEFF2 bispecific antibody or the antigen binding fragment thereof binds a T cell antigen.

In some embodiments, the isolated anti-TMEFF2 bispecific antibody or the antigen binding fragment thereof binds CD3.

In some embodiments, the isolated anti-TMEFF2 bispecific antibody or the antigen-binding fragment thereof binds CD3 epsilon.

The VH, the VL, the HCDR, the LCDR, the HC and the LC sequences of exemplary anti-TMEFF2 antibodies of the invention are shown in Tables 5-12.

Although the embodiments illustrated in the Examples comprise pairs of variable domains, one from a heavy chain and one from a light chain, a skilled artisan will recognize that alternative embodiments may comprise single heavy or light chain variable domains. The single variable domain may be used to screen for variable domains capable of forming a two-domain specific antigen-binding fragment capable of binding to TMEFF2. The screening may be accomplished by phage display screening methods using for example hierarchical dual combinatorial approach disclosed in Int. Patent Publ. No. WO1992/01047. In this approach, an individual colony containing either a VH or a VL chain clone is used to infect a complete library of clones encoding the other chain (VL or VH), and the resulting two-chain specific antigen-binding domain is selected in accordance with phage display techniques using known methods and those described herein. Therefore, the individual VH and VL polypeptide chains are useful in identifying additional anti-TMEFF2 antibodies using the methods disclosed in Int. Patent Publ. No. WO1992/01047.

Homologous Antibodies

Variants of the anti-TMEFF2 antibodies or antigen-binding fragments thereof of the invention comprising VH or VL amino acid sequences shown in Table 9 are within the scope of the invention. For example, variants may comprise one, two, three, four, five, six, seven, eight, nine, ten, eleven, twelve, thirteen, fourteen or fifteen amino acid substitutions in the VH and/or the VL as long as the homologous antibodies retain or have improved functional properties when compared to the parental antibodies, such as comparable binding to TMEFF2 or improved stability. In some embodiments, the sequence identity may be about 90%, 91%, 92%, 93%, 94%, 95%, 96%, 97%, 98% or 99% to a VH or the VL amino acid sequence of the invention.

In some embodiments, the homologous anti-TMEFF2 antibodies or antigen binding fragments thereof of the invention bind to the membrane proximal region of TMEFF2 with an equilibrium dissociation constant ($K_D$) of about $0.4 \times 10^{-9}$ M or less, wherein the $K_D$ is measured using surface plasmon resonance in acetate buffer at pH 4.5-5.0 at room temperature.

In some embodiments, the homologous anti-TMEFF2 antibodies or antigen binding fragments thereof of the invention bind to the membrane proximal region of TMEFF2 with the $K_D$ of between about $0.1 \times 10^{-10}$ M and about $0.4 \times 10^{-9}$ M.

The invention also provides an isolated anti-TMEFF2 antibody or an antigen binding fragment thereof comprising the VH of SEQ ID NO: 25 and the VL of SEQ ID NO: 28, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an isolated anti-TMEFF2 antibody or an antigen binding fragment thereof comprising the VH of SEQ ID NO: 26 and the VL of SEQ ID NO: 29, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an isolated anti-TMEFF2 antibody or an antigen binding fragment thereof comprising the VH of SEQ ID NO: 27 and the VL of SEQ ID NO: 30, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an isolated anti-TMEFF2 antibody or an antigen binding fragment thereof comprising the VH of SEQ ID NO: 26 and the VL of SEQ ID NO: 31, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an isolated anti-TMEFF2 antibody or an antigen binding fragment thereof comprising the VH of SEQ ID NO: 87 and the VL of SEQ ID NO: 88, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an isolated anti-TMEFF2 antibody or an antigen binding fragment thereof comprising the VH of SEQ ID NO: 89 and the VL of SEQ ID NO: 90, wherein the VH, the VL or both the VH and the VL optionally comprise one, two, three, four, five, six, seven, eight, nine, ten, eleven, twelve, thirteen, fourteen or fifteen amino acid substitutions. Optionally, any substitutions are not within the CDRs.

The invention also provides an isolated anti-TMEFF2 antibody or an antigen-binding fragment thereof comprising the VH having the amino acid sequence at least 90%, 91%, 92%, 93%, 94%, 95%, 96%, 97%, 98% or 99% identical to the VH of SEQ ID NOs: 25, 26, 27, 87 or 89. Optionally, any variation in the sequences of the SEQ ID NOs: is not within the CDRs.

The invention also provides an isolated anti-TMEFF2 antibody or an antigen-binding fragment thereof comprising the VL having the amino acid sequence at least 90%, 91%, 92%, 93%, 94%, 95%, 96%, 97%, 98% or 99% identical to the VL of SEQ ID NOs: 28, 29, 30, 31, 88 or 90. Optionally, any variation in the sequences of the SEQ ID NOs: is not within the CDRs.

The alignment of the amino acid sequences of the VH domains of select anti-TMEFF2 antibodies is shown in FIG. 1, and the alignment of the amino acid sequences of the VL domains of select anti-TMEFF2 antibodies is shown in FIG. 2. The VH and the VL chains are identified by their SEQ ID NO: at the beginning of each row. Possible sites of substitutions in the VH and/or the VL are the residue positions that differ between the antibodies. For example, substitutions may be made at residue positions 14, 20, 54, 56, 59, 76, 82, 84, 93, 107 in the VH of SEQ ID NOs: 25, 27, 87 and 89 (numbering based on SEQ ID NO 25). Similarly, substitutions may be made at residue positions 1, 95 and 107 in the VL of SEQ ID NOs: 28, 30, 88 and 90. Exemplary substitutions that may be made are conservative amino acid substitutions, or substitutions with amino acid residues present in the corresponding residue position in each anti-TMEFF2 antibody.

The percent identity between the two sequences is a function of the number of identical positions shared by the sequences (i.e., % identity=number of identical positions/total number of positions×100), taking into account the number of gaps, and the length of each gap, which need to be introduced for optimal alignment of the two sequences.

The percent identity between two amino acid sequences may be determined using the algorithm of E. Meyers and W. Miller (*Comput Appl Biosci* 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (*J Mol Biol* 48:444-453 (1970)) algorithm which has been incorporated into the GAP program in the GCG software package (available at www.Gcg.com), using either a Blossum 62 matrix or a PAM250 matrix, and a gap weight of 16, 14, 12, 10, 8, 6, or 4 and a length weight of 1, 2, 3, 4, 5, or 6.

Antibodies with Conservative Modifications

The invention also provides an isolated anti-TMEFF2 antibody or an antigen-binding fragment thereof comprising the VH comprising the HCDR1, the HCDR2 and the HCDR3 sequences and the VL comprising the LCDR1, the LCDR2 and the LCDR3 sequences, wherein one or more of the CDR sequences comprise specified amino acid sequences based on the antibodies described herein (e.g., antibodies shown in Tables 5-12) or conservative modifications thereof, and wherein the antibodies retain the desired functional properties of the parental antibodies.

In some embodiments, the anti-TMEFF2 antibodies or antigen binding fragments thereof having conservative modifications bind to the membrane proximal region of TMEFF2 with an equilibrium dissociation constant ($K_D$) of about $0.4 \times 10^{-9}$ M or less, wherein the $K_D$ is measured using surface plasmon resonance in acetate buffer at pH 4.5-5.0 at room temperature.

In some embodiments, the anti-TMEFF2 antibodies or antigen binding fragments thereof having conservative modifications bind to the membrane proximal region of TMEFF2 with the $K_D$ of between about $0.1 \times 10^{-10}$ M and about $0.4 \times 10^{-9}$ M.

The invention also provides an isolated anti-TMEFF2 antibody or an antigen binding fragment thereof comprising a HCDR1, a HCDR2, a HCDR3, a LCDR1, a LCDR2 and a LCDR3 of SEQ ID NOs: 10, 12, 15, 18, 20 and 22, respectively, and conservative modifications thereof.

The invention also provides an isolated anti-TMEFF2 antibody or an antigen binding fragment thereof, comprising a HCDR1, a HCDR2, a HCDR3, a LCDR1, a LCDR2 and a LCDR3 of SEQ ID NOs: SEQ ID NOs: 11, 13, 16, 19, 21 and 23, respectively, and conservative modifications thereof.

The invention also provides an isolated anti-TMEFF2 antibody or an antigen binding fragment thereof, comprising a HCDR1, a HCDR2, a HCDR3, a LCDR1, a LCDR2 and a LCDR3 of SEQ ID NOs: 10, 14, 17, 18, 20 and 24, respectively, and conservative modifications thereof.

The invention also provides an isolated anti-TMEFF2 antibody or an antigen binding fragment thereof, comprising a HCDR1, a HCDR2, a HCDR3, a LCDR1, a LCDR2 and a LCDR3 of SEQ ID NOs: 11, 13, 16, 18, 20 and 22, respectively, and conservative modifications thereof.

The invention also provides an isolated anti-TMEFF2 antibody or an antigen binding fragment thereof, comprising a HCDR1, a HCDR2, a HCDR3, a LCDR1, a LCDR2 and a LCDR3 of SEQ ID NOs: 10, 12, 15, 18, 20 and 86, respectively, and conservative modifications thereof.

The invention also provides an isolated anti-TMEFF2 antibody or an antigen binding fragment thereof comprising the VH of SEQ ID NO: 25 and the VL of SEQ ID NO: 28, and conservative modifications thereof.

The invention also provides an isolated anti-TMEFF2 antibody or an antigen binding fragment thereof comprising the VH of SEQ ID NO: 26 and the VL of SEQ ID NO: 29, and conservative modifications thereof.

The invention also provides an isolated anti-TMEFF2 antibody or an antigen binding fragment thereof comprising the VH of SEQ ID NO: 27 and the VL of SEQ ID NO: 30, and conservative modifications thereof.

The invention also provides an isolated anti-TMEFF2 antibody or an antigen binding fragment thereof comprising the VH of SEQ ID NO: 26 and the VL of SEQ ID NO: 31, and conservative modifications thereof.

The invention also provides an isolated anti-TMEFF2 antibody or an antigen binding fragment thereof comprising the VH of SEQ ID NO: 87 and the VL of SEQ ID NO: 88, and conservative modifications thereof.

The invention also provides an isolated anti-TMEFF2 antibody or an antigen binding fragment thereof comprising the VH of SEQ ID NO: 89 and the VL of SEQ ID NO: 90, and conservative modifications thereof.

"Conservative modifications" refer to amino acid modifications that do not significantly affect or alter the binding characteristics of the antibody containing the amino acid modifications. Conservative modifications include amino acid substitutions, additions and deletions. Conservative amino acid substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., (1988) *Acta Physiol Scand Suppl* 643:55-67; Sasaki et al., (1988) *Adv Biophys* 35:1-24). Amino acid substitutions to the antibodies of the invention may be made by known methods for example by PCR mutagenesis (U.S. Pat. No. 4,683,195). Alternatively, libraries of variants may be generated for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

Immunoconjugates

An "immunoconjugate" refers to the antibody of the invention conjugated to one or more heterologous molecule(s).

The invention also provides an immunoconjugate comprising the isolated antibody of the invention or the antigen binding fragment thereof conjugated to a heterologous molecule.

In some embodiments, the heterologous molecule is a detectable label.

The isolated antibody or the antigen-binding fragment thereof of the invention conjugated to a detectable label may be used to evaluate expression of TMEFF2 on a variety of samples. Detectable label includes compositions that when conjugated to the isolated antibody or the antigen binding fragment thereof of the invention renders the latter detectable, via spectroscopic, photochemical, biochemical, immunochemical, or chemical means.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal after being stimulated by an external field.

Exemplary radioactive isotopes may be γ-emitting, Auger-emitting, β-emitting, alpha-emitting or positron-emitting radioactive isotope. Exemplary radioactive isotopes include $^{3}H$, $^{11}C$, $^{13}C$, $^{15}N$, $^{18}F$, $^{19}F$, $^{55}CO$, $^{57}CO$, $^{60}CO$, $^{61}Cu$, $^{62}Cu$, $^{64}Cu$, $^{67}Cu$, $^{68}Ga$, $^{72}As$, $^{75}Br$, $^{86}Y$, $^{89}Zr$, $^{90}Sr$, $^{94}mTc$, $^{99}mTc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, *neptunium* atoms, plutonium atoms, americium atoms, curium atoms, berkelium atoms, californium atoms, einsteinium atoms, fermium atoms, mendelevium atoms, nobelium atoms, or lawrencium atoms.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The isolated antibody or the antigen binding fragment thereof of the invention conjugated to a detectable label may be used as an imaging agent.

The isolated antibody or the antigen binding fragment thereof of the invention may be conjugated to a detectable label using known methods.

In some embodiments, the detectable label is complexed with a chelating agent.

In some embodiments, the detectable label is conjugated to the antibody or the antigen binding fragment thereof of the invention via a linker.

The detectable label may be linked directly, or indirectly, to the antibody or the antigen binding fragment thereof of the invention using known methods. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

Bispecific Anti-TMEFF2/Anti-CD3 Antibodies

The invention also provides an isolated bispecific anti-TMEFF2/anti-CD3 antibody or an antigen binding fragment thereof comprising a first domain that binds TMEFF2 and a second domain that binds CD3.

The invention also provides an isolated bispecific anti-TMEFF2/anti-CD3 antibody or an antigen binding fragment thereof comprising a first domain that binds TMEFF2 and a second domain that binds CD3, wherein the antibody binds to the membrane proximal region of TMEFF2. While not wishing to be bound by any particular theory, bispecific antibodies binding to the membrane proximal region of TMEFF2 may be more efficient in mediating T-cell mediated killing of tumor cells.

The invention also provides an isolated bispecific anti-TMEFF2/anti-CD3 antibody or an antigen binding fragment thereof comprising a first domain that binds TMEFF2 and a second domain that binds CD3, wherein the antibody competes for binding to the membrane proximal region of TMEFF2 with a reference antibody comprising a heavy chain variable region (VH) of SEQ ID NO: 25 and a light chain variable region (VL) of SEQ ID NO: 28, the VH of SEQ ID NO: 26 and the VL of SEQ ID NO: 29, the VH of SEQ ID NO: 27 and the VL of SEQ ID NO: 30, the VH of SEQ ID NO: 26 and the VL of SEQ ID NO: 31, the VH of SEQ ID NO: 87 and the VL of SEQ ID NO: 88, or the VH of SEQ ID NO: 89 and the VL of SEQ ID NO: 90.

In some embodiments, the isolated bispecific anti-TMEFF2/anti-CD3 antibody or an antigen binding fragment thereof binds the membrane proximal region of TMEFF2 with a dissociation constant ($K_D$) of about $0.4 \times 10^{-9}$ M or less, wherein the $K_D$ is measured using surface plasmon resonance in acetate buffer at pH 4.5-5.0 at room temperature.

In some embodiments, the isolated bispecific anti-TMEFF2/anti-CD3 antibody or the antigen binding fragment thereof binds the membrane proximal region TMEFF2 with the $K_D$ of between about $0.1 \times 10^{-10}$ M and about $0.4 \times 10^{-9}$ M.

The invention also provides an isolated bispecific anti-TMEFF2/anti-CD3 antibody or an antigen binding fragment thereof, wherein the first domain comprises a HCDR1, a HCDR2, a HCDR3, a LCDR1, a LCDR2 and a LCDR3 of
SEQ ID NOs: 10, 12, 15, 18, 20 and 22, respectively;
SEQ ID NOs: 11, 13, 16, 19, 21 and 23, respectively;
SEQ ID NOs: 10, 14, 17, 18, 20 and 24, respectively; or
SEQ ID NOs: 11, 13, 16, 18, 20 and 22, respectively; or
SEQ ID NOs: 10, 12, 15, 18, 20 and 86, respectively.

The invention also provides an isolated bispecific anti-TMEFF2/anti-CD3 antibody or an antigen binding fragment thereof, wherein the second domain comprises the HCDR1, the HCDR2, the HCDR3, the LCDR1, the LCDR2 and the LCDR3 of
SEQ ID NOs: 60, 61, 62, 63, 64 and 65, respectively; or
SEQ ID NOs: 68, 69, 70, 71, 72 and 73 respectively.

The invention also provides an isolated bispecific anti-TMEFF2/anti-CD3 antibody or an antigen binding fragment thereof, wherein the first domain comprises
the VH of SEQ ID NO: 25 and the VL of SEQ ID NO: 28;
the VH of SEQ ID NO: 26 and the VL of SEQ ID NO: 29;
the VH of SEQ ID NO: 27 and the VL of SEQ ID NO: 30;
the VH of SEQ ID NO: 26 and the VL of SEQ ID NO: 31;
the VH of SEQ ID NO: 87 and the VL of SEQ ID NO: 88; or
the VH of SEQ ID NO: 89 and the VL of SEQ ID NO: 90.

The invention also provides an isolated bispecific anti-TMEFF2/anti-CD3 antibody or an antigen binding fragment thereof, wherein the second domain comprises
the VH of SEQ ID NO: 66 and the VL of SEQ ID NO: 67; or
the VH of SEQ ID NO: 74 and the VL of SEQ ID NO: 75.

In some embodiments, the second domain comprises the VH of SEQ ID NO: 59 and the VL of SEQ ID NO: 111.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 10, 12, 15, 18, 20 and 22, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
the first domain comprises a VH of SEQ ID NO: 25 and a VL of SEQ ID NO: 28, and the second domain comprises the VH of SEQ ID NO: 66 and the VL of SEQ ID NO: 67; and/or
the bispecific anti-TMEFF2/anti-CD3 antibody or the antigen binding fragment thereof comprises a first heavy chain (HC1) of SEQ ID NO: 32, a first light chain (LC1) of SEQ ID NO: 35, a second heavy chain (HC2) of SEQ ID NO: 76 and a second light chain (LC2) of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 10, 12, 15, 18, 20 and 22, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
the first domain comprises a VH of SEQ ID NO: 25 and a VL of SEQ ID NO: 28, and the second domain comprises the VH of SEQ ID NO: 74 and the VL of SEQ ID NO: 75; and/or
the bispecific anti-TMEFF2/anti-CD3 antibody or the antigen binding fragment thereof comprises a HC1 of SEQ ID NO: 32, a LC1 of SEQ ID NO: 35, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 11, 13, 16, 19, 21, and 23, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
the first domain comprises a VH of SEQ ID NO: 26 and a VL of SEQ ID NO: 29, and the second domain comprises the VH of SEQ ID NO: 66 and the VL of SEQ ID NO:67; and/or
the bispecific anti-TMEFF2/anti-CD3 antibody or the antigen binding fragment thereof comprises a HC1 of SEQ ID NO: 33, a LC1 of SEQ ID NO: 36, a HC2 of SEQ ID NO: 76 and a LC2 of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 11, 13, 16, 19, 21, and 23, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
the first domain comprises a VH of SEQ ID NO: 26 and a VL of SEQ ID NO: 29, and the second domain comprises the VH of SEQ ID NO: 74 and the VL of SEQ ID NO:75; and/or the bispecific anti-TMEFF2/anti-CD3 antibody or the antigen binding fragment thereof comprises a HC1 of SEQ ID NO: 33, a LC1 of SEQ ID NO: 36, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 10, 14, 17, 18, 20 and 24, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
the first domain comprises a VH of SEQ ID NO: 27 and a VL of SEQ ID NO: 30, and the second domain comprises the VH of SEQ ID NO: 66 and the VL of SEQ ID NO:67; and/or
the bispecific anti-TMEFF2/anti-CD3 antibody or the antigen binding fragment thereof comprises a HC1 of SEQ ID NO: 34, a LC1 of SEQ ID NO: 37, a HC2 of SEQ ID NO: 76 and a LC2 of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 10, 14, 17, 18, 20 and 24, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
the first domain comprises a VH of SEQ ID NO: 27 and a VL of SEQ ID NO: 30, and the second domain comprises the VH of SEQ ID NO: 74 and the VL of SEQ ID NO:75; and/or
the bispecific anti-TMEFF2/anti-CD3 antibody or the antigen binding fragment thereof comprises a HC1 of SEQ ID NO: 34, a LC1 of SEQ ID NO: 37, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 11, 13, 16, 18, 20 and 22, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
the first domain comprises a VH of SEQ ID NO: 26 and a VL of SEQ ID NO: 31, and the second domain comprises the VH of SEQ ID NO: 66 and the VL of SEQ ID NO:67; and/or
the bispecific anti-TMEFF2/anti-CD3 antibody or the antigen binding fragment thereof comprises a HC1 of SEQ ID NO: 33, a LC1 of SEQ ID NO: 38, a HC2 of SEQ ID NO: 76 and a LC2 of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 11, 13, 16, 18, 20 and 22, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
the first domain comprises a VH of SEQ ID NO: 26 and a VL of SEQ ID NO: 31, and the second domain comprises the VH of SEQ ID NO: 74 and the VL of SEQ ID NO: 75; and/or
the bispecific anti-TMEFF2/anti-CD3 antibody or the antigen binding fragment thereof comprises a HC1 of SEQ ID NO: 33, a LC1 of SEQ ID NO: 38, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
the first domain comprises a VH of SEQ ID NO: 87 and a VL of SEQ ID NO: 88, and the second domain comprises the VH of SEQ ID NO: 66 and the VL of SEQ ID NO: 67; and/or
the bispecific anti-TMEFF2/anti-CD3 antibody or the antigen binding fragment thereof comprises a first heavy chain (HC1) of SEQ ID NO: 91, a first light chain (LC1) of SEQ ID NO: 92, a second heavy chain (HC2) of SEQ ID NO: 76 and a second light chain (LC2) of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
the first domain comprises a VH of SEQ ID NO: 87 and a VL of SEQ ID NO: 88, and the second domain comprises the VH of SEQ ID NO: 74 and the VL of SEQ ID NO: 75; and/or
the bispecific anti-TMEFF2/anti-CD3 antibody or the antigen binding fragment thereof comprises a HC1 of SEQ ID NO: 91, a LC1 of SEQ ID NO: 92, a HC2 of SEQ ID NO: 78 and a LC2 of SEQ ID NO: 79.

The invention also provides an isolated bispecific anti-TMEFF2/anti-CD3 antibody or an antigen binding fragment thereof comprising a first domain that binds TMEFF2 and a second domain that binds CD3, wherein
the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
the first domain comprises a VH of SEQ ID NO: 89 and a VL of SEQ ID NO: 90, and the second domain comprises the VH of SEQ ID NO: 66 and the VL of SEQ ID NO: 67; and/or
the bispecific anti-TMEFF2/anti-CD3 antibody or the antigen binding fragment thereof comprises a first heavy chain (HC1) of SEQ ID NO: 93, a first light chain (LC1) of SEQ ID NO: 94, a second heavy chain (HC2) of SEQ ID NO: 76 and a second light chain (LC2) of SEQ ID NO: 77.

The invention also provides an isolated bispecific anti-TMEFF2/anti-CD3 antibody or an antigen binding fragment thereof comprising a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;

the first domain comprises a VH of SEQ ID NO: 89 and a VL of SEQ ID NO: 90, and the second domain comprises the VH of SEQ ID NO: 74 and the VL of SEQ ID NO: 75; and/or the bispecific anti-TMEFF2/anti-CD3 antibody or an antigen binding fragment thereof comprises a HC1 of SEQ ID NO: 93, a LC1 of SEQ ID NO: 94, a HC2 of SEQ ID NO: 78 and a LC2 of SEQ ID NO: 79.

Engineered and Modified Antibodies

The antibodies or the antigen binding fragments thereof of the invention may be further engineered to generate modified antibodies with similar or altered properties when compared to the parental antibodies. The VH, the VL, the VH and the VL, the constant regions, the heavy chain framework, the light chain framework, or any or all of the six CDRs may be engineered in the antibodies of the invention.

The antibodies of the invention may be engineered by CDR grafting. One or more CDR sequences of the antibodies of the invention may be grafted to a different framework sequence. CDR grafting may be done using known methods and methods described herein.

The framework sequences that may be used may be obtained from public DNA databases or published references that include germline antibody gene sequences. For example, germline DNA and the encoded protein sequences for human heavy and light chain variable domain genes may be found at IMGT®, the international ImMunoGeneTics information System® www.Imgt.org. Framework sequences that may be used to replace the existing framework sequences of the antibodies of the invention may be those that show the highest percent (%) identity to the parental variable domains over the entire length of the VH or the VL, or over the length of the FR1, FR2, FR3 and FR4. In addition, suitable frameworks may further be selected based on the VH and the VL CDR1 and CDR2 lengths or identical LCDR1, LCDR2, LCDR3, HCDR1 and HCDR2 canonical structure. Suitable frameworks may be selected using known methods, such as human framework adaptation described in U.S. Pat. No. 8,748,356 or superhumanization described in U.S. Pat. No. 7,709,226.

The framework sequences of the parental and engineered antibodies may further be modified, for example by back-mutations to restore and/or improve binding of the generated antibodies to the antigen as described for example in U.S. Pat. No. 6,180,370. The framework sequences of the parental or engineered antibodies may further be modified by mutating one or more residues within the framework region (or alternatively within one or more CDR regions) to remove T-cell epitopes to thereby reduce the potential immunogenicity of the antibody. This approach is also referred to as "deimmunization" and described in further detail in U.S. Patent Publ. No. US20070014796.

The CDR residues of the antibodies of the invention may be mutated to modulate affinity of the antibodies to TMEFF2 and/or CD3.

The CDR residues of the antibodies of the invention may be mutated to minimize risk of post-translational modifications. Amino acid residues of putative motifs for deamination (NS), acid-catalyzed hydrolysis (DP), isomerization (DS), or oxidation (W) may be substituted with any of the naturally occurring amino acids to mutagenize the motifs, and the resulting antibodies may be tested for their functionality and stability using methods described herein.

Antibodies of the invention modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., (2001) *J Mol Biol* 305:989-1010). Potential structure destabilizing residues may be identified based upon the crystal structure of the antibody or by molecular modeling in certain cases, and the effect of the residues on antibody stability may be tested by generating and evaluating variants harboring mutations in the identified residues. One of the ways to increase antibody stability is to raise the thermal transition midpoint ($T_m$) as measured by differential scanning calorimetry (DSC). In general, the protein Tm is correlated with its stability and inversely correlated with its susceptibility to unfolding and denaturation in solution and the degradation processes that depend on the tendency of the protein to unfold (Remmele et al., (2000) *Biopharm* 13:36-46). A number of studies have found correlation between the ranking of the physical stability of formulations measured as thermal stability by DSC and physical stability measured by other methods (Gupta et al., (2003) *AAPS PharmSci* 5E8; Zhang et al., (2004) *J Pharm Sci* 93:3076-89; Maa et al., (1996) *Int J Pharm* 140:155-68; Bedu-Addo et al., (2004) *Pharm Res* 21:1353-61; Remmele et al., (1997) *Pharm Res* 15:200-8). Formulation studies suggest that a Fab Tm has implication for long-term physical stability of a corresponding mAb.

C-terminal lysine (CTL) may be removed from injected antibodies by endogenous circulating carboxypeptidases in the blood stream (Cai et al., (2011) *Biotechnol Bioeng* 108:404-412). During manufacturing, CTL removal may be controlled to less than the maximum level by control of concentration of extracellular $Zn^{2+}$, EDTA or EDTA-$Fe^{3+}$ as described in U.S. Patent Publ. No. US20140273092. CTL content in antibodies may be measured using known methods.

Fc substitutions may be made to the antibodies of the invention to modulate antibody effector functions and/or pharmacokinetic properties. In traditional immune function, the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on cells. The diversity of cellular responses triggered by antibodies and immune complexes results from the heterogeneity of the Fc receptors: FcγRI (CD64), FcγRIIa (CD32A), and FcγRIII (CD16) are activating Fcγ receptors (i e, immune system enhancing) whereas FcγRIIb (CD32B) is an inhibitory Fcγ receptor (i.e., immune system dampening). Binding to the FcRn receptor modulates antibody half-life.

In some embodiments, the anti-TMEFF2 antibodies or the bispecific anti-TMEFF2/anti-CD3 antibodies of the invention comprise at least one substitution in an Fc region.

In some embodiments, the anti-TMEFF2 antibodies or the bispecific anti-TMEFF2/anti-CD3 antibodies of the invention comprise one, two, three, four, five, six, seven, eight, nine, ten, eleven, twelve, thirteen, fourteen or fifteen substitutions in the Fc region.

Fc positions that may be substituted to modulate antibody half-life. Exemplary singular or combination substitutions that may be made to increase the half-life of the antibody are substitutions M428L/N434S, M252Y/S254T/T256E, T250Q/M428L, N434A and T307A/E380A/N434A. Exemplary singular or combination substitutions that may be made to reduce the half-life of the antibody are substitutions H435A, P257I/N434H, D376V/N434H, M252Y/S254T/T256E/H433K/N434F, T308P/N434A and H435R.

In some embodiments, the anti-TMEFF2 antibodies or the bispecific anti-TMEFF2/anti-CD3 antibodies of the invention comprise at least one substitution in the Fc region selected from the group consisting of M428L/N434S, M252Y/S254T/T256E, T250Q/M428L, N434A, T307A/E380A/N434A, H435A, P257I/N434H, D376V/N434H, M252Y/S254T/T256E/H433K/N434F, T308P/N434A and H435R.

In some embodiments, the anti-TMEFF2 antibodies or the bispecific anti-TMEFF2/anti-CD3 antibodies of the invention comprise at least one substitution in the Fc region that reduces binding of the antibody to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be substituted to reduce binding of the antibody to the activating FcγR and subsequently to reduce effector function are substitutions L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331 S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4.

Well-known S228P substitution may be made in IgG4 antibodies to enhance IgG4 stability.

In some embodiments, the anti-TMEFF2 antibodies or the bispecific anti-TMEFF2/anti-CD3 antibodies of the invention comprise a S228P substitution, wherein residue numbering is according to the EU Index.

In some embodiments, the anti-TMEFF2 antibodies or the bispecific anti-TMEFF2/anti-CD3 antibodies of the invention comprise a F234A, a L235A or a F234A/L235A substitution, wherein residue numbering is according to the EU Index.

In some embodiments, the anti-TMEFF2 antibodies or the bispecific anti-TMEFF2/anti-CD3 antibodies of the invention comprise a S228P, a F234A and a L235A substitution, wherein residue numbering is according to the EU Index.

Methods of Generating Homologous Antibodies, Antibodies with Conservative Modifications, and Engineered and Modified Antibodies The antibodies of the invention that have altered amino acid sequences when compared to the parental antibodies may be generated using standard cloning and expression technologies. For example, site-directed mutagenesis or PCR-mediated mutagenesis may be performed to introduce the mutation(s) and the effect on antibody binding or other property of interest may be evaluated using well known methods and the methods described herein in the Examples.

Antibody Isotypes and Allotypes

The anti-TMEFF2 antibodies or the bispecific anti-TMEFF2/anti-CD3 antibodies of the invention may be an IgG1, an IgG2, an IgG3 or an IgG4 isotype.

In some embodiments, the anti-TMEFF2 antibodies or the bispecific anti-TMEFF2/anti-CD3 antibodies of the invention are an IgG1 isotype.

In some embodiments, the anti-TMEFF2 antibodies or the bispecific anti-TMEFF2/anti-CD3 antibodies of the invention are an IgG2 isotype.

In some embodiments, the anti-TMEFF2 antibodies or the bispecific anti-TMEFF2/anti-CD3 antibodies of the invention are an IgG3 isotype.

In some embodiments, the anti-TMEFF2 antibodies or the bispecific anti-TMEFF2/anti-CD3 antibodies of the invention are of IgG4 isotype.

Immunogenicity of therapeutic antibodies is associated with increased risk of infusion reactions and decreased duration of therapeutic response (Baert et al., (2003) *N Engl J Med* 348:602-08). The extent to which therapeutic antibodies induce an immune response in the host may be determined in part by the allotype of the antibody (Stickler et al., (2011) *Genes and Immunity* 12:213-21). Antibody allotype is related to amino acid sequence variations at specific locations in the constant region sequences of the antibody. Table 2 shows select IgG1, IgG2 and IgG4 allotypes.

In some embodiments, the anti-TMEFF2 antibodies or the bispecific anti-TMEFF2/anti-CD3 antibodies of the invention are an G2m(n) allotype.

In some embodiments, the anti-TMEFF2 antibodies or the bispecific anti-TMEFF2/anti-CD3 antibodies of the invention are an G2m(n-) allotype.

In some embodiments, the anti-TMEFF2 antibodies or the bispecific anti-TMEFF2/anti-CD3 antibodies invention are an G2m(n)/(n-) allotype.

In some embodiments, the anti-TMEFF2 antibodies or the bispecific anti-TMEFF2/anti-CD3 antibodies of the invention are an nG4m(a) allotype.

In some embodiments, the anti-TMEFF2 antibodies or the bispecific anti-TMEFF2/anti-CD3 antibodies of the invention are an G1m(17) allotype.

In some embodiments, the anti-TMEFF2 antibodies or the bispecific anti-TMEFF2/anti-CD3 antibodies of the invention are an G1m(17,1) allotype.

TABLE 2

| | Amino acid residue at position of diversity (residue numbering: EU Index) | | | | | | |
|---|---|---|---|---|---|---|---|
| | IgG2 | | IgG4 | | IgG1 | | |
| Allotype | 189 | 282 | 309 | 422 | 214 | 356 | 358 | 431 |
| G2m(n) | T | M | | | | | | |
| G2m(n-) | P | V | | | | | | |

TABLE 2-continued

| | Amino acid residue at position of diversity (residue numbering: EU Index) | | | | | | | |
|---|---|---|---|---|---|---|---|---|
| | IgG2 | | IgG4 | | IgG1 | | | |
| Allotype | 189 | 282 | 309 | 422 | 214 | 356 | 358 | 431 |
| G2m(n)/(n-) | T | V | | | | | | |
| nG4m(a) | | | L | R | | | | |
| G1m(17) | | | | | K | E | M | A |
| G1m(17,1) | | | | | K | D | L | A |

Anti-Idiotypic Antibodies

The invention also provides an anti-idiotypic antibody specifically binding to the anti-TMEFF2 antibody or the bispecific anti-TMEFF2/anti-CD3 antibody of the invention.

The invention also provides an anti-idiotypic antibody specifically binding to the anti-TMEFF2 antibody of the invention comprising the VH of SEQ ID NO: 25 and the VL of SEQ ID NO:

The invention also provides an anti-idiotypic antibody specifically binding to the anti-TMEFF2 antibody of the invention comprising the VH of SEQ ID NO: 26 and the VL of SEQ ID NO: 29.

The invention also provides an anti-idiotypic antibody specifically binding to the anti-TMEFF2 antibody of the invention comprising the VH of SEQ ID NO: 27 and the VL of SEQ ID NO: 30.

The invention also provides an anti-idiotypic antibody specifically binding to the anti-TMEFF2 antibody of the invention comprising the VH of SEQ ID NO: 26 and the VL of SEQ ID NO: 31.

The invention also provides an anti-idiotypic antibody specifically binding to the anti-TMEFF2 antibody of the invention comprising the VH of SEQ ID NO: 87 and the VL of SEQ ID NO: 88.

The invention also provides an anti-idiotypic antibody specifically binding to the anti-TMEFF2 antibody of the invention comprising the VH of SEQ ID NO: 89 and the VL of SEQ ID NO: 90.

An anti-idiotypic (Id) antibody is an antibody which recognizes the antigenic determinants (e.g. the paratope or CDRs) of the antibody. The Id antibody may be antigen-blocking or non-blocking. The antigen-blocking Id may be used to detect the free antibody in a sample (e.g. anti-TMEFF2 antibody of the invention described herein). The non-blocking Id may be used to detect the total antibody (free, partially bond to antigen, or fully bound to antigen) in a sample. An Id antibody may be prepared by immunizing an animal with the antibody to which an anti-Id is being prepared.

An anti-Id antibody may also be used as an immunogen to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein.

Generation of Monospecific Antibodies of the Invention

In some embodiments, the anti-TMEFF2 antibodies are human.

In some embodiments, the anti-TMEFF2 antibodies are humanized.

Monospecific antibodies of the invention may be generated using various technologies. For example, the hybridoma method of Kohler and Milstein, Nature 256:495, 1975 may be used to generate monoclonal antibodies. In the hybridoma method, a mouse or other host animal, such as a hamster, rat or monkey, is immunized with human, chimpanzee or macaque TMEFF2 or fragments of TMEFF2, such as the membrane proximal domain of TMEFF2 followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding, cross-reactivity or lack thereof, and affinity for the antigen.

Various host animals may be used to produce the anti-TMEFF2 antibodies of the invention. For example, Balb/c mice may be used to generate mouse anti-human TMEFF2 antibodies. The antibodies made in Balb/c mice and other non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), Resurfacing (Padlan, (1991) Mol Immunol 28:489-499), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or a combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice, rat or chicken carrying human immunoglobulin (Ig) loci in their genome may be used to generate human antibodies against a target protein, and are described in for example U.S. Pat. No. 6,150,584, Int. Patent Publ. No. WO99/45962, Int. Patent Publ. Nos. WO2002/066630, WO2002/43478, WO2002/043478 and 401990/04036, Lonberg et al (1994) Nature 368:856-9; Green et al (1994) Nature Genet. 7:13-21; Green & Jakobovits (1998) Exp. Med. 188:483-95; Lonberg and Huszar (1995) Int Rev Immunol 13:65-93; Bruggemann et al., (1991) Eur J Immunol 21:1323-1326; Fishwild et al., (1996) Nat Biotechnol 14:845-851; Mendez et al., (1997) Nat Genet 15:146-156; Green (1999) J Immunol Methods 231:11-23; Yang et al., (1999) Cancer Res 59:1236-1243; Brüggemann and Taussig (1997) Curr Opin Biotechnol 8:455-458. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (www_Regeneron_com). Harbour Antibodies (www_Harbourantibodies_com). Open Monoclonal Technology, Inc. (OMT) (www_Omtinc_net), KyMab (www_Kymab_com), Trianni (www_Trianni_com) and Ablexis (www_Ablexis_com)

may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), or unpaired or paired antibody variable regions (Knappik et al., (2000) J Mol Biol 296:57-86; Krebs et al., (2001) J Immunol Meth 254:67-84; Vaughan et al., (1996) Nature Biotechnology 14:309-314; Sheets et al., (1998) PITAS (USA) 95:6157-6162; Hoogenboom and Winter (1991) J Mol Biol 227:381; Marks et al., (1991) J Mol Biol 222:581). The antibodies of the invention may be isolated for example from phage display library expressing antibody heavy and light chain variable regions as fusion proteins with bacteriophage pIX coat protein as described in Shi et al., (2010) J Mol Biol 397:385-96, and Int. Patent Publ. No. WO009/085462). The libraries may be screened for phage binding to human and/or cyno TMEFF2 or CD3 and the obtained positive clones may be further characterized, the Fabs isolated from the clone lysates, and expressed as full length IgGs. Such phage display methods for isolating human antibodies are described in for example: U.S. Pat. Nos. 5,223,409, 5,403,484, 5,571,698, 5,427,908, 5,580,717, 5,969,108, 6,172,197, 5,885,793; 6,521,404; 6,544,731; 6,555,313; 6,582,915 and 6,593,081.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Generation of Bispecific Anti-TMEFF2/Anti-CD3 Antibodies of the Invention

The bispecific anti-TMEFF2/anti-CD3 antibodies of the invention may be generated by combining TMEFF2 binding VH/VL domains isolated herein with any CD3 binding VH/VL domains, including those described herein and those that are publicly available. Exemplary CD3 binding VH/VL domains that may be used are those of the antibodies CD3B219 and CD3B376 as described herein. Exemplary TMEFF2 binding VH/VL domains that may be used are those of antibodies TMEB675, TMEB570, TMEB674, TMEB565, TMEB762 and TMEB757. The generated bispecific anti-TMEFF2/anti-CD3 antibodies may be tested for their binding to TMEFF2 and CD3, and for their desired functional characteristics, such as T-cell mediated killing of TMEFF2-expressing cells (eg, LNCaP).

Bispecific antibodies of the invention may be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy chain disulfide bonds in the hinge regions of the parental monospecific antibodies are reduced. The resulting free cysteines of one of the parental monospecific antibodies form an inter heavy-chain disulfide bond with cysteine residues of a second parental monospecific antibody molecule and simultaneously CH3 domains of the parental antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on TMEFF2 and an epitope on CD3. For example, the bispecific antibodies of the invention may be generated using the DuoBody® Technology described in Int.Patent Publ. No. WO2011/131746. Mutations F405L in one heavy chain and K409R in the other heavy chain may be used in case of IgG1 antibodies. For IgG2 antibodies, a wild-type IgG2 and a IgG2 antibody with F405L and R409K substitutions may be used. For IgG4 antibodies, a wild-type IgG4 and a IgG4 antibody with F405L and R409K substitutions may be used. To generate bispecific antibodies, first monospecific bivalent antibody and the second monospecific bivalent antibody are engineered to have the aforementioned mutation in the Fc region, the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

In some embodiments, the bispecific anti-TMEFF2/anti-CD3 antibody is an IgG1 isotype and comprises a F405L substitution in a first heavy chain (HC1) and a K409R substitution in a second heavy chain (HC2) when compared to the wild-type IgG1 of SEQ ID NO: 84.

In some embodiments, the bispecific anti-TMEFF2/anti-CD3 antibody is an IgG4 isotype and comprises a F405L/R409K substitution in the HC2, when compared to the wild-type IgG4 of SEQ ID NO: 85.

In some embodiments, the bispecific anti-TMEFF2/anti-CD3 antibody is an IgG4 isotype and comprises S228P, F234A and L235A substitutions in the HC1 and S228P, F234A, L235A, F405L and R409K substitutions in the HC2 when compared to the wild-type IgG4 of SEQ ID NO: 85.

SEQ ID NO: 84 wild-type IgG1
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

SEQ ID NO: 85 wild-type IgG4
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

```
SEQ ID NO 103: IgG1 F405L
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFLLYSKLTVDKSRW

QQGNVFSCSVMHEALHNHYTQKSLSLSPGK

SEQ ID NO: 109: IgG1 K409R
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSRLTVDKSRW

QQGNVFSCSVMHEALHNHYTQKSLSLSPGK

SEQ ID NO: 104 IgG4 F405L/R409K
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFLLYSKLTVDKSRWQEG

NVFSCSVMHEALHNHYTQKSLSLSLGK
```

Bispecific antibodies may also be generated using designs such as the Knob-in-Hole (Genentech), CrossMAbs (Roche) and the electrostatically-matched (Chugai, Amgen, NovoNordisk, Oncomed), the LUZ-Y (Genentech), the Strand Exchange Engineered Domain body (SEEDbody) (EMD Serono), and the Biclonic (Merus).

In the "knob-in-hole" strategy (see, e.g., Intl. Publ. No. WO 2006/028936) select amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366S/T394S, F405W/T394S and T366W/T366S_L368A_Y407V.

CrossMAb technology, in addition to utilizing the "knob-in-hole" strategy to promoter Fab arm exchange utilizes CH1/CL domain swaps in one half arm to ensure correct light chain pairing of the resulting bispecific antibody (see e.g. U.S. Pat. No. 8,242,247).

Other cross-over strategies may be used to generate full length bispecific antibodies of the invention by exchanging variable or constant, or both domains between the heavy chain and the light chain or within the heavy chain in the bispecific antibodies, either in one or both arms. These exchanges include for example VH-CH1 with VL-CL, VH with VL, CH3 with CL and CH3 with CH1 as described in Int. Patent Publ. Nos. WO2009/080254, WO2009/080251, WO2009/018386 and WO2009/080252.

Other strategies such as promoting heavy chain heterodimerization using electrostatic interactions by substituting positively charged residues at one CH3 surface and negatively charged residues at a second CH3 surface may be used, as described in US Patent Publ. No. US2010/0015133; US Patent Publ. No. US2009/0182127; US Patent Publ. No. US2010/028637 or US Patent Publ. No. US2011/0123532. In other strategies, heterodimerization may be promoted by following substitutions (expressed as modified positions in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Patent Publ. No. US2012/0149876 or U.S. Patent Publ. No. US2013/0195849.

SEEDbody technology may be utilized to generate bispecific antibodies of the invention. SEEDbodies have, in their constant domains, select IgG residues substituted with IgA residues to promote heterodimerization as described in U.S. Patent No. US20070287170.

Mutations are typically made at the DNA level to a molecule such as the constant domain of the antibody using standard methods.

Polynucleotides, Vectors and Host Cells

The invention also provides isolated polynucleotides that encode the anti-TMEFF2 antibodies or the antigen-binding fragments thereof of the invention. The invention also provides isolated polynucleotides that encode the bispecific anti-TMEFF2/anti-CD3 antibodies or the antigen-binding fragments thereof of the invention. The isolated polynucleotides capable of encoding the variable domain segments provided herein may be included on the same, or different, vectors to produce antibodies or antigen-binding fragments. The polynucleotide may be a complementary deoxynucleic acid (cDNA) and may be codon optimized for expression in suitable host. Codon optimization is a well-known technology.

In some embodiments, the polynucleotides described herein (and the peptides they encode) include a leader sequence. Any leader sequence known in the art may be employed. The leader sequence may include, a restriction site or a translation start site.

The invention also provides an isolated polynucleotide encoding the VH of the antibody of the invention, the VL of the antibody of the invention, the heavy chain of the antibody of the invention or the light chain of the antibody of the invention.

The invention also provides an isolated polynucleotide encoding the VH of SEQ ID NOs: 25, 26, 27, 87 or 89.

The invention also provides an isolated polynucleotide encoding the VL of SEQ ID NOs: 28, 29, 30, 31, 88 or 90.

The invention also provides an isolated polynucleotide encoding the HC1, the LC1, the HC2 or the LC2 of the anti-TMEFF2/anti-CD3 antibodies of the invention.

The invention also provides an isolated polynucleotide encoding the HC1 of SEQ ID NOs: 32, 33, 34, 91 or 93.

The invention also provides an isolated polynucleotide encoding the LC1 of SEQ ID NOs: 35, 36, 37, 38, 92 or 94.

The invention also provides an isolated polynucleotide encoding the HC2 of SEQ ID NOs: 76 or 78.

The invention also provides an isolated polynucleotide encoding the LC2 of SEQ ID NOs:77 or 79.

The invention also provides an isolated polynucleotide comprising the polynucleotide sequence of SEQ ID NOs: 39, 40, 41, 42, 43, 44, 45, 46, 47, 48, 49, 50, 51, 52, 95, 96, 97, 98, 99, 100, 101, or 102.

The invention also provides an isolated polynucleotide comprising the polynucleotide sequence of SEQ ID NOs: 105, 106, 80, 81, 107, 108, 82 and 83.

The polynucleotide sequences encoding the VH or the VL or an antigen binding fragment thereof of the antibodies of the invention, or the heavy chain and the light chain of the antibodies of the invention may be operably linked to one or more regulatory elements, such as a promoter or enhancer, that allow expression of the nucleotide sequence in the intended host cell. The polynucleotide may be a cDNA.

The invention also provides a vector comprising the polynucleotide of the invention. Such vectors may be plasmid vectors, viral vectors, vectors for baculovirus expression, transposon based vectors or any other vector suitable for introduction of the synthetic polynucleotide of the invention into a given organism or genetic background by any means. For example, polynucleotides encoding light and/or heavy chain variable regions of the antibodies of the invention, optionally linked to constant regions, are inserted into expression vectors. The light and/or heavy chains may be cloned in the same or different expression vector. The DNA segments encoding immunoglobulin chains may be operably linked to control sequences in the expression vector(s) that ensure the expression of immunoglobulin polypeptides. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides Recombinant expression vectors within the scope of the description include synthetic or cDNA-derived nucleic acid fragments that encode at least one recombinant protein such as a VH, a VL, a HC or a LC of an antibody, which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the anti-TMEFF2 antibody or the antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments, the vector system will include one or more polyadenylation sites (e.g., SV40), which may be upstream or downstream of any of the aforementioned nucleic acid sequences. Vector components may be contiguously linked or arranged in a manner that provides optimal spacing for expressing the gene products (i.e., by the introduction of "spacer" nucleotides between the ORFs) or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamine synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

Exemplary vectors that may be used are Bacterial: pBs, phagescript, PsiX 174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWL-neo, pSV2cat, pOG44, PXR1, pSG (Stratagene) pSVK3, pBPV, pMSG and pSVL (Pharmacia), pEE6.4 (Lonza) and pEE12.4 (Lonza).

In some embodiments, the vector comprises a polynucleotide encoding the VH of SEQ ID NO: 25 and/or the VL of SEQ ID NO: 28.

In some embodiments, the vector comprises the polynucleotide of SEQ ID NO: 39 and/or the polynucleotide of SEQ ID NO: 42.

In some embodiments, the vector comprises a polynucleotide encoding the VH of SEQ ID NO: 26 and/or the VL of SEQ ID NO: 29.

In some embodiments, the vector comprises the polynucleotide of SEQ ID NO: 40 and/or the polynucleotide of SEQ ID NO: 43.

In some embodiments, the vector comprises a polynucleotide encoding the VH of SEQ ID NO: 27 and/or the VL of SEQ ID NO: 30.

In some embodiments, the vector comprises the polynucleotide of SEQ ID NO: 41 and/or the polynucleotide of SEQ ID NO: 44.

In some embodiments, the vector comprises a polynucleotide encoding the VH of SEQ ID NO: 26 and/or the VL of SEQ ID NO: 31.

In some embodiments, the vector comprises the polynucleotide of SEQ ID NO: 40 and/or the polynucleotide of SEQ ID NO: 45.

In some embodiments, the vector comprises a polynucleotide encoding the VH of SEQ ID NO: 87 and/or the VL of SEQ ID NO: 88.

In some embodiments, the vector comprises the polynucleotide of SEQ ID NO: 95 and/or the polynucleotide of SEQ ID NO: 96.

In some embodiments, the vector comprises a polynucleotide encoding the VH of SEQ ID NO: 89 and/or the VL of SEQ ID NO: 90.

In some embodiments, the vector comprises the polynucleotide of SEQ ID NO: 99 and/or the polynucleotide of SEQ ID NO: 100.

In some embodiments, the vector comprises the polynucleotide encoding the VH of SEQ ID NO: 66 and/or the VL of SEQ ID NO: 67.

In some embodiments, the vector comprises the polynucleotide of SEQ ID NO: 105 and/or the polynucleotide of SEQ ID NO: 106.

In some embodiments, the vector comprises the polynucleotide encoding the VH of SEQ ID NO: 74 and/or the VL of SEQ ID NO: 75.

In some embodiments, the vector comprises the polynucleotide of SEQ ID NO: 107 and/or the polynucleotide of SEQ ID NO: 108.

In some embodiments, the vector comprises the polynucleotide encoding the HC of SEQ ID NO: 32 and/or the LC of SEQ ID NO: 35.

In some embodiments, the vector comprises the polynucleotide of SEQ ID NO: 46 and/or the polynucleotide of SEQ ID NO: 49.

In some embodiments, the vector comprises the polynucleotide encoding the HC of SEQ ID NO: 33 and/or the LC of SEQ ID NO: 36.

In some embodiments, the vector comprises the polynucleotide of SEQ ID NO: 47 and/or the polynucleotide of SEQ ID NO: 50.

In some embodiments, the vector comprises the polynucleotide encoding the HC of SEQ ID NO: 34 and/or the LC of SEQ ID NO: 37.

In some embodiments, the vector comprises the polynucleotide of SEQ ID NO: 48 and/or the polynucleotide of SEQ ID NO: 51.

In some embodiments, the vector comprises the polynucleotide encoding the HC of SEQ ID NO: 33 and/or the LC of SEQ ID NO: 38.

In some embodiments, the vector comprises the polynucleotide of SEQ ID NO: 47 and/or the polynucleotide of SEQ ID NO: 52.

In some embodiments, the vector comprises the polynucleotide encoding the VH of SEQ ID NO: 91 and/or the VL of SEQ ID NO: 92.

In some embodiments, the vector comprises the polynucleotide of SEQ ID NO: 97 and/or the polynucleotide of SEQ ID NO: 98.

In some embodiments, the vector comprises the polynucleotide encoding the VH of SEQ ID NO: 93 and/or the VL of SEQ ID NO: 94.

In some embodiments, the vector comprises the polynucleotide of SEQ ID NO: 101 and/or the polynucleotide of SEQ ID NO: 102.

In some embodiments, the vector comprises the polynucleotide encoding the HC of SEQ ID NO: 76 and/or the LC of SEQ ID NO: 77.

In some embodiments, the vector comprises the polynucleotide of SEQ ID NO: 80 and/or the polynucleotide of SEQ ID NO: 81.

In some embodiments, the vector comprises the polynucleotide encoding the HC of SEQ ID NO: 78 and/or the LC of SEQ ID NO: 79.

In some embodiments, the vector comprises the polynucleotide of SEQ ID NO: 82 and/or the polynucleotide of SEQ ID NO: 83.

The vectors described herein may be used to transform various cells with the genes encoding the described antibodies or antigen-binding fragments. For example, the vectors may be used to generate anti-TMEFF2 antibody or antigen-binding fragment-producing cells. Thus, the invention also provides a host cells comprising one or more vectors of the invention.

Techniques for the introduction of foreign genes into cells are known and may be used to construct the recombinant cells of the invention.

"Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell but are still included within the scope of the term "host cell" as used herein.

Such host cells may be eukaryotic cells, prokaryotic cells, plant cells or archeal cells. *Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (for example, *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NSO (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHOK1SV (Lonza Biologics, Walkersville, Md.), Potelligent® CHOK2SV (Lonza), CHO-K1 (ATCC CRL-61) or DG44.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be affected through the use of chemicals, UV-wavelength light, radiation, viruses, insertional mutagens, inhibition of DNA mismatch repair, or a combination of such methods.

The invention also provides a method of producing an antibody of the invention comprising culturing the host cell of the invention in conditions that the antibody is expressed, and recovering the antibody produced by the host cell. Methods of making antibodies and purifying them are well known in the art. Once synthesized (either chemically or recombinantly), the whole antibodies, their dimers, individual light and/or heavy chains, or other antibody fragments such as VH and/or VL, may be purified according to standard procedures, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody may be substantially pure, for example, at least about 80% to 85% pure, at least about 85% to 90% pure, at least about 90% to 95% pure, or at least about 98% to 99%, or more, pure, for example, free from contaminants such as cell debris, macromolecules, etc. other than the subject antibody.

The polynucleotide sequences of the invention may be incorporated into vectors using standard molecular biology methods. Host cell transformation, culture, antibody expression and purification are done using well known methods.

The invention also provides a method of producing the anti-TMEFF2 antibody of the invention, comprising:
  incorporating the first polynucleotide encoding the VH of the antibody and the second polynucleotide encoding the VL of the antibody into an expression vector;
  transforming a host cell with the expression vector;
  culturing the host cell in culture medium under conditions wherein the VL and the VH are expressed and form the antibody; and
  recovering the antibody from the host cell or culture medium.

Pharmaceutical Compositions/Administration

The invention also provides a pharmaceutical composition comprising the antibody of the invention and a pharmaceutically acceptable carrier. For therapeutic use, the antibodies of the invention may be prepared as pharmaceutical compositions containing an effective amount of the antibody as an active ingredient in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies of the invention in such pharmaceutical formulation may vary, from less than about 0.5%, usually to at least about 1% to as much as 15 or 20% by weight and may be selected primarily based on required dose, fluid volumes, viscosities, etc., according to the mode of administration selected. Suitable vehicles and formulations, inclusive of other human proteins, e.g., human serum albumin, are described, for example, in e.g. Remington: The Science and Practice of Pharmacy, 21st Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration of the antibodies of the invention may be any suitable route such as parenteral administration, e.g., intradermal, intramuscular, intraperitoneal, intravenous or subcutaneous, transmucosal (oral, intranasal, intravaginal, rectal) or other means appreciated by the skilled artisan, as well known in the art.

The antibodies of the invention may also be administered prophylactically in order to reduce the risk of developing a disease such as cancer.

Thus, a pharmaceutical composition of the invention for intramuscular injection may be prepared to contain 1 ml sterile buffered water, and between about 1 ng to about 100 mg/kg, e.g. about 50 ng to about 30 mg/kg or more preferably, about 5 mg to about 25 mg/kg, of the antibody of the invention.

Methods of Using Anti-TMEFF2 Antibodies and Bispecific Anti-TMEFF2/Anti-CD3 Antibodies The invention also provides a method of treating a TMEFF2 positive cancer in a subject in need thereof, comprising administering a therapeutically effective amount of the bispecific anti-TMEFF2/anti-CD3 antibody or an antigen binding fragment thereof to the subject to treat the TMEFF2 positive cancer.

The invention also provides a method of treating a TMEFF2 positive cancer in a subject in need thereof, comprising administering a therapeutically effective amount of the anti-TMEFF2 antibody or an antigen binding fragment thereof to the subject to treat the TMEFF2 positive cancer.

Multiple genes have been implicated in the development of prostate cancer. One of the proteins involved in the development and progression of prostate cancer and thus being a promising target for new anti-prostate cancer therapies is Transmembrane protein with EGF-like and two Follistatin-like domains (TMEFF2). TMEFF2 is a type I transmembrane protein composed of two follistatin-like (FS) domains, an EGF-like domain, transmembrane (TM) domain and short cytoplasmic tail. The highest expression of the TMEFF2 protein was detected in two organs: brain and prostate (Liang et al. 2000; Horie et al. 2000). Elevated expression of TMEFF2 was also found in prostate cancer cell lines and clinical samples (Glynne-Jones et al. 2001; Gery et al. 2002; Afar et al. 2004), indicating that TMEFF2 plays a significant role in prostate cancer progression. The expression of the Tmeff2 gene is under the control of the androgen receptor. A large number of androgen-dependent cancer patients exhibited high levels of TMEFF2 mRNA.

Thus, anti-TMEFF2 antibodies may have the potential to become important tools for diagnosis, prognosis or treatment of prostate cancer.

"Cancer" is meant to include all types of cancerous growths or oncogenic processes, metastatic tissues or malignantly transformed cells, tissues, or organs, irrespective of histopathology type or stage of invasiveness. Exemplary TMEFF positive cancers include prostate cancer.

In some embodiments, prostate cancer is adenocarcinoma.

In some embodiments, prostate cancer is a metastatic prostate cancer. In some embodiments, prostate cancer has metastasized to rectum, lymph node or bone, or any combination thereof.

In some embodiments, prostate cancer is relapsed or refractory prostate cancer.

In some embodiments, prostate cancer is castration resistant prostate cancer.

In some embodiments, prostate cancer is sensitive to androgen deprivation therapy.

In some embodiments, prostate cancer is insensitive to androgen deprivation therapy.

The invention also provides an isolated bispecific anti-TMEFF2/anti-CD3 antibody or an antigen binding fragment thereof for use in therapy.

The invention also provides an isolated bispecific anti-TMEFF2/anti-CD3 antibody or an antigen binding fragment thereof for use in treating TMEFF2 positive cancer.

The invention also provides an isolated bispecific anti-TMEFF2/anti-CD3 antibody or an antigen binding fragment thereof for use in treating TMEFF2 prostate cancer.

The invention also provides an isolated bispecific anti-TMEFF2/anti-CD3 antibody or an antigen binding fragment thereof for manufacture of a medicament for treating TMEFF2 positive cancer.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein
  the first domain comprises a HCDR1, a HCDR2, a HCDR3, a LCDR1, a LCDR2 and a LCDR3 of SEQ ID NOs: 10, 12, 15, 18, 20 and 22, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
  the first domain comprises a VH of SEQ ID NO: 25 and a VL of SEQ ID NO: 28, and the second domain comprises the VH of SEQ ID NO: 66 and the VL of SEQ ID NO: 67; and/or
  the bispecific anti-TMEFF2/anti-CD3 antibody or the antigen binding fragment thereof comprises a first heavy chain (HC1) of SEQ ID NO: 32, a first light chain (LC1) of SEQ ID NO: 35, a second heavy chain (HC2) of SEQ ID NO: 76 and a second light chain (LC2) of SEQ ID NO: 77.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein
  the first domain comprises a HCDR1, a HCDR2, a HCDR3, a LCDR1, a LCDR2 and a LCDR3 of SEQ ID NOs: 10, 12, 15, 18, 20 and 22, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
  the first domain comprises a VH of SEQ ID NO: 25 and a VL of SEQ ID NO: 28, and the second domain comprises the VH of SEQ ID NO: 74 and the VL of SEQ ID NO: 75; and/or
  the bispecific anti-TMEFF2/anti-CD3 antibody or the antigen binding fragment thereof comprises a HC1 of SEQ ID NO: 32, a LC1 of SEQ ID NO: 35, a HC2 of SEQ ID NO: 78 and a LC2 of SEQ ID NO: 79.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein
  the first domain comprises a HCDR1, a HCDR2, a HCDR3, a LCDR1, a LCDR2 and a LCDR3 of SEQ ID NOs: 11, 13, 16, 19, 21, and 23, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
  the first domain comprises a VH of SEQ ID NO: 26 and a VL of SEQ ID NO: 29, and the second domain comprises the VH of SEQ ID NO: 66 and the VL of SEQ ID NO: 67; and/or
  the bispecific anti-TMEFF2/anti-CD3 antibody or the antigen binding fragment thereof comprises a HC1 of SEQ ID NO: 33, a LC1 of SEQ ID NO: 36, a HC2 of SEQ ID NO: 76 and a LC2 of SEQ ID NO: 77.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein
  the first domain comprises a HCDR1, a HCDR2, a HCDR3, a LCDR1, a LCDR2 and a LCDR3 of SEQ ID NOs: 11, 13, 16, 19, 21, and 23, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;
  the first domain comprises a VH of SEQ ID NO: 26 and a VL of SEQ ID NO: 29, and the second domain comprises the VH of SEQ ID NO: 74 and the VL of SEQ ID NO:75; and/or
  the bispecific anti-TMEFF2/anti-CD3 antibody or the antigen binding fragment thereof comprises a HC1 of SEQ ID NO: 33, a LC1 of SEQ ID NO: 36, a HC2 of SEQ ID NO: 78 and a LC2 of SEQ ID NO: 79.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein
  the first domain comprises a HCDR1, a HCDR2, a HCDR3, a LCDR1, a LCDR2 and a LCDR3 of SEQ ID NOs: 10, 14, 17, 18, 20 and 24, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;
  the first domain comprises a VH of SEQ ID NO: 27 and a VL of SEQ ID NO: 30, and the second domain comprises the VH of SEQ ID NO: 66 and the VL of SEQ ID NO: 67; and/or
  the bispecific anti-TMEFF2/anti-CD3 antibody or the antigen binding fragment thereof comprises a HC1 of SEQ ID NO: 34, a LC1 of SEQ ID NO: 37, a HC2 of SEQ ID NO: 76 and a LC2 of SEQ ID NO: 77.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 14, 17, 18, 20 and 24, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;

the first domain comprises a VH of SEQ ID NO: 27 and a VL of SEQ ID NO: 30, and the second domain comprises the VH of SEQ ID NO: 74 and the VL of SEQ ID NO: 75; and/or the bispecific anti-TMEFF2/anti-CD3 antibody or the antigen binding fragment thereof comprises a HC1 of SEQ ID NO: 34, a LC1 of SEQ ID NO: 37, a HC2 of SEQ ID NO: 78 and a LC2 of SEQ ID NO: 79.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 11, 13, 16, 18, 20 and 22, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;

the first domain comprises a VH of SEQ ID NO: 26 and a VL of SEQ ID NO: 31, and the second domain comprises the VH of SEQ ID NO: 66 and the VL of SEQ ID NO: 67; and/or the bispecific anti-TMEFF2/anti-CD3 antibody or the antigen binding fragment thereof comprises a HC1 of SEQ ID NO: 33, a LC1 of SEQ ID NO: 38, a HC2 of SEQ ID NO: 76 and a LC2 of SEQ ID NO: 77.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 11, 13, 16, 18, 20 and 22, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;

the first domain comprises a VH of SEQ ID NO: 26 and a VL of SEQ ID NO: 31, and the second domain comprises the VH of SEQ ID NO: 74 and the VL of SEQ ID NO: 75; and/or the bispecific anti-TMEFF2/anti-CD3 antibody or the antigen binding fragment thereof comprises a HC1 of SEQ ID NO: 33, a LC1 of SEQ ID NO: 38, a HC2 of SEQ ID NO: 78 and a LC2 of SEQ ID NO: 79.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;

the first domain comprises a VH of SEQ ID NO: 87 and a VL of SEQ ID NO: 88, and the second domain comprises the VH of SEQ ID NO: 66 and the VL of SEQ ID NO: 67; and/or the bispecific anti-TMEFF2/anti-CD3 antibody or the antigen binding fragment thereof comprises a HC1 of SEQ ID NO: 91, a LC1 of SEQ ID NO: 92, a HC2 of SEQ ID NO: 76 and a LC2 of SEQ ID NO: 77.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;

the first domain comprises a VH of SEQ ID NO: 87 and a VL of SEQ ID NO: 88, and the second domain comprises the VH of SEQ ID NO: 74 and the VL of SEQ ID NO: 75; and/or the bispecific anti-TMEFF2/anti-CD3 antibody or the antigen binding fragment thereof comprises a HC1 of SEQ ID NO: 91, a LC1 of SEQ ID NO: 92, a HC2 of SEQ ID NO: 78 and a LC2 of SEQ ID NO: 79.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 60, 61, 62, 63, 64 and 65, respectively;

the first domain comprises a VH of SEQ ID NO: 89 and a VL of SEQ ID NO: 90, and the second domain comprises the VH of SEQ ID NO: 66 and the VL of SEQ ID NO: 67; and/or the bispecific anti-TMEFF2/anti-CD3 antibody or the antigen binding fragment thereof comprises a HC1 of SEQ ID NO: 93, a LC1 of SEQ ID NO: 94, a HC2 of SEQ ID NO: 76 and a LC2 of SEQ ID NO: 77.

The invention also provides an isolated bispecific anti-TMEFF2/anti-CD3 antibody or an antigen binding fragment thereof for use in the treatment of TMEFF2 positive cancer, such as prostate cancer, wherein the bispecific anti-TMEFF2/anti-CD3 antibody comprises a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises the HCDR1, the HCDR2, the HCDR3, the LCDR1, the LCDR2 and the LCDR3 of SEQ ID NOs: 68, 69, 70, 71, 72 and 73, respectively;

the first domain comprises a VH of SEQ ID NO: 89 and a VL of SEQ ID NO: 90, and the second domain comprises the VH of SEQ ID NO: 74 and the VL of SEQ ID NO: 75; and/or the bispecific anti-TMEFF2/anti-CD3 antibody or the antigen binding fragment thereof comprises a HC1 of SEQ ID NO: 93, a LC1 of SEQ ID NO: 94, a HC2 of SEQ ID NO: 78 and a LC2 of SEQ ID NO: 79.

The antibodies of the invention may be administered in combination with a second therapeutic agent.

In some embodiments, the second therapeutic agent is surgery, chemotherapy, androgen deprivation therapy or radiation, or any combination thereof.

Kits

The invention also provides a kit comprising the anti-TMEFF2 antibody or the bispecific anti-TMEFF2/anti-CD3 antibody of the invention. The kit may be used for therapeutic uses or as diagnostic kits. The kit may be used to detect the presence of TMEFF2, CD3 or TMEFF2 and CD3 in a sample.

In some embodiments, the kit comprises the antibody of the invention and reagents for detecting the antibody. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

In some embodiments, the kit comprises the antibody of the invention in a container and instructions for use of the kit.

In some embodiments, the antibody in the kit is labeled.

The invention also provides a kit comprising the anti-TMEFF2 antibody comprising the VH of SEQ ID NO: 25 and the VL of SEQ ID NO: 28.

The invention also provides a kit comprising the anti-TMEFF2 antibody comprising the VH of SEQ ID NO: 26 and the VL of SEQ ID NO: 29.

The invention also provides a kit comprising the anti-TMEFF2 antibody comprising the VH of SEQ ID NO: 27 and the VL of SEQ ID NO: 30.

The invention also provides a kit comprising the anti-TMEFF2 antibody comprising the VH of SEQ ID NO: 26 and the VL of SEQ ID NO: 31.

The invention also provides a kit comprising the anti-TMEFF2 antibody comprising the VH of SEQ ID NO: 87 and the VL of SEQ ID NO: 88.

The invention also provides a kit comprising the anti-TMEFF2 antibody comprising the VH of SEQ ID NO: 89 and the VL of SEQ ID NO: 90.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 25 and a VL of SEQ ID NO: 28, and the second domain comprises the VH of SEQ ID NO: 66 and the VL of SEQ ID NO: 67.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 25 and a VL of SEQ ID NO: 28, and the second domain comprises the VH of SEQ ID NO: 74 and the VL of SEQ ID NO: 75.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 26 and a VL of SEQ ID NO: 29, and the second domain comprises the VH of SEQ ID NO: 66 and the VL of SEQ ID NO: 67.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 26 and a VL of SEQ ID NO: 29, and the second domain comprises the VH of SEQ ID NO: 74 and the VL of SEQ ID NO: 75.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 27 and a VL of SEQ ID NO: 30, and the second domain comprises the VH of SEQ ID NO: 66 and the VL of SEQ ID NO: 67.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 27 and a VL of SEQ ID NO: 30, and the second domain comprises the VH of SEQ ID NO: 74 and the VL of SEQ ID NO:75.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 26 and a VL of SEQ ID NO: 31, and the second domain comprises the VH of SEQ ID NO: 66 and the VL of SEQ ID NO:67.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 26 and a VL of SEQ ID NO: 31, and the second domain comprises the VH of SEQ ID NO: 74 and the VL of SEQ ID NO: 75.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 87 and a VL of SEQ ID NO: 88, and the second domain comprises the VH of SEQ ID NO: 66 and the VL of SEQ ID NO: 67.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 87 and a VL of SEQ ID NO: 88, and the second domain comprises the VH of SEQ ID NO: 74 and the VL of SEQ ID NO: 75.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 89 and a VL of SEQ ID NO: 90, and the second domain comprises the VH of SEQ ID NO: 66 and the VL of SEQ ID NO: 67.

The invention also provides a kit comprising the bispecific anti-TMEFF2/anti-CD3 antibody comprising a first domain that binds TMEFF2 and a second domain that binds CD3, wherein the first domain comprises a VH of SEQ ID NO: 89 and a VL of SEQ ID NO: 90, and the second domain comprises the VH of SEQ ID NO: 74 and the VL of SEQ ID NO: 75.

Methods of Detecting TMEFF2 or CD3

The invention also provides a method of detecting TMEFF2 in a sample, comprising obtaining the sample, contacting the sample with the anti-TMEFF2 antibody of the invention, and detecting the antibody bound to TMEFF2 in the sample.

The invention also provides a method of detecting TMEFF2 and CD3 in a sample, comprising obtaining the sample, contacting the sample with the bispecific anti-TMEFF2/anti-CD3 antibody comprising a first domain that binds TMEFF2 and a second domain that binds CD3 of the invention, and detecting the antibody bound to TMEFF2 and CD3 in the sample.

In some embodiments, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like.

The antibodies of the invention described herein bound to TMEFF2 or TMEFF2 and CD3 may be detected using known methods. Exemplary methods include direct labeling of the antibodies using fluorescent or chemiluminescent labels, or radiolabels, or attaching to the antibodies of the invention a moiety which is readily detectable, such as biotin, enzymes or epitope tags. Exemplary labels and moieties are ruthenium, 111In-DOTA, 111In-diethylenetri-aminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes and Alexafluor® dyes.

The antibodies of the invention may be used in a variety of assays to detect TMEFF2 or TMEFF2 and CD3 in the sample. Exemplary assays are western blot analysis, radioimmunoassay, surface plasmon resonance, immunoprecipitation, equilibrium dialysis, immunodiffusion, electrochemiluminescence (ECL) immunoassay, immunohistochemistry, fluorescence-activated cell sorting (FACS) or ELISA assay.

The present invention will now be described with reference to the following specific, non-limiting examples.

Example 1: Antigen Generation

Human extracellular domain (ECD) TMEFF2 was produced based on UniProt Accession #Q9UIK5 sequence. The ECD construct was designed with a 6×His-tag and Avi-tag sequences at the C-terminus (construct TMEW1; SEQ ID NO: 6). A construct containing the FS2 and EGF domains (amino acids 151-320 was designed as a human serum albumin (HSA) fusion with a 6×His-tag and avitag sequences (construct TMEW7; SEQ ID NO: 7). A construct containing the TMEFF2 membrane proximal domain (residues 230-320) was designed with a 6×His tag (construct TMEW19; SEQ ID NO: 8) or fused to a rat IgG1 Fc with a His-tag (construct TMEW20; SEQ ID NO: 9). Residues 230-320 of TMEFF2 contain the EGF domain which spans the residues 261-301 of TMEFF2. The human TMEFF2 ECD expression constructs were transiently transfected into HEK293 derived cells, Expi293 (Gibco/Thermo Fisher Scientific) using Expifectamine according to manufacturer protocol. Cells were incubated 5 days at 37° C. with 8% $CO_2$ on an orbital shaker before harvesting. The expressed cells were removed by centrifugation and the soluble TMEFF2 proteins with his-tags were purified from the media using immobilized metal affinity chromatography using Ni Sepharose 6 Fast Flow resin (GE Healthcare) followed by Superdex 200 preparative size exclusion chromatography (SEC) (GE Healthcare) in Dubelcco's Phosphate Saline buffer pH 7.2 (1×DPBS). The amino acid sequences of the generated antigens are shown in Table 3.

TABLE 3

| Protein AA ID | Description | Amino Acid Sequence |
|---|---|---|
| TMEW1 (SEQ ID NO: 6) | TMEFF2-FL-ECD-His-Avitag | FPTSLSDCQTPTGWNCSGYDDRENDLFLCDTNTCK FDGECLRIGDTVTCVCQFKCNNDYVPVCGSNGESY QNECYLRQAACKQQSEILVVSEGSCATDAGSGSGD GVHEGSGETSQKETSTCDICQFGAECDEDAEDVWC VCNIDCSQTNFNPLCASDGKSYDNACQIKEASCQK QEKIEVMSLGRCQDNTTTTTKSEDGHYARTDYAEN ANKLEESAREHHIPCPEHYNGFCMHGKCEHSINMQ EPSCRCDAGYTGQHCEKKDYSVLYVVPGPVRFQY VGGGSHHHHHHLNDIFEAQKIEWHE |
| TMEW7 (SEQ ID NO: 7) | FS2-EGF-Tev-HSA(C34S)-His-Avitag | SGETSQKETSTCDICQFGAECDEDAEDVWCVCNID CSQTNFNPLCASDGKSYDNACQIKEASCQKQEKIEV MSLGRCQDNTTTTTKSEDGHYARTDYAENANKLE ESAREHHIPCPEHYNGFCMHGKCEHSINMQEPSCRC DAGYTGQHCEKKDYSVLYVVPGPVRFQYVGSGSG SENLYFQGVRSSSDAHKSEVAHRFKDLGEENFKAL VLIAFAQYLQQSPFEDHVKLVNEVTEFAKTCVADE SAENCDKSLHTLFGDKLCTVATLRETYGEMADCCA KQEPERNECFLQHKDDNPNLPRLVRPEVDVMCTAF HDNEETFLKKYLYEIARRHPYFYAPELLFFAKRYKA AFTECCQAADKAACLLPKLDELRDEGKASSAKQRL KCASLQKFGERAFKAWAVARLSQRFPKAEFAEVSK LVTDLTKVHTECCHGDLLECADDRADLAKYICENQ DSISSKLKECCEKPLLEKSHCIAEVENDEMPADLPSL AADFVESKDVCKNYAEAKDVFLGMFLYEYARRHP DYSVVLLLRLAKTYETTLEKCCAAADPHECYAKVF DEFKPLVEEPQNLIKQNCELFEQLGEYKFQNALLVR YTKKVPQVSTPTLVEVSRNLGKVGSKCCKHPEAKR MPCAEDYLSVVLNQLCVLHEKTPVSDRVTKCCTES LVNRRPCFSALEVDETYVPKEFNAETFTFHADICTL SEKERQIKKQTALVELVKHKPKATKEQLKAVMDDF AAFVEKCCKADDKETCFAEEGKKLVAASQAALGL GGGSHHHHHHLNDIFEAQKIEWHE |

TABLE 3-continued

| Protein AA ID Description | | Amino Acid Sequence |
|---|---|---|
| TMEW19 (SEQ ID NO: 8) | spTMEFF2(230-320)G3S-H6 | NTTTTTKSEDGHYARTDYAENANKLEESAREHHIP CPEHYNGFCMHGKCEHSINMQEPSCRCDAGYTGQ HCEKKDYSVLYVVPGPVRFQYVGGGSHHHHHH |
| TMEW20 (SEQ ID NO: 9) | spTMEFF2(230-320)- G3S-ratIgG1Fc | NTTTTTKSEDGHYARTDYAENANKLEESAREHHIP CPEHYNGFCMHGKCEHSINMQEPSCRCDAGYTGQ HCEKKDYSVLYVVPGPVRFQYVGGGSPRNCGGDC KPCICTGSEVSSVFIFPPKPKDVLTITLTPKVTCVVV DISQDDPEVHFSWFVDDVEVHTAQTRPPEEQFNSTF RSVSELPILHQDWLNGRTFRCKVTSAAFPSPIEKTIS KPEGRTQVPHVYTMSPTKEEMTQNEVSITCMVKGF YPPDIYVEWQMNGQPQENYKNTPPTMDTDGSYFL YSKLNVKKEKWQQGNTFTCSVLHEGLHNHHTEKS LSHSPGKGGGSHHHHHH |

Example 2. Generation of Anti-TMEFF2 Antibodies

Antibody Generation Using Transgenic Rats Expressing Human Immunoglobulin Loci (OmniRat R)

The OmniRat contains a chimeric human/rat IgH locus (comprising 22 human $V_H$S, all human D and $J_H$ segments in natural configuration linked to the rat $C_H$ locus) together with fully human IgL loci (12 $V_{\kappa S}$ linked to $J_\kappa$-$C_\kappa$ and 16 Vλs linked to Jλ-Cλ). (see e.g., Osborn, et al. (2013) *J Immunol* 190(4): 1481-1490). Accordingly, the rats exhibit reduced expression of rat immunoglobulin, and in response to immunization, the introduced human heavy and light chain transgenes undergo class switching and somatic mutation to generate high affinity chimeric human/rat IgG monoclonal antibodies with fully human variable regions. The preparation and use of OmniRat®, and the genomic modifications carried by such rats, is described in WO14/093908.

OmniRats were immunized with the human TMEFF2 construct FS2-EGF-Tev-HSA(C34S)-His-Avitag (TMEW7, SEQ ID NO: 7) and boosted with the construct spTMEFF2 (230-320)G3S-ratIgG1Fc (TMEW20, SEQ ID NO: 9). Following a 89 day immunization regimen, lymph nodes from the rats were harvested and used to generate hybridomas and the hybridoma supernatants were screened for binding to human TMEFF2-FL-ECD-His-Avitag (TMEW1) protein by ELISA and/or SPARCL (Spatial Proximity Analyte Reagent Capture Luminescence). Several supernatants were selected for secondary ELISA and SPARCL screening of binding to TMEFF ECD, FS2-EGF, or EGF domain only TMEFF2. Based on the screening results, several hybridoma clones were sequenced, expressed and characterized for functionality.

Antibody Generation from Phage Display Libraries

TMEFF2 binding Fabs were selected using standard methods from two sets of de novo pIX phage display libraries as described in Shi et al., J Mol Biol 397:385-96, 2010 and WO2009/085462). Briefly, two sets of libraries, referred to as V3.0 and V5.0, were generated by diversifying human scaffolds where germline VH genes IGHV1-69*01, IGHV3-23*01 and IGHV5-51*01 were recombined with the human IGHJ-4 minigene via the H3 loop (IGHJ-6 minigene was also used in V5.0), and human germline VLkappa genes O12 (IGKV1-39*01), L6 (IGKV3-11*01), A27 (IGKV3-20*01), and B3 (IGKV4-1*01) were recombined with the IGKJ-1 minigene to assemble complete VH and VL domains. Positions in the heavy and light chain variable regions around the H1, H2, L1, L2 and L3 loops in frequent contact with protein and peptide antigens were chosen for diversification. Sequence diversity at selected positions was limited to residues occurring at each position in the IGHV or IGLV germline gene families of the respective IGHV or IGLV genes. Diversity at the H3 loop was generated by utilizing short to mid-sized synthetic loops of lengths 7-14 amino acids for V3.0 libraries, and lengths 6-19 amino acids for V5.0 libraries. The amino acid distribution at H3 was designed to mimic the observed variation of amino acids in human antibodies. The scaffolds utilized to generate libraries were named according to their human VH and VL germline gene origin. For both V3.0 and V5.0 sets, each of the three heavy chain libraries were combined with the four germline light chains or germline light chain libraries to generate 12 unique VH:VL combinations for each set of libraries which are used for selection experiments.

V Region Cloning

Total RNA from hybridoma cell lysates of phage were purified using RNeasy 96 kit (Qiagen) following the manufacturer's protocol. The resulting RNA was quantitated using Drop Sense and either stored at −80° C. or used for cDNA synthesis using Invitrogen SuperScript III First-Strand Synthesis System by RT-PCR (Invitrogen). The first strand cDNA synthesis was carried out using gene specific primers annealed to the constant regions of heavy, kappa, and lambda chains, respectively. The RT-PCR reaction mixture comprised of up to 3 μg of purified RNA, gene specific primer, dNTP mix, reaction buffer, 25 mM $MgCl_2$, DTT, RNaseOUT™ (40 U/μl, Invitrogen), and SuperScript™ III RT (200 U/μl, Invitrogen Cat #18080-051) was incubated at 50° C. for 50 minutes and 85° C. for 5 minutes. The resulting single-stranded cDNA was stored at −20° C., or used directly for PCR amplification. The PCR reaction was carried out using Platinum Pfx polymerase (Invitrogen). The v-region fragments were amplified by forward and reverse primers annealing to the leader sequences and constant regions of heavy, kappa and lambda chains, respectively, using optimized PCR conditions. The resulting PCR fragments were sequenced, the amino acid sequences of the recovered v-regions were codon optimized and cloned into the pUnder-based expression vector carrying the IgG4 constant region with S228P, F234A and L235A mutations (IgG4PAA isotype).

Expi293 Small Scale Transfection and Purification

Select antibodies identified from the immunization campaigns or phage display were cloned and expressed as IgG1PAA and purified via small 2 ml scale. Expi293™ cells (ThermoFisher Scientific) were seeded at $1.25 \times 10^5$-$2.25 \times 10^5$ viable cells/mL density in Expi293™ Expression Medium and cultured in 125 mL-2 L shake flasks at 37° C., 7% $CO_2$. Cells were sub-cultured when density reached the log phase growth at $3\times10^6$-$5\times10^6$ viable cells/mL with a 98-99% viability.

On day of transfection, the viable cell density and percent viability was determined. Cells were transfected at a density of $3\times10^6$ viable cells/mL following manufacturer's Transfection protocol (ThermoFisher Publication Number MAN0007814). Culture were harvested on Day 6 post-transfection by centrifugation at 850×G for 15 minutes before purification. Antibodies were purified from the clarified supernatants using mAb Select Sure resin (GE Healthcare) and dialyzed into PBS. Protein concentrations were determined by A280 measurement on the filtrate using a DropSense Instrument (Trinean).

Example 3. Characterization of Anti-TMEFF2 Antibodies

Anti-TMEFF2 Antibodies Bind TMEFF2 with High Affinity

Binding of select IgG4PAA anti-TMEFF2 antibodies to TMEFF2 ECD (TMEW1: TMEFF2-FL ECD-His-Avitag) and/or the membrane proximal region (TMEW19: spTM-EFF2(230-320)G3S-H6) was assessed using Proteon (TMEB674, TMEB675, TMEB 565 and TMEB570) or Biacore SPR (TMEB762 and TMEB757). The kinetic parameters of binding selected antibodies are show in Table 4. The anti-TMEFF2 antibodies were found to bind both the TMEFF2 ECD and TMEFF2 membrane proximal region with picomolar affinities.

TABLE 4

| Antibody | Antigen | TMEFF2 domain | ka (1/Ms) | kd (1/s) | KD (nM) |
| --- | --- | --- | --- | --- | --- |
| TMEB674 | TMEW1 | ECD | 2.01E+06 | 1.62E−04 | 0.10 |
| TMEB674 | TMEW19 | MP* | 8.37E+05 | 1.75E−04 | 0.20 |
| TMEB675 | TMEW1 | ECD | 2.65E+06 | 1.53E−04 | 0.10 |
| TMEB675 | TMEW19 | MP | 9.72E+05 | 1.58E−04 | 0.20 |
| TMEB565 | TMEW1 | ECD | 3.84E+05 | 9.13E−06 | 0.02 |
| TMEB565 | TMEW19 | MP | 7.77E+05 | 6.39E−06 | 0.01 |
| TMEB570 | TMEW1 | ECD | 4.64E+05 | 5.13E−05 | 0.11 |
| TMEB570 | TMEW19 | MP | 7.62E+05 | 4.67E−05 | 0.06 |
| TMEB762 | TMEW1 | ECD | 5.41E+05 | 1.74E−04 | 0.32 |
| TMEB757 | TMEW1 | ECD | 5.42E+05 | 1.67E−04 | 0.31 |

*MP: membrane proximal region

ProteOn SPR

The binding of anti-TMEFF2 mAbs to the ECD and the membrane proximal region of human TMEFF2 was measured by ProteOn SPR (Bio-Rad). The purified mAbs (diluted to a final concentration of 1 µg/ml in PBST) were used as ligands in the assay and were immobilized through Fc capture to Goat Anti-Human (GAH) IgG Fc. For amine coupling of the GAH IgG Fc, a 1:1 mixture of EDC (40 mM) and NHS (10 mM) were mixed immediately prior to injection to activate the chip surface and injected in the vertical orientation. GAH-Fc (at 30 µg/ml) antibody in acetate buffer (pH 5.0) was then flowed over the surface for 300 seconds at 30 µl/min in the vertical orientation. Any remaining reactive carboxyl groups in the surface were subsequently deactivated by injecting 1M Ethanolamine (pH 8.5) in the same orientation. The antibodies were used at a concentration of 1 µg/ml for immobilization. The antibodies were flowed over the surface in the horizontal direction. Human TMEFF2 ECD or the membrane proximal region in 3-fold dilution series of 5 concentrations (highest concentration ranging from 100-600 nM) was flowed in as analyte in the vertical orientation to bind to the captured molecules. A buffer sample was also injected in the $6^{th}$ channel in the vertical direction to monitor any drift in the baseline signal. The association and dissociation phases for all concentrations were monitored over 3 minutes and 30 (or 15) minutes respectively, at a flow rate of 100 µL/min. The binding surface was regenerated for the next interaction cycle using an 18 second pulse of 0.8% phosphoric acid to remove the bound antigen. The raw data were processed by subtracting two sets of reference data from the response data: 1) the inter-spot signals to correct for the non-specific interactions between the antigen and the empty chip surface; 2) the empty channel signals (where only PBST was flowed over the chip) to correct for non-specific baseline drift.

Biacore 8K SPR

The binding of anti-TMEFF2 mAbs to human TMEFF2 ECD was measured by Biacore 8K SPR. The format of the assay was to capture the mAbs using a high density anti-human Fc surface, then inject human TMEFF2 concentration titration using a single cycle kinetics method. Goat anti-human Fc IgG (Jackson Immunoresearch, Cat #109-005-098) was directly immobilized via amine coupling at 30 µg/mL in 10 mM acetate buffer, pH 4.5 on flow cells 1 and 2, on CM5 Sensor Chip (GE) with a flow rate of 30 µL/min in HBSP (GE) buffer. The mAbs were captured on the anti-human Fc IgG surface at 0.5 µg/ml (~200-300 RU) on flow cell 2. The running buffer was then changed to HBSP+ 100 ug/ml BSA. TMEFF2 ECD at 30 nM concentration in 3-fold dilution series was injected from low to high concentration using single cycle kinetics method. The off-rate was monitored 30 minutes after the last or highest concentration injection and then the surface was regenerated using 0.8% phosphoric acid (Bio-Rad). A buffer blank run, capturing the same mAbs and using the same conditions of sample run was also completed. The raw data were processed by subtracting two sets of reference data from the response data: 1) reference flow cell 1 subtracted from sample flow cell 2 and 2) buffer blank run from experimental run. The processed data at all concentrations for each mAb were globally fit to a 1:1 simple Langmuir binding model to extract estimates of the kinetic (kon, koff) and affinity (KD) constants.

Thermal Stability of Anti-TMEFF2 Antibodies

TMEB675 showed lower than usual thermal stability profile by DSC (Differential Scanning Calorimetry) with onset of unfolding Tm=52° C. and the first thermal transition (Tm1) at =60.4° C. A closer examination of the sequence of TMEB675 (see Example 4) showed the presence of Somatic HyperMutations (SHM) within the framework region of heavy and light chain. Several re-engineered variants were sub-cloned, expressed, purified and profiled by DSC. The resulting mAbs TMEB762 and TMEFB757 showed desirable thermal stability profile (Tm1=69.4° C. and Tm1=69.7° C. respectively). In comparison to TMEB675, TMEB762 had the following amino acid modifications in the heavy chain: R14P, P20L and H81Q, while TMEFB757 had the following amino acid modifications in the heavy chain: R14P and P20L. In comparison to TMEB675, TMEB762 had the following amino acid modifications in the light chain: A1D and A91P, while TMEFB757 had A91P modification in the light chain. Residue numbering is according to Kabat. The kinetic parameters of binding of TMEB675, TMEB762 to TMEFF2 ECD is shown in Table 4.

Example 4. Structural Characterization of Anti-TMEFF2 Antibodies

The cDNA sequences and amino acid translations of the antibodies were obtained using standard techniques. After polypeptide sequence determination, some antibody cDNAs encoding the variable regions or full-length antibodies were codon optimized using standard methods for scale-up expression.

Table 5 shows the HCDR1 and the HCDR2 amino acid sequences of select anti-TMEFF2 antibodies.
Table 6 shows the HCDR3 amino acid sequences of select anti-TMEFF2 antibodies.
Table 7 shows the LCDR1 and the LCDR2 amino acid sequences of select anti-TMEFF2 antibodies.
Table 8 shows the LCDR3 amino acid sequences of select anti-TMEFF2 antibodies.
Table 9 shows the VH and the VL amino acid sequence of select anti-TMEFF2 antibodies.
Table 10 shows the SEQ ID NOs: of heavy and light chains of select anti-TMEFF2 antibodies.
Table 11 shows the heavy chain amino acid sequences of select anti-TMEFF2 antibodies.
Table 12 shows the light chain amino acid sequences of select anti-TMEFF2 antibodies.
Table 13 shows the SEQ ID NOs: of polynucleotides encoding various anti-TMEFF2 antibody chains.

TABLE 5

| mAb | HCDR1 sequence | HCDR1 SEQ ID NO: | HCDR2 sequence | HCDR2 SEQ ID NO: |
|---|---|---|---|---|
| TMEB675 | SYSMS | 10 | VISGSGGFTDYADSVKG | 12 |
| TMEB570 | SYYIS | 11 | GIIPISGRANYAQKFQG | 13 |
| TMEB674 | SYSMS | 10 | VISGGGSFTSYADSVKG | 14 |
| TMEB565 | SYYIS | 11 | GIIPISGRANYAQKFQG | 13 |
| TMEB762 | SYSMS | 10 | VISGSGGFTDYADSVKG | 12 |
| TMEB757 | SYSMS | 10 | VISGSGGFTDYADSVKG | 12 |

TABLE 6

| mAb | HCDR3 sequence | HCDR3 SEQ ID NO: |
|---|---|---|
| TMEB675 | MPLNSPHDY | 15 |
| TMEB570 | DGYSSGRSTTYAFDY | 16 |

TABLE 6-continued

| mAb | HCDR3 sequence | HCDR3 SEQ ID NO: |
|---|---|---|
| TMEB674 | MPLNSPHDC | 17 |
| TMEB565 | DGYSSGRSTTYAFDY | 16 |
| TMEB762 | MPLNSPHDY | 15 |
| TMEB757 | MPLNSPHDY | 15 |

TABLE 7

| mAb | LCDR1 amino acid | LCDR1 SEQ ID NO: | LCDR2 amino acid | LCDR2 SEQ ID NO: |
|---|---|---|---|---|
| TMEB675 | RASQGIRNDLG | 18 | AASSLQS | 20 |
| TMEB570 | RASQSVSTYYLA | 19 | GASYRAT | 21 |
| TMEB674 | RASQGIRNDLG | 18 | AASSLQS | 20 |
| TMEB565 | RASQGIRNDLG | 18 | AASSLQS | 20 |
| TMEB762 | RASQGIRNDLG | 18 | AASSLQS | 20 |
| TMEB757 | RASQGIRNDLG | 18 | AASSLQS | 20 |

TABLE 8

| mAb | LCDR3 amino acid | LCDR3 SEQ ID NO: |
|---|---|---|
| TMEB675 | LQDYNYALT | 22 |
| TMEB570 | QQYGHSPIT | 23 |
| TMEB674 | LQDYNYSLT | 24 |
| TMEB565 | LQDYNYALT | 22 |
| TMEB762 | LQDYNYPLT | 86 |
| TMEB757 | LQDYNYPLT | 86 |

TABLE 9

| Antibody | VH name | VH amino acid sequence | VH SEQ ID NO: | VL name | VL amino acid sequence | VL SEQ ID NO: |
|---|---|---|---|---|---|---|
| TMEB675 | TMEH411 | EVQLLESGGGLVQRGGSLRPSCAASGFTFSSYSMSWVRQAPGKGLEWVSVISGSGGFTDYADSVKGRFTISRDNSKNTLYLHMNSLRAEDTAVYYCARMPLNSPHDYWGQGTLVTVSS | 25 | TMEL127 | AIQMTQSPSSLSASVGDRVTITCRASQGIRNDLGWYQQKPGKAPKLLIYAASSLQSGVPSRFSGSGSGTDFTLTISSLQPEDFATYYCLQDYNYALTFGGGTKVEIK | 28 |
| TMEB570 | TMEH396 | QVQLVQSGAEVKKPGSSVKVSCKASGGTFSSYYISWVRQAPG | 26 | TMEL112 | EIVLTQSPGTLSLSPGERATLSCRASQSVSTYYLAWYQQKPGQAPRLLIYG | 29 |

TABLE 9-continued

| Antibody | VH name | VH amino acid sequence | VH SEQ ID NO: | VL name | VL amino acid sequence | VL SEQ ID NO: |
|---|---|---|---|---|---|---|
| | | QGLEWMGG IIPISGRANY AQKFQGRV TITADESTST AYMELSSLR SEDTAVYY CARDGYSS GRSTTYAFD YWGQGTLV TVSS | | | ASYRATGIPD RFSGSGSGTD FTLTISRLEPE DFAVYYCQQ YGHSPITFGQ GTKVEIK | |
| TMEB674 | TMEH410 | EVQLLESGG GLVQPPGGS LRLSCAASG FTFSSYSMS WVRQAPGK GLEWVSVIS GGGSFTSYA DSVKGRFTI SRDNSNNTL YLQMSSLR AEDTAFYY CARMPLNSP HDCWGQGT LVTVSS | 27 | TMEL126 | AIQMTQSPSS LSASVGDRVT ITCRASQGIRN DLGWYQQKP GKAPKLLIYA ASSLQSGVPS RFSGSGSGTD FTLTISSLQPE DFATYYCLQD YNYSLTFGGG TKVEIR | 30 |
| TMEB565 | TMEH396 | QVQLVQSG AEVKKPGSS VKVSCKAS GGTFSSYYI SWVRQAPG QGLEWMGG IIPISGRANY AQKFQGRV TITADESTST AYMELSSLR SEDTAVYY CARDGYSS GRSTTYAFD YWGQGTLV TVSS | 26 | TMEL111 | EIVLTQSPGTL SLSPGERATLS CRASQSVATY YLAWYQQKP GQAPRLLIYG ASSRATGIPD RFSGSGSGTD FTLTISRLEPE DFAVYYCQQ YGYNPITFGQ GTKVEIK | 31 |
| TMEB762 | TMEH459 | EVQLLESGG GLVQPGGSL RLSCAASGF TFSSYSMSW VRQAPGKG LEWVSVISG SGGFTDYA DSVKGRFTI SRDNSKNTL YLQMNSLR AEDTAVYY CARMPLNSP HDYWGQGT LVTVSS | 87 | DL3L129 | DIQMTQSPSS LSASVGDRVT ITCRASQGIRN DLGWYQQKP GKAPKLLIYA ASSLQSGVPS RFSGSGSGTD FTLTISSLQPE DFATYYCLQD YNYPLTFGGG TKVEIK | 88 |
| TMEB757 | TMEH460 | EVQLLESGG GLVQPGGSL RLSCAASGF TFSSYSMSW VRQAPGKG LEWVSVISG SGGFTDYA DSVKGRFTI SRDNSKNTL YLHMNSLR AEDTAVYY CARMPLNSP HDYWGQGT LVTVSS | 89 | B76L85 | AIQMTQSPSS LSASVGDRVT ITCRASQGIRN DLGWYQQKP GKAPKLLIYA ASSLQSGVPS RFSGSGSGTD FTLTISSLQPE DFATYYCLQD YNYPLTFGGG TKVEIK | 90 |

TABLE 10

| Antibody | VH name | VL name | HC protein SEQ ID NO: | LC protein SEQ ID NO: |
|---|---|---|---|---|
| TMEB675 | TMEH411 | TMEL127 | 32 | 35 |
| TMEB570 | TMEH396 | TMEL112 | 33 | 36 |
| TMEB674 | TMEH410 | TMEL126 | 34 | 37 |
| TMEB565 | TMEH396 | TMEL111 | 33 | 38 |

TABLE 10-continued

| Antibody | VH name | VL name | HC protein SEQ ID NO: | LC protein SEQ ID NO: |
|---|---|---|---|---|
| TMEB762 | TMEH459 | DL3L129 | 91 | 92 |
| TMEB757 | TMEH460 | B76L85 | 93 | 94 |

TABLE 11

| HC PROTEIN SEQ ID NO: | HC AMINO ACID SEQUENCE |
|---|---|
| 32 (TMEB675 HC) | EVQLLESGGGLVQRGGSLRPSCAASGFTFSSYSMSWVRQAPGKGLE WVSVISGSGGFTDYADSVKGRFTISRDNSKNTLYLHMNSLRAEDTA VYYCARMPLNSPHDYWGQGTLVTVSSASTKGPSVFPLAPCSRSTSE STAALGCLVKDYFPEPVTVSWNSGALTSGVHTFPAVLQSSGLYSLS SVVTVPSSSLGTKTYTCNVDHKPSNTKVDKRVESKYGPPCPPCPAPE AAGGPSVFLFPPKPKDTLMISRTPEVTCVVVDVSQEDPEVQFNWYV DGVEVHNAKTKPREEQFNSTYRVVSVLTVLHQDWLNGKEYKCKV SNKGLPSSIEKTISKAKGQPREPQVYTLPPSQEEMTKNQVSLTCLVK GFYPSDIAVEWESNGQPENNYKTTPPVLDSDGSFFLYSRLTVDKSR WQEGNVFSCSVMHEALHNHYTQKSLSLSLGK |
| 33 (TMEB570, TMEB565 HC) | QVQLVQSGAEVKKPGSSVKVSCKASGGTFSSYYISWVRQAPGQGL EWMGGIIPISGRANYAQKFQGRVTITADESTSTAYMELSSLRSEDTA VYYCARDGYSSGRSTTYAFDYWGQGTLVTVSSASTKGPSVFPLAPC SRSTSESTAALGCLVKDYFPEPVTVSWNSGALTSGVHTFPAVLQSSG LYSLSSVVTVPSSSLGTKTYTCNVDHKPSNTKVDKRVESKYGPPCPP CPAPEAAGGPSVFLFPPKPKDTLMISRTPEVTCVVVDVSQEDPEVQF NWYVDGVEVHNAKTKPREEQFNSTYRVVSVLTVLHQDWLNGKEY KCKVSNKGLPSSIEKTISKAKGQPREPQVYTLPPSQEEMTKNQVSLT CLVKGFYPSDIAVEWESNGQPENNYKTTPPVLDSDGSFFLYSRLTV DKSRWQEGNVFSCSVMHEALHNHYTQKSLSLSLGK |
| 34 (TMEB674 HC) | EVQLLESGGGLVQPPGGSLRLSCAASGFTFSSYSMSWVRQAPGKGL EWVSVISGGGSFTSYADSVKGRFTISRDNSNNTLYLQMSSLRAEDT AFYYCARMPLNSPHDCWGQGTLVTVSSASTKGPSVFPLAPCSRSTS ESTAALGCLVKDYFPEPVTVSWNSGALTSGVHTFPAVLQSSGLYSL SSVVTVPSSSLGTKTYTCNVDHKPSNTKVDKRVESKYGPPCPPCPAP EAAGGPSVFLFPPKPKDTLMISRTPEVTCVVVDVSQEDPEVQFNWY VDGVEVHNAKTKPREEQFNSTYRVVSVLTVLHQDWLNGKEYKCK VSNKGLPSSIEKTISKAKGQPREPQVYTLPPSQEEMTKNQVSLTCLV KGFYPSDIAVEWESNGQPENNYKTTPPVLDSDGSFFLYSRLTVDKSR WQEGNVFSCSVMHEALHNHYTQKSLSLSLGK |
| 91 (TMEB762 HC) | EVQLLESGGGLVQPGGSLRLSCAASGFTFSSYSMSWVRQAPGKGLE WVSVISGSGGFTDYADSVKGRFTISRDNSKNTLYLQMNSLRAEDTA VYYCARMPLNSPHDYWGQGTLVTVSSASTKGPSVFPLAPCSRSTSE STAALGCLVKDYFPEPVTVSWNSGALTSGVHTFPAVLQSSGLYSLS SVVTVPSSSLGTKTYTCNVDHKPSNTKVDKRVESKYGPPCPPCPAPE AAGGPSVFLFPPKPKDTLMISRTPEVTCVVVDVSQEDPEVQFNWYV DGVEVHNAKTKPREEQFNSTYRVVSVLTVLHQDWLNGKEYKCKV SNKGLPSSIEKTISKAKGQPREPQVYTLPPSQEEMTKNQVSLTCLVK GFYPSDIAVEWESNGQPENNYKTTPPVLDSDGSFFLYSRLTVDKSR WQEGNVFSCSVMHEALHNHYTQKSLSLSLGK |
| 93 (TMEB757 HC) | EVQLLESGGGLVQPGGSLRLSCAASGFTFSSYSMSWVRQAPGKGLE WVSVISGSGGFTDYADSVKGRFTISRDNSKNTLYLHMNSLRAEDTA VYYCARMPLNSPHDYWGQGTLVTVSSASTKGPSVFPLAPCSRSTSE STAALGCLVKDYFPEPVTVSWNSGALTSGVHTFPAVLQSSGLYSLS SVVTVPSSSLGTKTYTCNVDHKPSNTKVDKRVESKYGPPCPPCPAPE AAGGPSVFLFPPKPKDTLMISRTPEVTCVVVDVSQEDPEVQFNWYV DGVEVHNAKTKPREEQFNSTYRVVSVLTVLHQDWLNGKEYKCKV SNKGLPSSIEKTISKAKGQPREPQVYTLPPSQEEMTKNQVSLTCLVK GFYPSDIAVEWESNGQPENNYKTTPPVLDSDGSFFLYSRLTVDKSR WQEGNVFSCSVMHEALHNHYTQKSLSLSLGK |

TABLE 12

| LC PROTIEN SEQ ID NO: | LC AMINO ACID SEQUENCE |
|---|---|
| 35 (TMEB675 LC) | AIQMTQSPSSLSASVGDRVTITCRASQGIRNDLGWYQQKPGKAPKLLI YAASSLQSGVPSRFSGSGSGTDFTLTISSLQPEDFATYYCLQDYNYAL TFGGGTKVEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGEC |
| 36 (TMEB570 LC) | EIVLTQSPGTLSLSPGERATLSCRASQSVSTYYLAWYQQKPGQAPRLLI YGASYRATGIPDRFSGSGSGTDFTLTISRLEPEDFAVYYCQQYGHSPIT FGQGTKVEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |
| 37 (TMEB674 LC) | AIQMTQSPSSLSASVGDRVTITCRASQGIRNDLGWYQQKPGKAPKLLI YAASSLQSGVPSRFSGSGSGTDFTLTISSLQPEDFATYYCLQDYNYSLT FGGGTKVEIRRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |
| 38 (TMEB565 LC) | EIVLTQSPGTLSLSPGERATLSCRASQSVATYYLAWYQQKPGQAPRLL IYGASSRATGIPDRFSGSGSGTDFTLTISRLEPEDFAVYYCQQYGYNPI TFGQGTKVEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGEC |
| 92 (TMEB762 LC) | DIQMTQSPSSLSASVGDRVTITCRASQGIRNDLGWYQQKPGKAPKLLI YAASSLQSGVPSRFSGSGSGTDFTLTISSLQPEDFATYYCLQDYNYPLT FGGGTKVEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |
| 94 (TMEB757 LC) | AIQMTQSPSSLSASVGDRVTITCRASQGIRNDLGWYQQKPGKAPKLLI YAASSLQSGVPSRFSGSGSGTDFTLTISSLQPEDFATYYCLQDYNYPLT FGGGTKVEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |

TABLE 13

| Antibody | VH cDNA SEQ ID NO: | VL cDNA SEQ ID NO: | HC cDNA SEQ ID NO: | LC cDNA SEQ ID NO: |
|---|---|---|---|---|
| TMEB675 | 39 | 42 | 46 | 49 |
| TMEB570 | 40 | 43 | 47 | 50 |
| TMEB674 | 41 | 44 | 48 | 51 |
| TMEB565 | 40 | 45 | 47 | 52 |
| TMEB762 | 95 | 96 | 97 | 98 |
| TMEB757 | 99 | 100 | 101 | 102 |

(TMEB675 VH cDNA)
SEQ ID NO: 39
GAGGTGCAGCTGCTGGAAAGCGGCGGAGGCCTGGTGCAGAGAGGAGGAAG

CCTGAGACCCAGCTGTGCCGCCAGCGGCTTCACCTTCAGCAGCTACAGCA

TGAGCTGGGTCAGGCAGGCCCCTGGCAAAGGACTGGAGTGGGTGAGCGTG

ATTAGCGGCAGCGGCGGCTTCACCGATTACGCCGACAGCGTGAAGGGCAG

GTTCACCATCAGCAGGGACAATAGCAAGAACACCCTGTACCTGCACATGA

ACAGCCTGAGGGCCGAGGACACCGCCGTGTACTACTGCGCCAGGATGCCC

CTGAACAGCCCTCACGACTACTGGGGCCAGGGAACCCTGGTGACCGTGTC

CAGC (TMEB570, TMEB565 VH cDNA)
SEQ ID NO: 40
CAGGTGCAGCTGGTGCAGAGCGGCGCGGAAGTGAAAAAACCGGGCAGCAG

-continued
CGTGAAAGTGAGCTGCAAAGCGAGCGGCGGCACCTTCAGCTCCTATTACA

TTAGCTGGGTGCGCCAGGCGCCGGGCCAGGGCCTGGAATGGATGGGTGGC

ATTATCCCAATCAGTGGGCGTGCTAATTATGCGCAGAAATTTCAGGGCCG

CGTGACCATTACCGCTGATGAAAGCACCAGCACCGCGTATATGGAACTGA

GCAGCCTGCGCAGCGAAGATACCGCGGTGTATTATTGCGCGCGCGACGGC

TACAGTAGTGGACGTAGCACAACATACGCATTTGACTATTGGGGCCAGGG

CACCCTGGTGACCGTGTCGAGT (TMEB674 VH cDNA)
SEQ ID NO: 41
GAAGTGCAGCTGCTGGAGAGCGGAGGAGGACTGGTGCAGCCTCCTGGCGG

AAGCCTGAGACTGAGCTGCGCCGCTAGCGGCTTCACCTTCAGCAGCTACA

GCATGAGCTGGGTGAGACAGGCTCCTGGCAAGGGCCTGGAGTGGGTGAGC

GTGATCAGCGGCGGAGGCAGCTTTACCAGCTACGCCGACAGCGTGAAGGG

CAGGTTCACCATCAGCAGGGACAACAGCAACAACACCCTGTACCTGCAGA

TGAGCAGCCTGAGGGCCGAGGACACCGCCTTCTACTACTGCGCCAGGATG

CCCCTGAACAGCCCCCATGACTGCTGGGGACAGGGCACCCTGGTGACCGT

GAGCAGC (TMEB675 VL cDNA)
SEQ ID NO: 42
GCCATCCAGATGACCCAGAGCCCTAGCAGCCTGAGCGCTAGCGTGGGCGA

-continued

CAGGGTGACCATCACCTGCAGGGCCAGCCAGGGCATCAGAAACGACCTGG

GCTGGTACCAGCAGAAGCCCGGCAAGGCCCCCAAGCTGCTGATCTACGCC

GCCAGCAGCCTGCAGAGCGGAGTGCCTAGCAGGTTCAGCGGAAGCGGCAG

CGGCACCGACTTCACCCTGACCATCAGCAGCCTGCAGCCCGAGGACTTCG

CCACCTACTACTGCCTGCAGGACTACAACTACGCCCTGACATTCGGCGGC

GGCACCAAGGTGGAGATCAAG (TMEB570 VL cDNA)

SEQ ID NO: 43

GAAATTGTGCTGACCCAGAGCCCGGGCACCCTGAGCCTGAGCCCGGGCGA

ACGCGCGACCCTGAGCTGCCGCGCGAGCCAGAGCGTTTCCACATACTACC

TGGCGTGGTATCAGCAGAAACCGGGCCAGGCGCCGCGCCTGCTGATTTAC

GGTGCCTCCTATCGCGCGACCGGCATTCCGGATCGCTTTAGCGGCAGCGG

TTCCGGCACCGATTTTACCCTGACCATTAGCCGCCTGGAACCGGAAGATT

TTGCGGTGTATTATTGCCAGCAGTACGGTCACAGCCCGATTACTTTTGGC

CAGGGCACCAAAGTGGAAATCAAA (TMEB674 VL cDNA)

SEQ ID NO: 44

GCCATCCAGATGACCCAGAGCCCTAGCAGCCTGAGCGCTAGCGTGGGCGA

CAGGGTGACCATCACCTGCAGGGCCAGCCAGGGCATCAGGAACGACCTGG

GCTGGTACCAGCAGAAGCCCGGCAAGGCCCCCAAGCTGCTGATCTACGCC

GCCAGCAGCCTGCAGAGCGGAGTGCCTAGCAGGTTCAGCGGCAGCGGAAG

CGGCACCGACTTCACCCTGACCATCTCCAGCCTGCAGCCCGAGGACTTCG

CCACCTACTACTGCCTGCAGGACTACAACTACAGCCTGACCTTCGGCGGC

GGCACCAAGGTGGAGATCAGG (TMEB565 VL cDNA)

SEQ ID NO: 45

GAAATTGTGCTGACCCAGAGCCCGGGCACCCTGAGCCTGAGCCCGGGCGA

ACGCGCGACCCTGAGCTGCCGCGCGAGCCAGAGCGTTGCCACCTATTATC

TTGCGTGGTATCAGCAGAAACCGGGCCAGGCGCCGCGCCTGCTGATTTAC

GGTGCATCCTCCCGTGCGACCGGCATTCCGGATCGCTTTAGCGGCAGCGG

TTCCGGCACCGATTTTACCCTGACCATTAGCCGCCTGGAACCGGAAGATT

TTGCGGTGTATTATTGCCAGCAGTACGGCTATAACCCAATTACCTTTGGC

CAGGGCACCAAAGTGGAAATCAAA (TMEB675 HC cDNA)

SEQ ID NO: 46

GAGGTGCAGCTGCTGGAAAGCGGCGGAGGCCTGGTGCAGAGAGGAGGAAG

CCTGAGACCCAGCTGTGCCGCCAGCGGCTTCACCTTCAGCAGCTACAGCA

TGAGCTGGGTCAGGCAGGCCCCTGGCAAAGGACTGGAGTGGGTGAGCGTG

ATTAGCGGCAGCGGCGGCTTCACCGATTACGCCGACAGCGTGAAGGGCAG

GTTCACCATCAGCAGGGACAATAGCAAGAACACCCTGTACCTGCACATGA

ACAGCCTGAGGGCCGAGGACACCGCCGTGTACTACTGCGCCAGGATGCCC

CTGAACAGCCCTCACGACTACTGGGGCCAGGGAACCCTGGTGACCGTGTC

CAGCGCTTCCACCAAGGGCCCATCCGTCTTCCCCCTGGCGCCCTGCTCCA

GGAGCACCTCCGAGAGCACAGCCGCCCTGGGCTGCCTGGTCAAGGACTAC

TTCCCCGAACCGGTGACGGTGTCGTGGAACTCAGGCGCCCTGACCAGCGG

CGTGCACACCTTCCCGGCTGTCCTACAGTCCTCAGGACTCTACTCCCTCA

GCAGCGTGGTGACCGTGCCCTCCAGCAGCTTGGGCACGAAAACCTACACC

TGCAACGTAGATCACAAGCCCAGCAACACCAAGGTGGACAAGAGAGTTGA

GTCCAAATATGGTCCCCCATGCCCACCATGCCCAGCACCTGAGGCCGCCG

GGGGACCATCAGTCTTCCTGTTCCCCCCAAAACCCAAGGACACTCTCATG

ATCTCCCGGACCCCTGAGGTCACGTGCGTGGTGGTGGACGTGAGCCAGGA

AGACCCCGAGGTCCAGTTCAACTGGTACGTGGATGGCGTGGAGGTGCATA

ATGCCAAGACAAAGCCGCGGGAGGAGCAGTTCAACAGCACGTACCGTGTG

GTCAGCGTCCTCACCGTCCTGCACCAGGACTGGCTGAACGGCAAGGAGTA

CAAGTGCAAGGTCTCCAACAAAGCCTCCCGTCCTCCATCGAGAAAACCA

TCTCCAAAGCCAAAGGGCAGCCCCGAGAGCCACAGGTGTACACCCTGCCC

CCATCCCAGGAGGAGATGACCAAGAACCAGGTCAGCCTGACCTGCCTGGT

CAAAGGCTTCTACCCCAGCGACATCGCCGTGGAGTGGGAGAGCAATGGGC

AGCCGGAGAACAACTACAAGACCACGCCTCCCGTGCTGGACTCCGACGGC

TCCTTCTTCCTCTACAGCAGGCTAACCGTGGACAAGAGCAGGTGGCAGGA

GGGGAATGTCTTCTCATGCTCCGTGATGCATGAGGCTCTGCACAACCACT

ACACACAGAAGAGCCTCTCCCTGTCTCTGGGTAAA (TMEB570, TMEB565 HC cDNA)

SEQ ID NO: 47

CAGGTGCAGCTGGTGCAGAGCGGCGCGGAAGTGAAAAAACCGGGCAGCAG

CGTGAAAGTGAGCTGCAAAGCGAGCGGCGGCACCTTCAGCTCCTATTACA

TTAGCTGGGTGCGCCAGGCGCCGGGCCAGGGCCTGGAATGGATGGGTGGC

ATTATCCCAATCAGTGGGCGTGCTAATTATGCGCAGAAATTTCAGGGCCG

CGTGACCATTACCGCTGATGAAAGCACCAGCACCGCGTATATGGAACTGA

GCAGCCTGCGCAGCGAAGATACCGCGGTGTATTATTGCGCGCGCGACGGC

TACAGTAGTGGACGTAGCACAACATACGCATTTGACTATTGGGGCCAGGG

CACCCTGGTGACCGTGTCGAGTGCTTCCACCAAGGGCCCATCCGTCTTCC

CCCTGGCGCCCTGCTCCAGGAGCACCTCCGAGAGCACAGCCGCCCTGGGC

TGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCTTG

GGCACGAAAACCTACACCTGCAACGTAGATCACAAGCCCAGCAACACCAA

GGTGGACAAGAGAGTTGAGTCCAAATATGGTCCCCCATGCCCACCATGCC

CAGCACCTGAGGCCGCCGGGGGACCATCAGTCTTCCTGTTCCCCCCAAAA

CCCAAGGACACTCTCATGATCTCCCGGACCCCTGAGGTCACGTGCGTGGT

GGTGGACGTGAGCCAGGAAGACCCCGAGGTCCAGTTCAACTGGTACGTGG

ATGGCGTGGAGGTGCATAATGCCAAGACAAAGCCGCGGGAGGAGCAGTTC

AACAGCACGTACCGTGTGGTCAGCGTCCTCACCGTCCTGCACCAGGACTG

GCTGAACGGCAAGGAGTACAAGTGCAAGGTCTCCAACAAAGCCTCCCGT

CCTCCATCGAGAAAACCATCTCCAAAGCCAAAGGGCAGCCCCGAGAGCCA

CAGGTGTACACCCTGCCCCCATCCCAGGAGGAGATGACCAAGAACCAGGT

-continued

CAGCCTGACCTGCCTGGTCAAAGGCTTCTACCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTACAGCAGGCTAACCGTGGA

CAAGAGCAGGTGGCAGGAGGGGAATGTCTTCTCATGCTCCGTGATGCATG

AGGCTCTGCACAACCACTACACACAGAAGAGCCTCTCCCTGTCTCTGGGT

AAA (TMEB674 HC cDNA)

SEQ ID NO: 48
GAAGTGCAGCTGCTGGAGAGCGGAGGAGGACTGGTGCAGCCTCCTGGCGG

AAGCCTGAGACTGAGCTGCGCCGCTAGCGGCTTCACCTTCAGCAGCTACA

GCATGAGCTGGGTGAGACAGGCTCCTGGCAAGGGCCTGGAGTGGGTGAGC

GTGATCAGCGGCGGAGGCAGCTTTACCAGCTACGCCGACAGCGTGAAGGG

CAGGTTCACCATCAGCAGGGACAACAGCAACAACACCCTGTACCTGCAGA

TGAGCAGCCTGAGGGCCGAGGACACCGCCTTCTACTACTGCGCCAGGATG

CCCCTGAACAGCCCCCATGACTGCTGGGGACAGGGCACCCTGGTGACCGT

GAGCAGCGCTTCCACCAAGGGCCCATCCGTCTTCCCCCTGGCGCCCTGCT

CCAGGAGCACCTCCGAGAGCACAGCCGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCTTGGGCACGAAAACCTAC

ACCTGCAACGTAGATCACAAGCCCAGCAACACCAAGGTGGACAAGAGAGT

TGAGTCCAAATATGGTCCCCCATGCCCACCATGCCCAGCACCTGAGGCCG

CCGGGGGACCATCAGTCTTCCTGTTCCCCCCAAAACCCAAGGACACTCTC

ATGATCTCCCGGACCCCTGAGGTCACGTGCGTGGTGGTGGACGTGAGCCA

GGAAGACCCCGAGGTCCAGTTCAACTGGTACGTGGATGGCGTGGAGGTGC

ATAATGCCAAGACAAAGCCGCGGGAGGAGCAGTTCAACAGCACGTACCGT

GTGGTCAGCGTCCTCACCGTCCTGCACCAGGACTGGCTGAACGGCAAGGA

GTACAAGTGCAAGGTCTCCAACAAAGGCCTCCCGTCCTCCATCGAGAAAA

CCATCTCCAAAGCCAAAGGGCAGCCCCGAGAGCCACAGGTGTACACCCTG

CCCCCATCCCAGGAGGAGATGACCAAGAACCAGGTCAGCCTGACCTGCCT

GGTCAAAGGCTTCTACCCCAGCGACATCGCCGTGGAGTGGGAGAGCAATG

GGCAGCCGGAGAACAACTACAAGACCACGCCTCCCGTGCTGGACTCCGAC

GGCTCCTTCTTCCTCTACAGCAGGCTAACCGTGGACAAGAGCAGGTGGCA

GGAGGGGAATGTCTTCTCATGCTCCGTGATGCATGAGGCTCTGCACAACC

ACTACACACAGAAGAGCCTCTCCCTGTCTCTGGGTAAA (TMEB675 LC cDNA)

SEQ ID NO: 49
GCCATCCAGATGACCCAGAGCCCTAGCAGCCTGAGCGCTAGCGTGGGCGA

CAGGGTGACCATCACCTGCAGGGCCAGCCAGGGCATCAGAAACGACCTGG

GCTGGTACCAGCAGAAGCCCGGCAAGGCCCCCAAGCTGCTGATCTACGCC

GCCAGCAGCCTGCAGAGCGGAGTGCCTAGCAGGTTCAGCGGAAGCGGCAG

CGGCACCGACTTCACCCTGACCATCAGCAGCCTGCAGCCCGAGGACTTCG

CCACCTACTACTGCCTGCAGGACTACAACTACGCCCTGACATTCGGCGGC

GGCACCAAGGTGGAGATCAAGCGTACGGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGT (TMEB570 LC cDNA)

SEQ ID NO: 50
GAAATTGTGCTGACCCAGAGCCCGGGCACCCTGAGCCTGAGCCCGGGCGA

ACGCGCGACCCTGAGCTGCCGCGCGAGCCAGAGCGTTTCCACATACTACC

TGGCGTGGTATCAGCAGAAACCGGGCCAGGCGCCGCGCCTGCTGATTTAC

GGTGCCTCCTATCGCGCGACCGGCATTCCGGATCGCTTTAGCGGCAGCGG

TTCCGGCACCGATTTTACCCTGACCATTAGCCGCCTGGAACCGGAAGATT

TTGCGGTGTATTATTGCCAGCAGTACGGTCACAGCCCGATTACTTTTGGC

CAGGGCACCAAAGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGT (TMEB674 LC cDNA)

SEQ ID NO: 51
GCCATCCAGATGACCCAGAGCCCTAGCAGCCTGAGCGCTAGCGTGGGCGA

CAGGGTGACCATCACCTGCAGGGCCAGCCAGGGCATCAGGAACGACCTGG

GCTGGTACCAGCAGAAGCCCGGCAAGGCCCCCAAGCTGCTGATCTACGCC

GCCAGCAGCCTGCAGAGCGGAGTGCCTAGCAGGTTCAGCGGCAGCGGAAG

CGGCACCGACTTCACCCTGACCATCTCCAGCCTGCAGCCCGAGGACTTCG

CCACCTACTACTGCCTGCAGGACTACAACTACAGCCTGACCTTCGGCGGC

GGCACCAAGGTGGAGATCAGGCGTACGGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGT (TMEB565 LC cDNA)

SEQ ID NO: 52
GAAATTGTGCTGACCCAGAGCCCGGGCACCCTGAGCCTGAGCCCGGGCGA

ACGCGCGACCCTGAGCTGCCGCGCGAGCCAGAGCGTTGCCACCTATTATC

TTGCGTGGTATCAGCAGAAACCGGGCCAGGCGCCGCGCCTGCTGATTTAC

GGTGCATCCTCCCGTGCGACCGGCATTCCGGATCGCTTTAGCGGCAGCGG

-continued

TTCCGGCACCGATTTTACCCTGACCATTAGCCGCCTGGAACCGGAAGATT

TTGCGGTGTATTATTGCCAGCAGTACGGCTATAACCCAATTACCTTTGGC

CAGGGCACCAAAGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGT (TMEB762 VH cDNA)
SEQ ID NO: 95
GAGGTGCAGCTGCTGGAAAGCGGCGGAGGCCTGGTGCAGCCCGGAGGAAG

CCTGAGACTCAGCTGTGCCGCCAGCGGCTTCACCTTCAGCAGCTACAGCA

TGAGCTGGGTCAGGCAGGCCCCTGGCAAAGGACTGGAGTGGGTGAGCGTG

ATTAGCGGCAGCGGCGGCTTCACCGATTACGCCGACAGCGTGAAGGGCAG

GTTCACCATCAGCAGGGACAATAGCAAGAACACCCTGTACCTGCAGATGA

ACAGCCTGAGGGCCGAGGACACCGCCGTGTACTACTGCGCCAGGATGCCC

CTGAACAGCCCTCACGACTACTGGGGCCAGGGAACCCTGGTGACCGTGTC

CAGC (TMEB762 VL cDNA)
SEQ ID NO: 96
GACATCCAGATGACCCAGAGCCCTAGCAGCCTGAGCGCTAGCGTGGGCGA

CAGGGTGACCATCACCTGCAGGGCCAGCCAGGGCATCAGAAACGACCTGG

GCTGGTACCAGCAGAAGCCCGGCAAGGCCCCCAAGCTGCTGATCTACGCC

GCCAGCAGCCTGCAGAGCGGAGTGCCTAGCAGGTTCAGCGGAAGCGGCAG

CGGCACCGACTTCACCCTGACCATCAGCAGCCTGCAGCCCGAGGACTTCG

CCACCTACTACTGCCTGCAGGACTACAACTACCCCCTGACATTCGGCGGC

GGCACCAAGGTGGAGATCAAG (TMEB762 HC cDNA)
SEQ ID NO: 97
GAGGTGCAGCTGCTGGAAAGCGGCGGAGGCCTGGTGCAGCCCGGAGGAAG

CCTGAGACTCAGCTGTGCCGCCAGCGGCTTCACCTTCAGCAGCTACAGCA

TGAGCTGGGTCAGGCAGGCCCCTGGCAAAGGACTGGAGTGGGTGAGCGTG

ATTAGCGGCAGCGGCGGCTTCACCGATTACGCCGACAGCGTGAAGGGCAG

GTTCACCATCAGCAGGGACAATAGCAAGAACACCCTGTACCTGCAGATGA

ACAGCCTGAGGGCCGAGGACACCGCCGTGTACTACTGCGCCAGGATGCCC

CTGAACAGCCCTCACGACTACTGGGGCCAGGGAACCCTGGTGACCGTGTC

CAGCGCTTCCACCAAGGGCCCATCCGTCTTCCCCCTGGCGCCCTGCTCCA

GGAGCACCTCCGAGAGCACAGCCGCCCTGGGCTGCCTGGTCAAGGACTAC

TTCCCCGAACCGGTGACGGTGTCGTGGAACTCAGGCGCCCTGACCAGCGG

CGTGCACACCTTCCCGGCTGTCCTACAGTCCTCAGGACTCTACTCCCTCA

GCAGCGTGGTGACCGTGCCCTCCAGCAGCTTGGGCACGAAAACCTACACT

TGCAACGTAGATCACAAGCCCAGCAACACCAAGGTGGACAAGAGAGTTGA

GTCCAAATATGGTCCCCCATGCCCACCATGCCCAGCACCTGAGGCCGCCG

GGGGACCATCAGTCTTCCTGTTCCCCCCAAAACCCAAGGACACTCTCATG

ATCTCCCGGACCCCTGAGGTCACGTGCGTGGTGGTGGACGTGAGCCAGGA

AGACCCCGAGGTCCAGTTCAACTGGTACGTGGATGGCGTGGAGGTGCATA

ATGCCAAGACAAAGCCGCGGGAGGAGCAGTTCAACAGCACGTACCGTGTG

GTCAGCGTCCTCACCGTCCTGCACCAGGACTGGCTGAACGGCAAGGAGTA

CAAGTGCAAGGTCTCCAACAAAGGCCTCCCGTCCTCCATCGAGAAAACCA

TCTCCAAAGCCAAAGGGCAGCCCCGAGAGCCACAGGTGTACACCCTGCCC

CCATCCCAGGAGGAGATGACCAAGAACCAGGTCAGCCTGACCTGCCTGGT

CAAAGGCTTCTACCCCAGCGACATCGCCGTGGAGTGGGAGAGCAATGGGC

AGCCGGAGAACAACTACAAGACCACGCCTCCCGTGCTGGACTCCGACGGC

TCCTTCTTCCTCTACAGCAGGCTAACCGTGGACAAGAGCAGATGGCAGGA

GGGGAATGTCTTCTCATGCTCCGTGATGCATGAGGCTCTGCACAACCACT

ACACACAGAAGAGCCTCTCCCTGTCTCTGGGTAAA (TMEB762 LC cDNA)
SEQ ID NO: 98
GACATCCAGATGACCCAGAGCCCTAGCAGCCTGAGCGCTAGCGTGGGCGA

CAGGGTGACCATCACCTGCAGGGCCAGCCAGGGCATCAGAAACGACCTGG

GCTGGTACCAGCAGAAGCCCGGCAAGGCCCCCAAGCTGCTGATCTACGCC

GCCAGCAGCCTGCAGAGCGGAGTGCCTAGCAGGTTCAGCGGAAGCGGCAG

CGGCACCGACTTCACCCTGACCATCAGCAGCCTGCAGCCCGAGGACTTCG

CCACCTACTACTGCCTGCAGGACTACAACTACCCCCTGACATTCGGCGGC

GGCACCAAGGTGGAGATCAAGCGTACGGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGTTAG (TMEB757 VH cDNA)
SEQ ID NO: 99
GAGGTGCAGCTGCTGGAAAGCGGCGGAGGCCTGGTGCAGCCCGGAGGAAG

CCTGAGACTCAGCTGTGCCGCCAGCGGCTTCACCTTCAGCAGCTACAGCA

TGAGCTGGGTCAGGCAGGCCCCTGGCAAAGGACTGGAGTGGGTGAGCGTG

ATTAGCGGCAGCGGCGGCTTCACCGATTACGCCGACAGCGTGAAGGGCAG

GTTCACCATCAGCAGGGACAATAGCAAGAACACCCTGTACCTGCACATGA

ACAGCCTGAGGGCCGAGGACACCGCCGTGTACTACTGCGCCAGGATGCCC

CTGAACAGCCCTCACGACTACTGGGGCCAGGGAACCCTGGTGACCGTGTC

CAGC (TMEB757 VL cDNA)
SEQ ID NO: 100
GCCATCCAGATGACCCAGAGCCCTAGCAGCCTGAGCGCTAGCGTGGGCGA

CAGGGTGACCATCACCTGCAGGGCCAGCCAGGGCATCAGAAACGACCTGG

GCTGGTACCAGCAGAAGCCCGGCAAGGCCCCCAAGCTGCTGATCTACGCC

```
GCCAGCAGCCTGCAGAGCGGAGTGCCTAGCAGGTTCAGCGGAAGCGGCAG

CGGCACCGACTTCACCCTGACCATCAGCAGCCTGCAGCCCGAGGACTTCG

CCACCTACTACTGCCTGCAGGACTACAACTACCCCCTGACATTCGGCGGC

GGCACCAAGGTGGAGATCAAG (TMEB757 HC cDNA)
                                          SEQ ID NO: 101
GAGGTGCAGCTGCTGGAAAGCGGCGGAGGCCTGGTGCAGCCCGGAGGAAG

CCTGAGACTCAGCTGTGCCGCCAGCGGCTTCACCTTCAGCAGCTACAGCA

TGAGCTGGGTCAGGCAGGCCCCTGGCAAAGGACTGGAGTGGGTGAGCGTG

ATTAGCGGCAGCGGCGGCTTCACCGATTACGCCGACAGCGTGAAGGGCAG

GTTCACCATCAGCAGGGACAATAGCAAGAACACCCTGTACCTGCACATGA

ACAGCCTGAGGGCCGAGGACACCGCCGTGTACTACTGCGCCAGGATGCCC

CTGAACAGCCCTCACGACTACTGGGGCCAGGGAACCCTGGTGACCGTGTC

CAGCGCTTCCACCAAGGGCCCATCCGTCTTCCCCCTGGCGCCCTGCTCCA

GGAGCACCTCCGAGAGCACAGCCGCCCTGGGCTGCCTGGTCAAGGACTAC

TTCCCCGAACCGGTGACGGTGTCGTGGAACTCAGGCGCCCTGACCAGCGG

CGTGCACACCTTCCCGGCTGTCCTACAGTCCTCAGGACTCTACTCCCTCA

GCAGCGTGGTGACCGTGCCCTCCAGCAGCTTGGGCACGAAAACCTACACT

TGCAACGTAGATCACAAGCCCAGCAACACCAAGGTGGACAAGAGAGTTGA

GTCCAAATATGGTCCCCCATGCCCACCATGCCCAGCACCTGAGGCCGCCG

GGGGACCATCAGTCTTCCTGTTCCCCCCAAAACCCAAGGACACTCTCATG

ATCTCCCGGACCCCTGAGGTCACGTGCGTGGTGGTGGACGTGAGCCAGGA

AGACCCCGAGGTCCAGTTCAACTGGTACGTGGATGGCGTGGAGGTGCATA

ATGCCAAGACAAAGCCGCGGGAGGAGCAGTTCAACAGCACGTACCGTGTG

GTCAGCGTCCTCACCGTCCTGCACCAGGACTGGCTGAACGGCAAGGAGTA

CAAGTGCAAGGTCTCCAACAAAGGCCTCCCGTCCTCCATCGAGAAAACCA

TCTCCAAAGCCAAAGGGCAGCCCCGAGAGCCACAGGTGTACACCCTGCCC

CCATCCCAGGAGGAGATGACCAAGAACCAGGTCAGCCTGACCTGCCTGGT

CAAAGGCTTCTACCCCAGCGACATCGCCGTGGAGTGGGAGAGCAATGGGC

AGCCGGAGAACAACTACAAGACCACGCCTCCCGTGCTGGACTCCGACGGC

TCCTTCTTCCTCTACAGCAGGCTAACCGTGGACAAGAGCAGATGGCAGGA

GGGGAATGTCTTCTCATGCTCCGTGATGCATGAGGCTCTGCACAACCACT

ACACACAGAAGAGCCTCTCCCTGTCTCTGGGTAAA (TMEB757 LC cDNA)
                                          SEQ ID NO: 102
GCCATCCAGATGACCCAGAGCCCTAGCAGCCTGAGCGCTAGCGTGGGCGA

CAGGGTGACCATCACCTGCAGGGCCAGCCAGGGCATCAGAAACGACCTGG

GCTGGTACCAGCAGAAGCCCGGCAAGGCCCCCAAGCTGCTGATCTACGCC

GCCAGCAGCCTGCAGAGCGGAGTGCCTAGCAGGTTCAGCGGAAGCGGCAG

CGGCACCGACTTCACCCTGACCATCAGCAGCCTGCAGCCCGAGGACTTCG

CCACCTACTACTGCCTGCAGGACTACAACTACCCCCTGACATTCGGCGGC

GGCACCAAGGTGGAGATCAAGCGTACGGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGTTAG
```

The frameworks for the select anti-TMEFF2 antibodies are shown in Table 14.

TABLE 14

| Antibody | VH framework | VH framework SEQ ID NO: | VL framework | VL framework SEQ ID NO: |
|---|---|---|---|---|
| TMEB675 | VH3_3-23 | 53 | VKI_L11 | 55 |
| TMEB570 | VH1_1-69 | 54 | VKIII_A27 | 56 |
| TMEB674 | VH3_3-23 | 53 | VKI_L11 | 55 |
| TMEB565 | VH1_1-69 | 54 | VKI_L11 | 55 |
| TMEB762 | VH3_3-23 | 53 | VKI_L11 | 55 |
| TMEB757 | VH3_3-23 | 53 | VKI_L11 | 55 |

```
(VH3_3-23 framework)
                                          SEQ ID NO: 53
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKWG

QGTLVTVSS (VH1_1-69 framework)
                                          SEQ ID NO: 54
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCAR (VKI_L11 framework)
                                          SEQ ID NO: 55
AIQMTQSPSSLSASVGDRVTITCRASQGIRNDLGWYQQKPGKAPKLLIYA

ASSLQSGVPSRFSGSGSGTDFTLTISSLQPEDFATYYCLQDYNYP (VKIII_A27 framework)
                                          SEQ ID NO: 56
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSP
```

Example 5. Epitope Mapping of Anti-TMEFF2 Antibodies

Epitope mapping of TMEB570 and TMEB675 was done using H/D exchange. TMEW1 (SEQ ID NO: 6) was used as source of TMEFF2 in these assays.

10 µg of TMEW1 in 130 µL of control buffer (50 mM phosphate, 100 mM sodium chloride at pH 7.4) was denatured by adding 130 µL of 4 M guanidine hydrochloride, 0.85 M TCEP buffer (final pH was 2.5) and incubating the mixture for 3 min at 10° C. The mixture was then subjected to on-column pepsin/protease XIII digestion using an in-house packed pepsin/protease XIII (w/w, 1:1) column (2.1× 30 mm). The resultant peptides were analyzed using an UPLC-MS system comprised of a Waters Acquity UPLC coupled to a Q Exactive™ Hybrid Quadrupole-Orbitrap Mass Spectrometer (Thermo). The peptides were separated on a 50×1 mm C8 column with a 16.5 min gradient from 2-34% solvent B (0.2% formic acid in acetonitrile). Solvent A was 0.2% formic acid in water. The injection valve and pepsin/protease XIII column and their related connecting tubings were kept inside a cooling box maintained at 10° C. The second switching valve, C8 column and their related connecting stainless steel tubings were inside another chilled circulating box maintained at −6° C. Peptide identification was done through searching MS/MS data against the TMEW1 sequence with Mascot. The mass tolerance for the precursor and product ions were 7 ppm ad 0.02 Da, respectively.

10 μL of TMEW1 (5 μg) or 10 μL of TMEW1 & TMEB570 or TMEB675 mixture (5 μg:15 μg) was incubated with 120 μL deuterium oxide labeling buffer (50 mM sodium phosphate, 100 mM sodium chloride at pH 7.4) for 0 s, 30 s, 360 s, 3600 s, or 14400 s at 10° C. Hydrogen/deuterium (H/D) exchange at each time point was performed in duplicate. Hydrogen/deuterium exchange was quenched by adding 130 μL of 4 M guanidine hydrochloride, 0.85 M TCEP buffer (final pH was 2.5). Subsequently, the quenched samples were subjected to on column pepsin/protease XIII digestion and LC-MS analysis as described above. The mass spectra were recorded in MS only mode.

Raw MS data was processed using HDX WorkBench, software for the analysis of H/D exchange MS data (Pascal et al., *J. Am. Soc. Mass Spectrom.* 2012, 23 (9), 1512-1521). The deuterium levels were calculated using the average mass difference between the deuterated peptide and its native form (t0). About 97-99% of the protein could be mapped to specific peptides. The deuterium buildup curves showed significant difference in slopes, over exchange time for the peptides.

TMEB570 epitope: TMEW1 showed a modest reduction in deuterium uptake at residues 235-249 (residue numbering according to SEQ ID NO: 2), e.g. residues HGKCEHSINMQEPSC (SEQ ID NO: 57) within the membrane proximal region were protected from H/D exchange upon binding to TMEB570.

TMEB675 epitope: TMEW1 showed a modest reduction in deuterium uptake at residues 252-268 (residue numbering according to SEQ ID NO: 2), e.g. residues DAGYTGQHCEKKDYSVL (SEQ ID NO: 58) within the membrane proximal region were protected from H/D/exchange upon binding to TMEB675.

TMEB570 TMEFF2 epitope residues thus encompassed HGKCEHSINMQEPSC (SEQ ID NO: 57) and TMEB675 epitope residues encompassed DAGYTGQHCEKKDYSVL (SEQ ID NO: 58). Both antibodies bound TMEFF2 within the membrane proximal region.

Example 6. Generation of Anti-CD3 Antibodies

The anti-CD3 antibody CD3B219 has been described in U.S. Pat. No. 9,850,310.

Additional anti-CD3 antibodies were generated by immunizing OmniRats (OMT™). The obtained hybridoma supernatants were screened for binding to human and cynomolgus CD3+ T lymphocytes, the clones isolated and sequenced, and in some cases further engineered. The anti-CD3 antibodies were cloned as various isotypes including effector-silent IgG4 with S228P, F234A and L235A mutations or as IgG1 with L234A, L235A, G237A, P238S, H268A, A330S and P331S mutations. Two anti-CD3 antibodies generated were named CD3B376 and CD3B450.

In vitro binding affinity of CD3B376 and CD3B450 to human T cells was determined by flow cytometry after crossing with antigen specific target arm. A preliminary study was carried out on human T cells to determine the saturation binding constant of an anti-CD3 tracer molecule (K$_d$T). A fixed concentration of the tracer ([T]) was then used in a competition binding assay with titrated concentrations of the test mAbs. The IC$_{50}$ (concentration at which 50% inhibition is achieved) value of the test molecule was used to determine the binding affinity (K$_d$) using the following formula: K$_d$=IC50/(1+([T]/K$_d$T)). Five human donors were used to determine the saturation binding constant (K$_d$T) of the tracer, a commercially available AlexaFluor488 SP34-2 anti-CD3 (BioScience #557705) (data not shown).

Determining Saturation Binding Constant of Tracer (K$_d$T)

Methods: Human pan T cells were cryogenically-stored in nitrogen tanks until used. T cells were thawed, washed with PBS, re-suspended in FACS Staining buffer, counted (with viability noted), and re-suspended at 0.5×10$^6$ cells/mL. Far Red Live/Dead stain (Life Technologies, AKA Invitrogen #L34974) (50 μL of DMSO into a vial) was added at 1 μL per 1×10$^6$ cells; and FcR blocker (Miltenyi Biotec #130-059-901) (1 mL of a 1:20 dilution per 0.5×10$^6$ cells) were added to the cells for 10 minutes each. Cells were plated at 50,000 cells/well and washed. Increasing concentrations of the AlexaFluor488 SP-34 anti-CD3 were added to the T cells for 2 hours at 4° C. Cells were washed to remove un-bound antibody, fixed for 15 minutes, washed, and re-suspended in FACS Staining buffer containing 1 mM EDTA.

The iQue Intellicyte Flow Cytometer was used to measure binding. Cells were gated for T cell population, followed by cell singlets, followed by Live Cells (FL4). Geometric mean of staining (FL1) was determined for each well.

The acquired mean fluorescence intensity values were plotted as a function of the antibody molecule concentration and analyzed using Prism software in a one-site binding analysis (Total Binding). The software calculates the corresponding K$_d$ value that describes the binding of the antibody molecule to a receptor (the CD3 on Human Pan T cells) that follows the law of mass action. The formula is as follows: Y=(B$_{max}$×X)/(K$_d$+X); where: Bmax is maximal binding; K$_d$ is the concentration of ligand required to reach half-maximal binding.

Results: K$_d$ values were derived for each donor, and the mean value obtained. The Saturation Binding Constant (K$_d$T) for human T-Cells was derived to be 5.6±1.0 nM (n=4) and was used in the previously mentioned formula to determine K$_d$ binding affinities.

Determining Binding Affinity of Anti-CD3 mAbs by Competition Assay

Competition binding studies were performed using CD3B376 and CD3B450. Human pan T cells were used to determine the binding affinity of the mAbs. The tracer used was the commercially available AlexaFluor488 SP-34 anti-CD3 (BioScience #557705) and the saturation binding constant for this tracer is described above.

T cells were cryogenically-stored in nitrogen tanks until used. T cells were thawed, washed with PBS, re-suspended in FACS Staining buffer, counted with viability noted, and re-suspended at 0.5×10$^6$ cells/mL. Far Red Live/Dead stain (Life Technologies, AKA Invitrogen #L34974) (50 μL of DMSO into a vial) was added at 1 μL per 1×10$^6$ cells; and FcR blocker (Miltenyi Biotec #130-059-901) (1 mL of a 1:20 dilution per 0.5×10$^6$ cells) was added to the cells for 10 minutes each. Cells were plated at 50,000 cells/well and washed.

The mAbs (and isotype control), were serially diluted 1:2 from a starting concentration of 1000 or 200 μg/mL (2×), and a fixed concentration of the tracer (5 μg/mL; 2×) was mixed together to give 1× concentrations. Therefore, the final (1×) concentration of the tracer was 2.5 μg/mL=16.6 nM. The mixture was added to the T cells for 2 hours at 4° C. Cells were then washed to remove un-bound antibody, fixed for 15 minutes, washed, and re-suspended in FACS Staining buffer containing 1 mM EDTA.

The iQue Intellicyte Flow Cytometer was used to measure binding. Cells were gated for T-cell population, followed by cell singlets, followed by Live Cells (FL4). Geometric mean of staining (FL1) was determined for each well. The acquired mean fluorescence intensity values were plotted as a function of the log antibody molecule concentration (converted to nM) and analyzed using Prism software in a sigmoidal dose-response (variable slope) from which the EC50/IC50 values (in nM) are derived. The binding affinity ($K_d$) was derived using the following formula: $K_d = IC50/(1+([T]/K_dT))$. Where: $K_d$ is the affinity of the competitor (unlabeled molecule); IC50 in nM of the test compound; [T] is concentration of the tracer (16.6 nM); $K_dT$ is the $K_d$ of the tracer determined by saturation binding (5.6 nM for human).

The CD3B376 binding site was tighter than the CD3B450 in both bivalent and monovalent form.

TABLE 15

| Construct | anti CD3 | IC50 (nM) | $K_d$ (nM) |
|---|---|---|---|
| Bivalent | CD3B376 | 29 | 7.3 |
|  | CD3B450 | 60 | 15 |
| Monovalent Construct | CD3B376 | 409 | 103 |
|  | CD3B450 | 1011 | 254 |

The CDR, VH and VL amino acid sequences of CD3B219, CD3B376 and CD3B450 are shown in Table 16.

TABLE 16

| Antibody | Region | Amino acid sequence | SEQ ID NO: |
|---|---|---|---|
| CD3B219 | HCDR1 | TYAMN | 60 |
|  | HCDR2 | RIRSKYNNYATYYAASVKG | 61 |
|  | HCDR3 | HGNFGNSYVSWFAY | 62 |
|  | LICDR1 | RSSTGAVTTSNYAN | 63 |
|  | LCDR2 | GTNKRAP | 64 |
|  | LCDR3 | ALWYSNLWV | 65 |
|  | VH (CD3B219VH) | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 66 |
|  | VL (CD3B219VL) | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 67 |
| CD3B376 | HCDR1 | NNNAAWS | 68 |
|  | HCDR2 | RTYYRSKWLYDYAVSVKS | 69 |
|  | HCDR3 | GYSSSFDY | 70 |
|  | LICDR1 | TGTSSNIGTYKFVS | 71 |
|  | LCDR2 | EVSKRPS | 72 |
|  | LCDR3 | VSYAGSGTLL | 73 |
|  | VH (CD3H219) | QVQLQQSGPRLVRPSQTLSLTCAISGDSVFNNNAAWSWIRQSPSRGLEWLGRTYYRSKWLYDYAVSVKSRITVNPDTSRNQFTLQLNSVTPEDTALYYCARGYSSSFDYWGQGTLVTVSS | 74 |
|  | VL (CD3L150) | QSALTQPASVSGSPGQSITISCTGTSSNIGTYKFVSWYQQHPDKAPKVLLYEVSKRPSGVSSRFSGSKSGNTASLTISGLQAEDQADYHCVSYAGSGTLLFGGGTKLTVL | 75 |
| CD3B450 | HCDR1 | NNNAAWS | 68 |
|  | HCDR2 | RTYYRSKWLYDYAVSVKS | 69 |
|  | HCDR3 | GYSSSFDY | 70 |
|  | LICDR1 | TGTSSNIGTYKFVS | 71 |
|  | LCDR2 | EVSKRPS | 72 |
|  | LCDR3 | VSYAGSGTLL | 73 |
|  | VH (CD3H231) | QVQLQQSGPGLVKPSQTLSLTCAISGDSVFNNNAAWSWIRQSPSRGLEWLGRTYYRSKWLYDYAVSVKSRITINPDTSKNQFSLQLNSVTPEDTAVYYCARGYSSSFDYWGQGTLVTVSS | 59 |
|  | VL (CD3L197) | QSALTQPASVSGSPGQSITISCTGTSSNIGTYKFVSWYQQHPGKAPKVMIYEVSKRPSGVSNRFSGSKSGNTASLTISGLQAEDEADYYCVSYAGSGTLLFGGGTKLTVL | 111 |

CD3B219 HC; (IgG4 S228P, F234A, L235A, F405L and R409K)

SEQ ID NO: 76

EVQLVESGGGLVQPGGSLRLSCAASGFTFNTYAMNWVRQAPGKGLEWVAR

IRSKYNNYATYYAASVKGRFTISRDDSKNSLYLQMNSLKTEDTAVYYCAR

HGNFGNSYVSWFAYWGQGTLVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEAAGGPSVFLFPP

-continued

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFLLYSKLTVDKSRWQEGNVFSCSVMHEALHNHYTQKSLSLSL

GK

CD3B219 LC

SEQ ID NO: 77

QTVVTQEPSLTVSPGGTVTLTCRSSTGAVTTSNYANWVQQKPGQAPRGLI

GGTNKRAPGTPARFSGSLLGGKAALTLSGVQPEDEAEYYCALWYSNLWVF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

CD3B376 HC (IgG4 S228P, F234A, L235A, F405L
and R409K)

SEQ ID NO: 78

QVQLQQSGPRLVRPSQTLSLTCAISGDSVFNNNAAWSWIRQSPSRGLEWL

GRTYYRSKWLYDYAVSVKSRITVNPDTSRNQFTLQLNSVTPEDTALYYCA

RGYSSSFDYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEAAGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFLLYSKLTVDKSRWQEGNVFSCSVMHEALHNHYTQKSLSLSLGK

CD3B376 LC

SEQ ID NO: 79

QSALTQPASVSGSPGQSITISCTGTSSNIGTYKFVSWYQQHPDKAPKVLL

YEVSKRPSGVSSRFSGSKSGNTASLTISGLQAEDQADYHCVSYAGSGTLL

FGGGTKLTVLGQPKAAPSVTLFPPSSEELQANKATLVCLISDFYPGAVTV

AWKADSSPVKAGVETTTPSKQSNNKYAASSYLSLTPEQWKSHRSYSCQVT

HEGSTVEKTVAPTECS

Table 17 shows the SEQ ID NOs: of polynucleotides encoding anti-CD3 antibody chains

TABLE 17

| Antibody | VH cDNA SEQ ID NO: | VL cDNA SEQ ID NO: | HC cDNA SEQ ID NO: | LC cDNA SEQ ID NO: |
| --- | --- | --- | --- | --- |
| CD3B219 | 105 | 106 | 80 | 81 |
| CD3B376 | 107 | 108 | 82 | 83 |

CD3B219 VH cDNA

SEQ ID NO: 105

GAAGTGCAGCTGGTGGAATCTGGCGGCGGACTGGTGCAGCCTGGCGGATC

TCTGAGACTGAGCTGTGCCGCCAGCGGCTTCACCTTCAACACCTACGCCA

TGAACTGGGTGCGCCAGGCCCCTGGCAAAGGCCTGGAATGGGTGGCCCGG

ATCAGAAGCAAGTACAACAATTACGCCACCTACTACGCCGCCTCCGTGAA

GGGCAGATTCACCATCAGCCGGGACGACAGCAAGAACAGCCTGTACCTGC

AGATGAACTCCCTGAAAACCGAGGACACCGCCGTGTACTACTGCGCCAGA

CACGGCAACTTCGGCAACAGCTATGTGTCTTGGTTTGCCTACTGGGGCCA

GGGCACCCTCGTGACCGTGTCATCT

CD3B219 VL cDNA

SEQ ID NO: 106

CAGACCGTCGTGACCCAGGAACCTAGCCTGACCGTGTCTCCTGGCGGCAC

CGTGACCCTGACCTGCAGATCTTCTACAGGCGCCGTGACCACCAGCAACT

ACGCCAACTGGGTGCAGCAGAAGCCAGGCCAGGCTCCCAGAGGACTGATC

GGCGGCACCAACAAGAGAGCCCCTGGCACCCCTGCCAGATTCAGCGGATC

TCTGCTGGGAGGAAAGGCCGCCCTGACACTGTCTGGCGTGCAGCCTGAAG

ATGAGGCCGAGTACTACTGCGCCCTGTGGTACAGCAACCTGTGGGTGTTC

GGCGGAGGCACCAAGCTGACAGTGCTG

CD3B219 HC cDNA

SEQ ID NO: 80

GAAGTGCAGCTGGTGGAATCTGGCGGCGGACTGGTGCAGCCTGGCGGATC

TCTGAGACTGAGCTGTGCCGCCAGCGGCTTCACCTTCAACACCTACGCCA

TGAACTGGGTGCGCCAGGCCCCTGGCAAAGGCCTGGAATGGGTGGCCCGG

ATCAGAAGCAAGTACAACAATTACGCCACCTACTACGCCGCCTCCGTGAA

GGGCAGATTCACCATCAGCCGGGACGACAGCAAGAACAGCCTGTACCTGC

AGATGAACTCCCTGAAAACCGAGGACACCGCCGTGTACTACTGCGCCAGA

CACGGCAACTTCGGCAACAGCTATGTGTCTTGGTTTGCCTACTGGGGCCA

GGGCACCCTCGTGACCGTGTCATCTGCTTCCACCAAGGGCCCATCCGTCT

TCCCCCTGGCGCCCTGCTCCAGGAGCACCTCCGAGAGCACAGCCGCCCTG

GGCTGCCTGGTCAAGGACTACTTCCCCGAACCGGTGACGGTGTCGTGGAA

CTCAGGCGCCCTGACCAGCGGCGTGCACACCTTCCCGGCTGTCCTACAGT

CCTCAGGACTCTACTCCCTCAGCAGCGTGGTGACCGTGCCCTCCAGCAGC

TTGGGCACGAAAACCTACACCTGCAACGTAGATCACAAGCCCAGCAACAC

CAAGGTGGACAAGAGAGTTGAGTCCAAATATGGTCCCCCATGCCCACCAT

GCCCAGCACCTGAGGCCGCCGGGGGACCATCAGTCTTCCTGTTCCCCCCA

AAACCCAAGGACACTCTCATGATCTCCCGGACCCCTGAGGTCACGTGCGT

GGTGGTGGACGTGAGCCAGGAAGACCCCGAGGTCCAGTTCAACTGGTACG

TGGATGGCGTGGAGGTGCATAATGCCAAGACAAAGCCGCGGGAGGAGCAG

TTCAACAGCACGTACCGTGTGGTCAGCGTCCTCACCGTCCTGCACCAGGA

CTGGCTGAACGGCAAGGAGTACAAGTGCAAGGTCTCCAACAAAGGCCTCC

CGTCCTCCATCGAGAAAACCATCTCCAAAGCCAAAGGGCAGCCCCGAGAG

CCACAGGTGTACACCCTGCCCCCATCCCAGGAGGAGATGACCAAGAACCA

GGTCAGCCTGACCTGCCTGGTCAAAGGCTTCTACCCCAGCGACATCGCCG

TGGAGTGGGAGAGCAATGGGCAGCCGGAGAACAACTACAAGACCACGCCT

CCCGTGCTGGACTCCGACGGCTCCTTCTTCCTCTACAGCAAGCTAACCGT

GGACAAGAGCAGGTGGCAGGAGGGGAATGTCTTCTCATGCTCCGTGATGC

ATGAGGCTCTGCACAACCACTACACACAGAAGAGCCTCTCCCTGTCTCTG

GGTAAA

CD3B219 LC cDNA

SEQ ID NO: 81

CAGACCGTCGTGACCCAGGAACCTAGCCTGACCGTGTCTCCTGGCGGCAC
CGTGACCCTGACCTGCAGATCTTCTACAGGCGCCGTGACCACCAGCAACT
ACGCCAACTGGGTGCAGCAGAAGCCAGGCCAGGCTCCCAGAGGACTGATC
GGCGGCACCAACAAGAGAGCCCCTGGCACCCCTGCCAGATTCAGCGGATC
TCTGCTGGGAGGAAAGGCCGCCCTGACACTGTCTGGCGTGCAGCCTGAAG
ATGAGGCCGAGTACTACTGCGCCCTGTGGTACAGCAACCTGTGGGTGTTC
GGCGGAGGCACCAAGCTGACAGTGCTGGGTCAGCCCAAGGCTGCACCCAG
TGTCACTCTGTTCCCGCCCTCCTCTGAGGAGCTTCAAGCCAACAAGGCCA
CACTGGTGTGTCTCATAAGTGACTTCTACCCGGGAGCCGTGACAGTGGCC
TGGAAGGCCGATAGCAGCCCCGTCAAGGCGGGAGTGGAGACCACCACACC
CTCCAAACAAAGCAACAACAAGTACGCGGCCAGCAGCTATCTGAGCCTGA
CGCCTGAGCAGTGGAAGTCCCACAGAAGCTACAGCTGCCAGGTCACGCAT
GAAGGGAGCACCGTGGAGAAGACAGTGGCCCCTACAGAATGTTCA

CD3B376 VH cDNA

SEQ ID NO: 107

CAGGTGCAGCTGCAGCAGTCTGGCCCTAGACTCGTGCGGCCTTCCCAGAC
CCTGTCTCTGACCTGTGCCATCTCCGGCGACTCCGTGTTCAACAACAACG
CCGCCTGGTCCTGGATCCGGCAGAGCCCTTCTAGAGGCCTGGAATGGCTG
GGCCGGACCTACTACCGGTCCAAGTGGCTGTACGACTACGCCGTGTCCGT
GAAGTCCCGGATCACCGTGAACCCTGACACCTCCCGGAACCAGTTCACCC
TGCAGCTGAACTCCGTGACCCCTGAGGACACCGCCCTGTACTACTGCGCC
AGAGGCTACTCCTCCTCCTTCGACTATTGGGGCCAGGGCACCCTCGTGAC
CGTGTCCTCT

CD3B376 VL cDNA

SEQ ID NO: 108

AGTCTGCTCTGACCCAGCCTGCCTCCGTGTCTGGCTCTCCCGGCCAGTCC
ATCACCATCAGCTGTACCGGCACCTCCTCCAACATCGGCACCTACAAGTT
CGTGTCCTGGTATCAGCAGCACCCCGACAAGGCCCCCAAAGTGCTGCTGT
ACGAGGTGTCCAAGCGGCCCTCTGGCGTGTCCTCCAGATTCTCCGGCTCC
AAGTCTGGCAACACCGCCTCCCTGACCATCAGCGGACTGCAGGCTGAGGA
CCAGGCCGACTACCACTGTGTGTCCTACGCTGGCTCTGGCACCCTGCTGT
TTGGCGGAGGCACCAAGCTGACCGTGCTG

CD3B376 HC cDNA

SEQ ID NO: 82

CAGGTGCAGCTGCAGCAGTCTGGCCCTAGACTCGTGCGGCCTTCCCAGAC
CCTGTCTCTGACCTGTGCCATCTCCGGCGACTCCGTGTTCAACAACAACG
CCGCCTGGTCCTGGATCCGGCAGAGCCCTTCTAGAGGCCTGGAATGGCTG
GGCCGGACCTACTACCGGTCCAAGTGGCTGTACGACTACGCCGTGTCCGT
GAAGTCCCGGATCACCGTGAACCCTGACACCTCCCGGAACCAGTTCACCC
TGCAGCTGAACTCCGTGACCCCTGAGGACACCGCCCTGTACTACTGCGCC
AGAGGCTACTCCTCCTCCTTCGACTATTGGGGCCAGGGCACCCTCGTGAC
CGTGTCCTCTGCTTCCACCAAGGGCCCATCCGTCTTCCCCCTGGCGCCCT
GCTCCAGGAGCACCTCCGAGAGCACAGCCGCCCTGGGCTGCCTGGTCAAG
GACTACTTCCCCGAACCGGTGACGGTGTCGTGGAACTCAGGCGCCCTGAC
CAGCGGCGTGCACACCTTCCCGGCTGTCCTACAGTCCTCAGGACTCTACT
CCCTCAGCAGCGTGGTGACCGTGCCCTCCAGCAGCTTGGGCACGAAAACC
TACACCTGCAACGTAGATCACAAGCCCAGCAACACCAAGGTGGACAAGAG
AGTTGAGTCCAAATATGGTCCCCCATGCCCACCATGCCCAGCACCTGAGG
CCGCCGGGGGACCATCAGTCTTCCTGTTCCCCCCAAAACCCAAGGACACT
CTCATGATCTCCCGGACCCCTGAGGTCACGTGCGTGGTGGTGGACGTGAG
CCAGGAAGACCCCGAGGTCCAGTTCAACTGGTACGTGGATGGCGTGGAGG
TGCATAATGCCAAGACAAAGCCGCGGGAGGAGCAGTTCAACAGCACGTAC
CGTGTGGTCAGCGTCCTCACCGTCCTGCACCAGGACTGGCTGAACGGCAA
GGAGTACAAGTGCAAGGTCTCCAACAAAGGCCTCCCGTCCTCCATCGAGA
AAACCATCTCCAAAGCCAAAGGGCAGCCCCGAGAGCCACAGGTGTACACC
CTGCCCCCATCCCAGGAGGAGATGACCAAGAACCAGGTCAGCCTGACCTG
CCTGGTCAAAGGCTTCTACCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTAACCGTGGACAAGAGCAGGTG
GCAGGAGGGGAATGTCTTCTCATGCTCCGTGATGCATGAGGCTCTGCACA
ACCACTACACACAGAAGAGCCTCTCCCTGTCTCTGGGTAAA

CD3B376 LC cDNA

SEQ ID NO: 83

CAGTCTGCTCTGACCCAGCCTGCCTCCGTGTCTGGCTCTCCCGGCCAGTC
CATCACCATCAGCTGTACCGGCACCTCCTCCAACATCGGCACCTACAAGT
TCGTGTCCTGGTATCAGCAGCACCCCGACAAGGCCCCCAAAGTGCTGCTG
TACGAGGTGTCCAAGCGGCCCTCTGGCGTGTCCTCCAGATTCTCCGGCTC
CAAGTCTGGCAACACCGCCTCCCTGACCATCAGCGGACTGCAGGCTGAGG
ACCAGGCCGACTACCACTGTGTGTCCTACGCTGGCTCTGGCACCCTGCTG
TTTGGCGGAGGCACCAAGCTGACCGTGCTGGGTCAGCCCAAGGCTGCACC
CAGTGTCACTCTGTTCCCGCCCTCCTCTGAGGAGCTTCAAGCCAACAAGG
CCACACTGGTGTGTCTCATAAGTGACTTCTACCCGGGAGCCGTGACAGTG
GCCTGGAAGGCCGATAGCAGCCCCGTCAAGGCGGGAGTGGAGACCACCAC
ACCCTCCAAACAAAGCAACAACAAGTACGCGGCCAGCAGCTATCTGAGCC
TGACGCCTGAGCAGTGGAAGTCCCACAGAAGCTACAGCTGCCAGGTCACG
CATGAAGGGAGCACCGTGGAGAAGACAGTGGCCCCTACAGAATGTTCA

Example 7. Generation of Bispecific TMEFF2×CD3 Antibodies

Select monospecific anti-TMEFF2 and anti-CD3 antibodies were expressed as IgG4/κ. F405L and R409K substitutions (EU numbering) were made into the anti-CD3 antibodies while the anti-TMEFF2 antibodies had wild-type IgG4. In addition to position 405 and 409 substitutions, the IgG4 mAbs were engineered to have S228P, F234A and L235A substitution.

The monospecific antibodies were expressed and purified using standard methods using a Protein A column (HiTrap MabSelect SuRe column). After elution, the pools were dialyzed into D-PBS, pH 7.2.

Bispecific TMEFF2×CD3 antibodies were generated by combining a monospecific TMEFF2 mAb and a monospecific CD3 mAb in in vitro Fab arm exchange as described in Int. Patent Publ. No. WO2011/131746. Briefly, at about 1-20 mg/ml at a molar ratio of 1:1 of each antibody in PBS, pH 7-7.4 and 75 mM 2-mercaptoethanolamine (2-MEA) was mixed together and incubated at 25-37° C. for 2-6 h, followed by removal of the 2-MEA via dialysis, diafiltration, tangential flow filtration and/or spinned cell filtration using standard methods.

The bispecific antibodies were further purified after the in vitro Fab-arm exchange using hydrophobic interaction chromatography to minimize residual parental anti-TMEFF2 and anti-CD3 antibodies using standard methods.

Table 18 and Table 19 show the generated bispecific antibodies.

TABLE 18

| Bispecific antibody | Parental (TMEFF2 arm/CD3 arm) | HCDR1 | HCDR2 | HCDR3 | LCDR1 | LCDR2 | LCDR3 |
|---|---|---|---|---|---|---|---|
| TMCB93 | TMEB675 | 10 | 12 | 15 | 18 | 20 | 22 |
|  | CD3B219 | 60 | 61 | 62 | 63 | 64 | 65 |
| TMCB132 | TMEB675 | 10 | 12 | 15 | 18 | 20 | 22 |
|  | CD3B376 | 68 | 69 | 70 | 71 | 72 | 73 |
| TMCB101 | TMEB570 | 11 | 13 | 16 | 19 | 21 | 23 |
|  | CDB219 | 60 | 61 | 62 | 63 | 64 | 65 |
| TMCB131 | TMEB570 | 11 | 13 | 16 | 19 | 21 | 23 |
|  | CD3B376 | 68 | 69 | 70 | 71 | 72 | 73 |
| TMCB92 | TMEB674 | 10 | 14 | 17 | 18 | 20 | 24 |
|  | CD3B219 | 60 | 61 | 62 | 63 | 64 | 65 |
| TMCB102 | TMEB565 | 11 | 13 | 16 | 18 | 20 | 22 |
|  | CD3B219 | 60 | 61 | 62 | 63 | 64 | 65 |

TABLE 19

| Bispecific antibody | Parental (TMEFF2 arm/CD3 arm) | VH | VL | HC | LC |
|---|---|---|---|---|---|
| TMCB93 | TMEB675 | 25 | 28 | 32 | 35 |
|  | CD3B219 | 66 | 67 | 76 | 77 |
| TMCB132 | TMEB675 | 25 | 28 | 32 | 35 |
|  | CD3B376 | 74 | 75 | 78 | 79 |
| TMCB101 | TMEB570 | 26 | 29 | 33 | 36 |
|  | CDB219 | 66 | 67 | 76 | 77 |
| TMCB131 | TMEB570 | 26 | 29 | 33 | 36 |
|  | CD3B376 | 74 | 75 | 78 | 79 |
| TMCB92 | TMEB674 | 27 | 30 | 34 | 37 |
|  | CD3B219 | 66 | 67 | 76 | 77 |
| TMCB102 | TMEB565 | 26 | 31 | 33 | 38 |
|  | CD3B219 | 66 | 67 | 76 | 77 |

Example 8. Characterization of Bispecific TMEFF2×CD3 Antibodies

Purity Analysis by Analytical Ultra Centrifugation (AUC)

Analytical ultracentrifugation (AUC) allows for the determination of the size, shape, state of aggregation, and reversible interaction of macromolecules in solution. Sedimentation velocity (SV) is an AUC technique that allows for a concentration gradient of a macromolecule to move to the outer radius of the sample holder (cell) as the centrifuge spins. This enables the determination of the sedimentation coefficient which is a factor of the size and shape of a molecule, and it unique to each molecule. Beckman Optima AUC instrument was used for this purpose. The samples were loaded into centrifuge cells equipped with 1.2 cm Beckman centerpieces (rated to 50K rpm) and quartz windows. The cells are assembled and torqued to 130 lbs. The centrifuge cells were placed into an An-50 (8 hole) or An-60 (4 hole) rotor and placed within the AUC chamber. The temperature of the AUC was equilibrated to 20.5° C. for at least one hour with the rotor in the chamber before initiating the run. Runs were performed at 40K rpm for mAb sample with scan count (250 scans), frequency of scan collection (90 seconds), data resolution (10 µM), wavelength at 280 nm. The data were analyzed using the direct boundary fitting software SEDANAL. Purity of the bispecific antibody TMCB150 and its parental mAbs were measured. TMCB150 showed 97.1% monomer, 2.8% dimer monomer and no aggregation, as determined by AUC meeting acceptable criteria for transiently expressed research material for further biophysical characterization. TMEB762 showed 95.5% monomer, 4.5% dimer and no aggregation while CD3B376 showed 97.7% monomer and 2.2% dimer with no aggregation. Aggregate levels of >5% of a minimum two-step purified molecule could have a significant impact on biological activity, solubility, stability and shelf-life.

Conformational Stability of Anti-TMEFF2/CD3 Bispecific by DSC

TMCB150 thermal unfolding was determined by DSC (Differential Scanning Calorimetry) that showed an onset of unfolding Tm=52.6° C., the first thermal transition (Tm1) at 61.8° C., second thermal transition (Tm2) at 67.6° C. and third thermal transition (Tm3) at 75.5° C. Based on parental antibodies (anti-TMEFF2, TMEB762 and anti-CD3, CD3B376) thermal transition profile as assessed by DSC before, Tm1 of TMCB150 corresponds to CD3B376 FAB unfolding and Tm3 of TMCB150 corresponds to TMEB762 Fab unfolding transitions.

Serum Stability

Serum stability assay is developed to evaluate properties of lead candidates for non-specific or off-target binding to human serum components. This may be predictive of poor pharmacokinetics and bio distribution properties. Binding and stability of TMCB150 is evaluated in both buffer and human serum using a fluorescence-based chromatography method. Bispecific antibody is labeled with Alexa Fluor 488 conjugate (Invitrogen kit according to manufacturer's instructions), incubated in Hepes buffer and human serum (Sigma, cat #H4522) at 4° C. and 37° C. for 2 days and then analysed by SEC-HPLC using Agilent HPLC system equipped with fluorescence detector. Percent aggregate is calculated from the integration of area under the curve of each peak. TMCB150 showed 2.4% aggregation in Hepes buffer at time zero and 2.0% and 1.3% aggregation after two days at 40 and 37° Celcius, respectively. In human serum, TMCB150 showed 1,7% aggregation at time zero and 1.1% aggregation after two days at both 4° and 37° Celcius.

Non-Specific Binding

Non-specific binding of the lead molecule to unrelated surfaces is determined by biosensor technology (Biacore 8K). Antibody is passed over SPR surfaces coated with unrelated proteins. If the antibody displays significant binding to these irrelevant surfaces, its predicted to have poor in-vivo properties and exhibit manufacturing challenges. Lead molecule is tested at the final concentration of 1 μM. Irrelevant surfaces include negatively charged protein (Soy Trypsin Inhibitor), positively charged protein (Lysozyme and β-defensin), hydrophobic (Rh-integrin a4b7), human IgG, sticky protein (Rh-CD19). Proper controls are used in this experiment. Lead is flown over two surfaces, one is a blank and the other has a molecule directly immobilized. The response unit (RU) level is determined by subtracting the blank RU from the test surface RU. The RU of TMCB150 and the parental mAbs are given below in the table. A response unit ≥100 predicts high risks for non-specific binding to charged/hydrophobic/IgG surfaces which would create challenges during manufacturing and translate to poor PK properties. None of the antibodies show non-specific binding to irrelevant surfaces predicting low to no risks for manufacturing and in-vivo behavior.

TABLE 20

|  | STI | B-Defensin-3 | Human IgG | Lysozyme | rh-Integrin a4b7 | rh-CD19 |
| --- | --- | --- | --- | --- | --- | --- |
| TMCB150 | 1.6 | 6.4 | 7.5 | 4.2 | 0 | 3.4 |
| TMEB762 | 0 | 4.1 | 8.4 | 4.6 | 0 | 3.3 |
| CD3B376 | 19.5 | 3.1 | 0.4 | 0.2 | 0 | 0 |

High Concentration Stability

Many monoclonal antibodies are formulated at high concentration (>100 mg/ml) to reduce injection volume to facilitate subcutaneous administration. In addition, all monoclonal antibodies are exposed to transiently high concentrations (≥50 mg/ml) during the purification process. High concentration stability is therefore a critical quality attribute for these molecules. Concentration is performed using centrifugal ultrafiltration devices with 30 kDa MWCO membranes. 5.1 to 5.3 mg of each protein were initially diluted to the same starting concentration and centrifuged at 4000×g in 15-minute intervals. At the end of each 15-minute centrifugation step, the concentrators are removed from the centrifuge and a visual estimate of the remaining sample volume is recorded. Concentration is measured by SoloVPE instrument. Concentrated samples were incubated at 4 C and 40 C for 2 weeks and aliquots were drawn at timed intervals to check for the integrity by analytical SEC. TMCB150 and the parental mAbs (CD3B376 and TMEB762) concentrated normally. Final concentration of TMCB150 was 99.4 mg/mL and that of the parental mAbs were 52.2 mg/mL (TMEB762) and 52.6 mg/mL (CD3B376). Concentration remained the same for 2 weeks at 4 C and 40 C suggesting that molecules have good intrinsic properties with no potential for aggregation or adsorption to the eppendorf tubes. % species (A: Aggregate; M: Monomer; F: Fragment) as measured from SEC peak integration is provided below in the table. At high concentration, molecules are intact with 4-5% aggregates and ≤0.3% fragments after storing for 2 weeks at 40 C predicting good shelf life.

TABLE 21

|  | Time Zero | | | 2 weeks, 4° C. | | | 2 weeks, 40° C. | | |
| --- | --- | --- | --- | --- | --- | --- | --- | --- | --- |
|  | A | M | F | A | M | F | A | M | F |
| TMCB150 | 0.8 | 99.2 | 0 | 1.4 | 98.6 | 0 | 3.6 | 96.1 | 0.3 |
| TMEB762 | 2.5 | 97.5 | 0 | 2.7 | 97.3 | 0 | 3.1 | 96.9 | 0 |
| CD3B376 | 1.1 | 98.9 | 0 | 2.5 | 97.5 | 0 | 5.1 | 94.7 | 0.2 |

Affinity Determination of Anti-TMEFF2/CD3 Bispecific Antibody by Kinetic Exclusion Assay (KinExA)

A KinExA 3200 instrument (Sapidyne Instruments, Inc.) was used to measure solution equilibrium affinity, $K_D$, of the bispecifc mAb TMCB150 and its bivalent TMEFF2 parent TMEB762 mAb to human TMEFF2 extracellular domain (ECD). Serial dilutions of human TMEFF2 extracellular domain (ECD) were prepared with a constant concentration of anti-TMEFF2 mAb in 10 mM HEPES, 150 mM NaCL, 0.05% surfactant P20, pH 7.4, 0.1% BSA, and 0.02% NaN3. The reaction mixtures were incubated at RT until the binding interactions reached equilibrium. The duration of the incubation was determined using KinExA software simulation. Beads were prepared by direct covalent immobilization of TMEFF2-ECD by amine-coupling on pre-activated beads composed of bis-acrylamide/azlactone copolymer (Pierce Biotechnology, Inc.). After incubation the samples were run on the KinExA instrument to assess free antibody in the mixture by passing the mixture though the TMEFF2-modified beads, and detecting the captured antibody using a fluorescently labeled secondary antibody. The data was fit with a 1:1 binding model using the KinExA Pro software.

TABLE 22

| mAb sample | $K_D$ pM | 95% CI, $K_D$ pM |
| --- | --- | --- |
| TMCB150 | 63.6 | 55.8-71.9 |
| TMEB762 | 46.1 | 38.0-55.1 |

Measurement of Binding Affinity of Anti-TMEFF2/CD3 Bispecific Antibody to N-Terminal CD3s Peptide Kinetic rate constants were measured by SPR performed using Biacore 8K (GE Healthcare) and anti-human Fc biosensor surfaces. Anti-human immunoglobulin antibodies were covalently coupled to the surface of a CM4 sensor chip (GE Healthcare). Antibodies of interest were captured on the anti-human immunoglobulin sensor chip, followed by injection of N-terminal CD3s peptide at various concentrations in HEPES Buffered Saline containing 0.05% surfactant P20 (Tween™ 20) and 100 ug/mL BSA. The surface was regenerated with 2 pulses injections of 30 μL of 0.8% phosphoric acid at 100 μL/min. Data reported is the difference in SPR signal between the flow cell containing the captured antibody and a reference cell without captured antibody. Additional instrumental contributions to the signal were removed by subtraction of the data from the blank injection from the reference-subtracted signal. The data were analyzed by fitting association and dissociation phases at all concentrations (global fit) with a 1:1 binding model using the Biaevaluation software (Biacore, Inc.). Data is reported as average+95% CI (Confidence Interval) which is calculated by t value for 95% CI*stdev/square root of the number of replicates.

TABLE 23

| mAb sample | Average $k_{on}$ (1/Ms) | Average $k_{off}$ (1/s) | Average $K_D$, nM | 95% CI, $K_D$ pM |
|---|---|---|---|---|
| TMCB150 | 3.57E+04 | 1.03E−03 | 28.7 | 24.4-34.3 |
| CD3B376 | 4.33E+04 | 1.17E−03 | 26.9 | 21.1-34.4 |

Example 9. Bispecific TMEFF2×CD3 Antibodies are Effective in T-Cell Mediated Killing of Prostate Cancer Cells T Cell-Mediated Killing of Prostate Cancer Cells In Vitro.

Select bispecific TMEFF2×CD3 antibodies were assessed for their ability to mediate T-cell mediated killing of prostate cancer cells.

T-cell mediated killing of the TMEFF2×CD3 bispecific antibodies was measured using a caspase cytotoxicity assay that indirectly measures cell killing via cleavage of a fluorescent substrate by active caspase 3/7. Cleavage of the substrate results in a fluorescent DNA dye, with fluorescence restricted to the cell nucleus. Repeated fluorescence measurements are taken in each well throughout the course of the assay, using a motorized 10× objective, capable of precisely imaging well(s) at the same coordinates. Target cell populations are identified based on defined size restrictions and/or through the use of a secondary label.

Frozen Pan CD3$^+$ T-cells (Biological Specialty Corporation, Colmar, Pa.) were isolated by negative selection from normal healthy donors. Prostate cancer cells expressing TMEFF2 (LNCaP-AR) were cultured in RPMI 1640 with 10% HI FBS+ supplements (Life Technologies). T-cells and target cells were combined at an effector to target ratio (E:T) of 3:1 in Phenol Red free RPMI+10% FBS and supplements (Life Technologies), without selection reagents, and 0.6 uL of NucView caspase reagent (Essen Bioscience) was added to each mL of cells, per manufacturer guidelines. A total volume of 0.1 mL cells were added to appropriate wells of a clear, 96-well flat-bottom plate (BD Falcon). TMEFF2× CD3 bispecific antibodies were prepared at 2× final concentration in Phenol Red free RPMI, prepared as indicated above, and 0.1 mL of compounds were added to each well. After 30 minute incubation at room temperature to minimize cell aggregation at the edge of wells, plates were transferred to the Zoom Incucyte instrument (Essen Bioscience) held at 37° C., 5% CO$_2$.

Processing definitions on the Incucyte were designed for each cell line tested, per manufacture guidelines. Measurements were taken every six hours, until a plateau in the caspase signal was observed, and followed by three or more successive decreases from the maximum signal in the well(s) containing the highest concentration of the test compound(s).

After the assay was complete, each plate was analyzed using the appropriate processing definition. Raw fluorescent data was exported from the Incucyte Zoom software, and pasted into GraphPad Prism (GraphPad Software, Inc., La Jolla, Calif.). Caspase 3/7 activity was determined by calculating the area under the curve (AUC) for each well in GraphPad. AUC values were plotted as a function of Log 10 nM compound. The EC50 for each dose curve, in nanomolar (nM), was reported following non-linear regression analysis (4 parameter fit, least ordinary squares). Each assay contained a minimum of three biologic replicates, and each cell line was tested using T-cells from five healthy donors. Data were further analyzed by non-clinical statistics using a non-linear regression model.

FIG. 3 shows killing of LNCaP cells over time as measured by increased caspase 3/7 activity of select bispecific TMEFF2×CD3 antibodies.

Bispecific TMEFF2×CD3 Antibodies are Effective in In Vivo Prostate Cancer Tumor Models Select bispecific antibodies were tested in ex vivo LnCaP prostate cancer model in male NSG mice. For the study, 10$^6$ LnCaP cells in 50% Cultrex in 0.2 mL/animal were administered by subcutaneous injection into right flank on Day 0. The animals were randomized when tumors reached a volume of about ~100-150 mm$^3$ and injected 20$^6$ T-cells intraperitoneally/mouse at day 15. Ten animals were in each group. Treatment with the antibodies began 1-3 days post T-cell injections. Antibodies were administered intraperitoneally twice a week. Prior to dosing, all animals received IVIG+Fc Block. Tumor volume and body weight was assessed twice a week until tumors reached ~1200 mm$^3$. Treatment groups are shown in Table 24. CD3×Null antibody was used as a negative control in these assays, having CD3B219 CD3 binding arm and a null arm binding HIV gp120.

TABLE 24

| Group | Treatment | Dose |
|---|---|---|
| 1 | CD3 × Null | 5 mg/kg |
| 2 | TMCB93 (TMEB675 × CD3B219) | 5 mg/kg |
| 3 | TMCB93 (TMEB675 × CD3B219) | 0.5 mg/kg |
| 4 | TMCB101 (TMEB570 × CD3B219) | 5 mg/kg |
| 5 | TMCB101 (TMEB570 × CD3B219) | 0.5 mg/kg |
| 6 | TMCB131 (TMEB570 × CD3B376) | 5 mg/kg |
| 7 | TMCB131 (TMEB570 × CD3B376) | 0.5 mg/kg |
| 8 | TMCB132 (TMEB675 × CD3B376) | 5 mg/kg |
| 9 | TMCB132 (TMEB675 × CD3B376) | 0.5 mg/kg |

Figure 4:
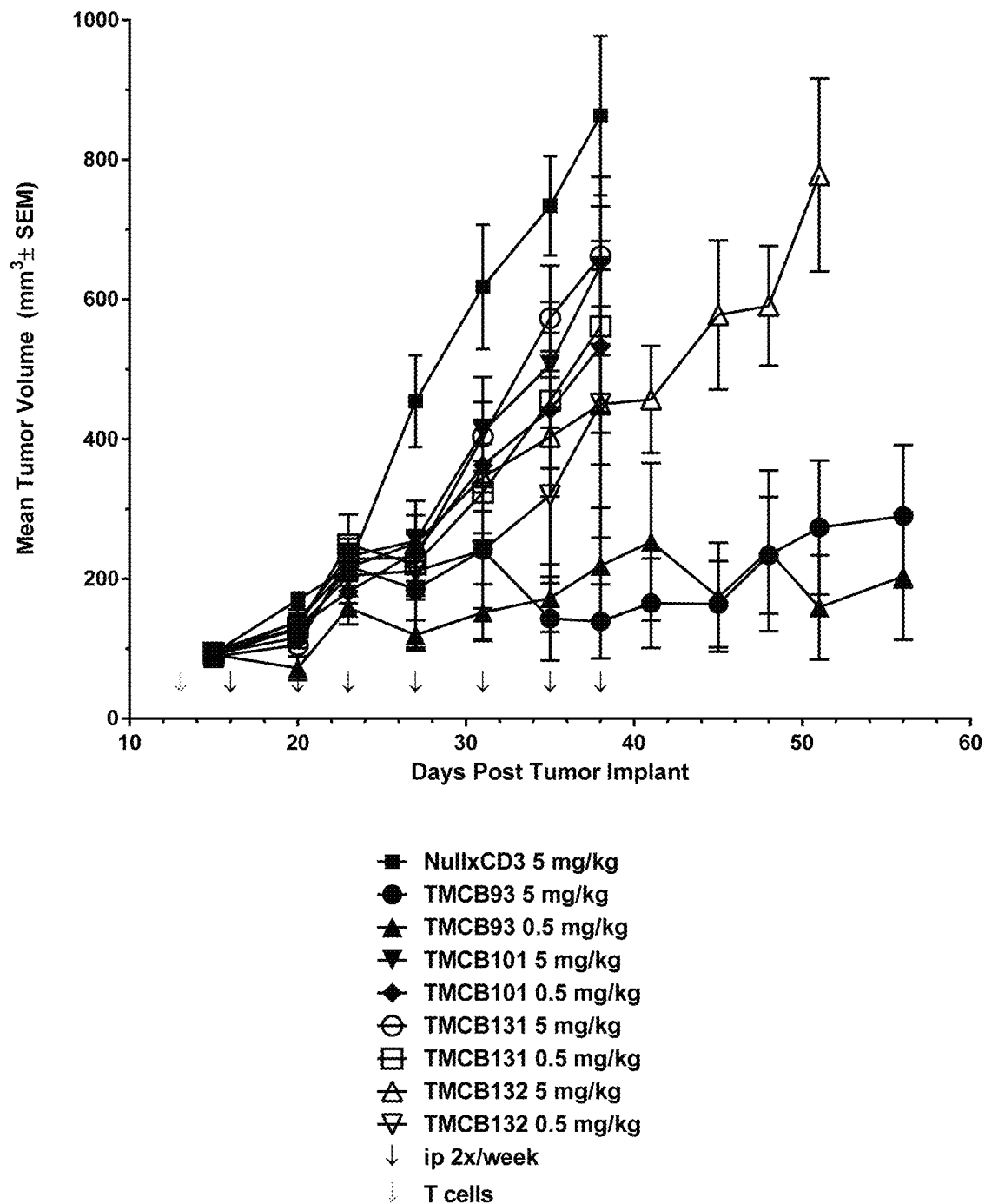
FIG. 4 shows the reduction in mean tumor volume over time post tumor implant by select bispecific anti-TMEFF2/anti-CD3 antibodies in an ex vivo LnCaP prostate cancer model in male NGS mice.
Figure 5A:
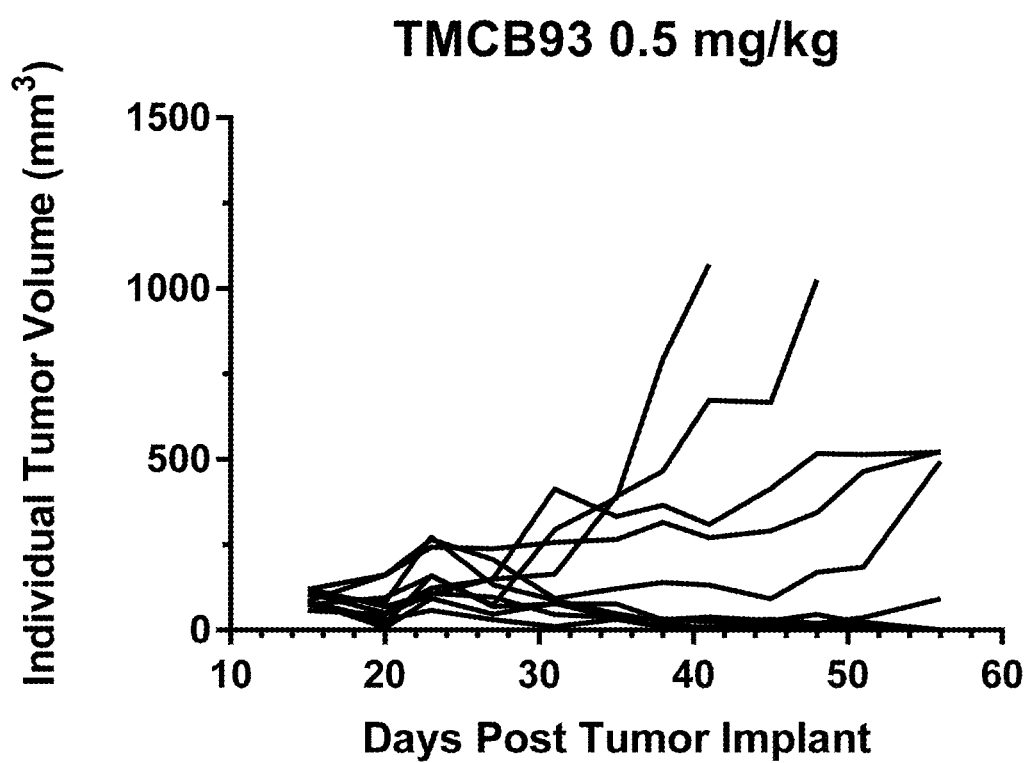
FIG. 5A shows the reduction in mean tumor volume of each mouse treated with 0.5 mg/kg TMCB93 in an ex vivo LnCaP prostate cancer model in male NGS mice.
Figure 5B:
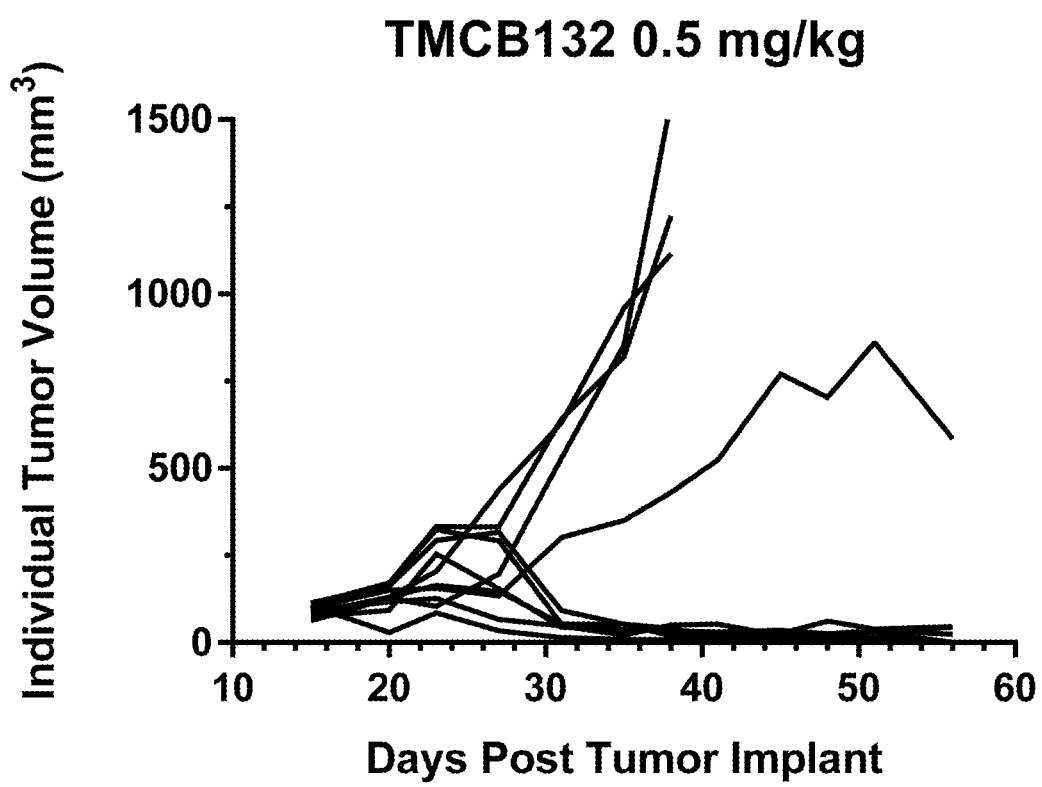
FIG. 5B shows the reduction in mean tumor volume of each mouse treated with 0.5 mg/kg TMCB132 in an ex vivo LnCaP prostate cancer model in male NGS mice.

Table 25 shows the percent tumor growth inhibition on day 38 per each group post tumor implant. FIG. 4 shows the reduction in mean tumor volume over time post tumor implant. FIG. 5A shows the reduction in mean tumor volume of each mouse treated with 0.5 mg/kg TMCB93. FIG. 5B shows the reduction in mean tumor volume of each mouse treated with 0.5 mg/kg TMCB132.

TABLE 25

| Treatment | % TGI on day 38 |
|---|---|
| CNTO7008 (Null × CD3) | |
| TMCB93 (TMEB675 × CD3B219) 5 mg/kg | 83.9 |
| TMCB93 (TMEB675 × CD3B219) 0.5 mg/kg | 75.6 |
| TMCB132 (TMEB675 × CD3B376) 5 mg/kg | 48 |
| TMCB132 (TMEB675 × CD3B376) 0.5 mg/kg | 47.7 |
| TMCB101 (TMEB570 × CD3B219) 5 mg/kg | 25 |
| TMCB101 (TMEB570 × CD3B219) 0.5 mg/kg | 38.3 |
| TMCB131 (TMEB570 × CD3B376) 5 mg/kg | 23.3 |
| TMCB131 (TMEB570 × CD3B376) 0.5 mg/kg | 35 |

Figure 6:
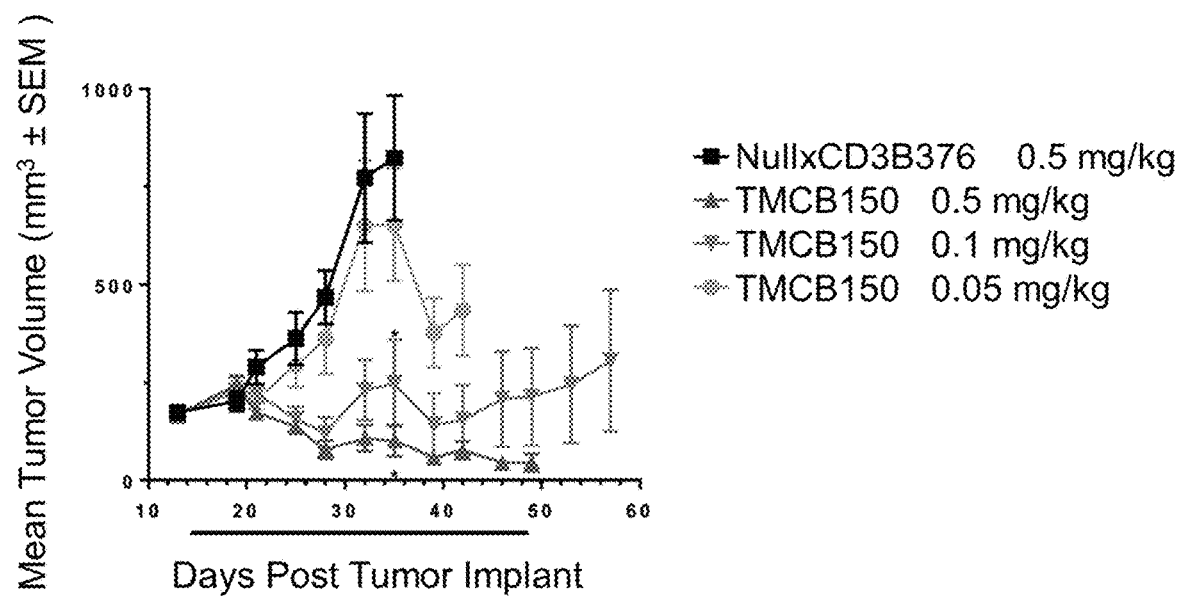
FIG. 6 shows efficacy of TMEB762×CD3B376 in established LNCaP Xenografts in T Cell Humanized NSG Mice.

Efficacy of TMEB762×CD3B376 (TMCB150) was also evaluated in established LNCaP xenografts in male NOD.Cg-Prkdc$^{scid}$ Il2rg$^{tm1Wjl}$/SzJ (NSG) mice humanized with 20e6 T cells. Animals were randomized into groups of 10 animals each by mean tumor volume on day 13 post tumor implantation. TMEB762×CD3B376 at 0.5, 0.1 and 0.05 mg/kg or null×CD3B376 antibody control at 0.5 mg/kg were dosed IP twice weekly for 5 weeks. On day 35 post-tumor implantation, when at least eight animals remained per group, tumor growth inhibition (% TGI) as determined by tumor volume was calculated. Statistically significant tumor growth inhibition was observed with TMEB762×CD3B376 at 0.5 and 0.1 mg/kg, but not at 0.05 mg/kg, as compared to null×CD3 control (FIG. 6). TMEB762×CDB376 at 0.5, 0.1, and 0.05 mg/kg elicited tumor growth inhibition of 110%, 88% and 25%, respectively, as compared to null×CD3 treated controls. TMEB762×CDB376 treatment resulted in seven and three complete responses at 0.5 and 0.1 mg/kg, respectively. Subcutaneous LNCaP tumors were measured by caliper twice weekly and the results presented as mean tumor volume (mm$^3$)±SEM (≥8 mice remaining per group).

T Cell Activation in Response to Administration of TMCB132

Figure 7:
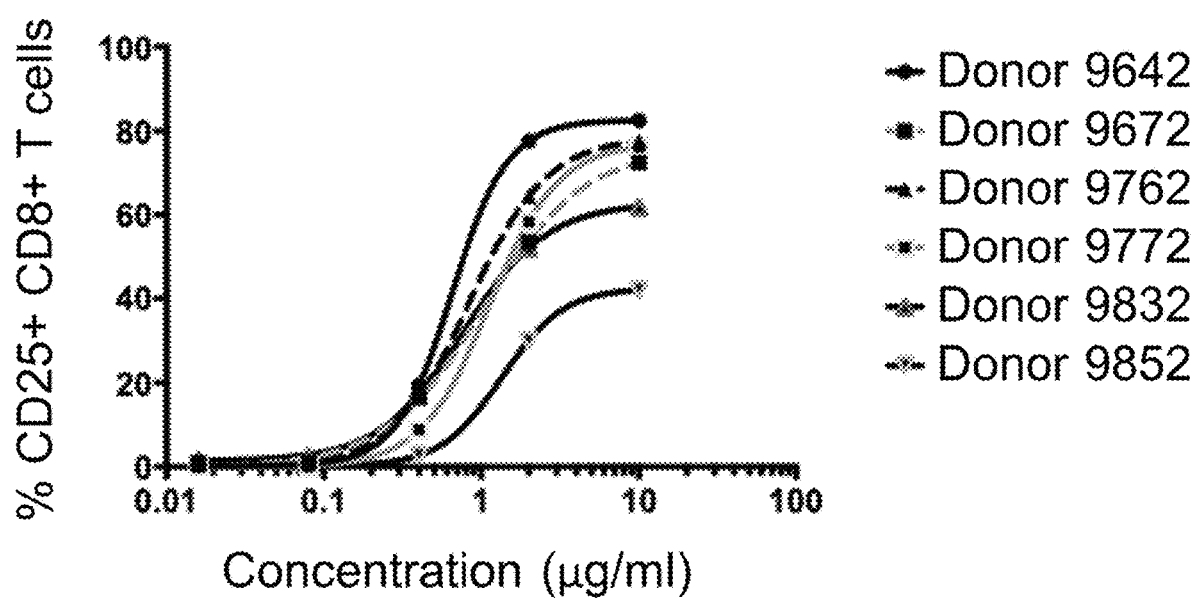
FIG. 7 shows T-cell activation in LnCaP prostatec cancer cells in response to administration of TMCB132.

T cell activation in LnCaP prostate cancer cells was measured by flow cytometry, specifically by assessing CD25 positivity of CD3+/CD8+ T cells in 6 separate normal healthy donors (9642, 9672, 9762, 9772, 9832, 9852) 72 hours after treatment with TMCB132 (FIG. 7). Activation of CD3+ pan-T cells added at a 3:1 effector:target ratio was observed in response to administration of TMCB132 on LnCaP prostate cancer cells.

T-Cell Mediated Cytotoxicity of TMCB132 In Vitro.

Figure 8:
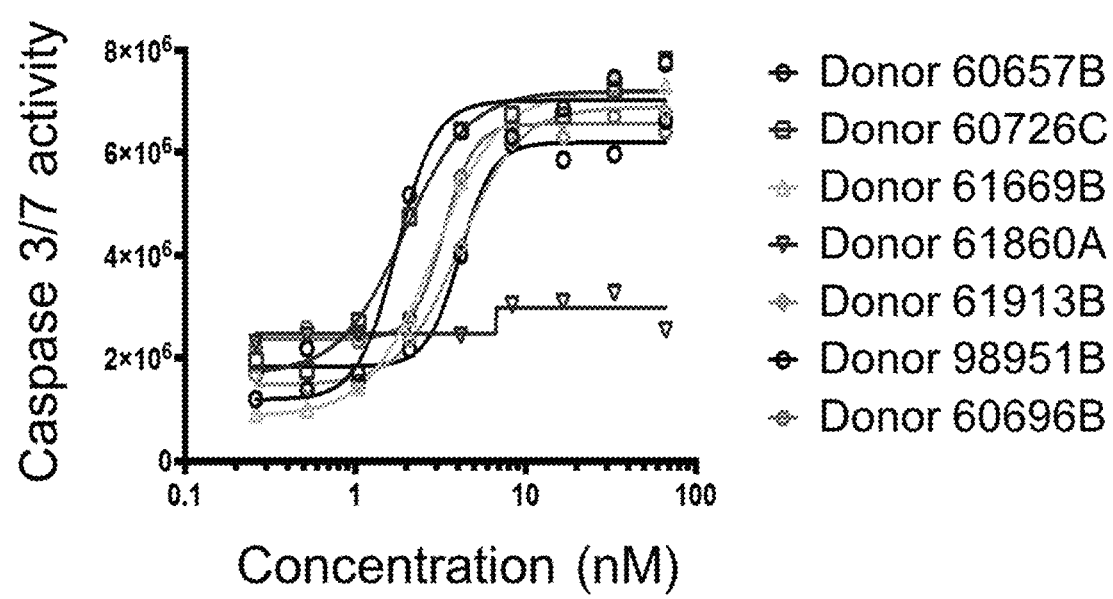
FIG. 8 shows T cell-mediated cytotoxicity of TMCB132.

T-cell-mediated cytotoxicity assay was used to evaluate the cytotoxicity potential of TMCB132 in vitro, using live-time lapse imaging on the Incucyte platform. TMCB132 was tested in TMEFF2 positive cell line LnCaP, in presence of isolated pan human CD3+ T cells from healthy donors at a (Effector:Target) effector:target ratio (E:T ratio) of 3:1. Cell death by apoptosis was monitored by measuring the fluorescence signal for active caspase-3/7 over a time period of 96 hours. TMCB132 promoted a dose-dependent reduction of viable LnCaP cells with increasing time. Dose-dependent increase in caspase-3/7 activity or fluorescence signal indicated cell death in LnCaP cells in presence of the T cells (FIG. 8). The data suggests that TMCB132 is effective in inducing T cell-mediated death in the LnCaP tumor cells.

Efficacy of TMCB132 in Established SC Human Prostate Xenograph in T-Cell Humanized Mice.

Figure 9:
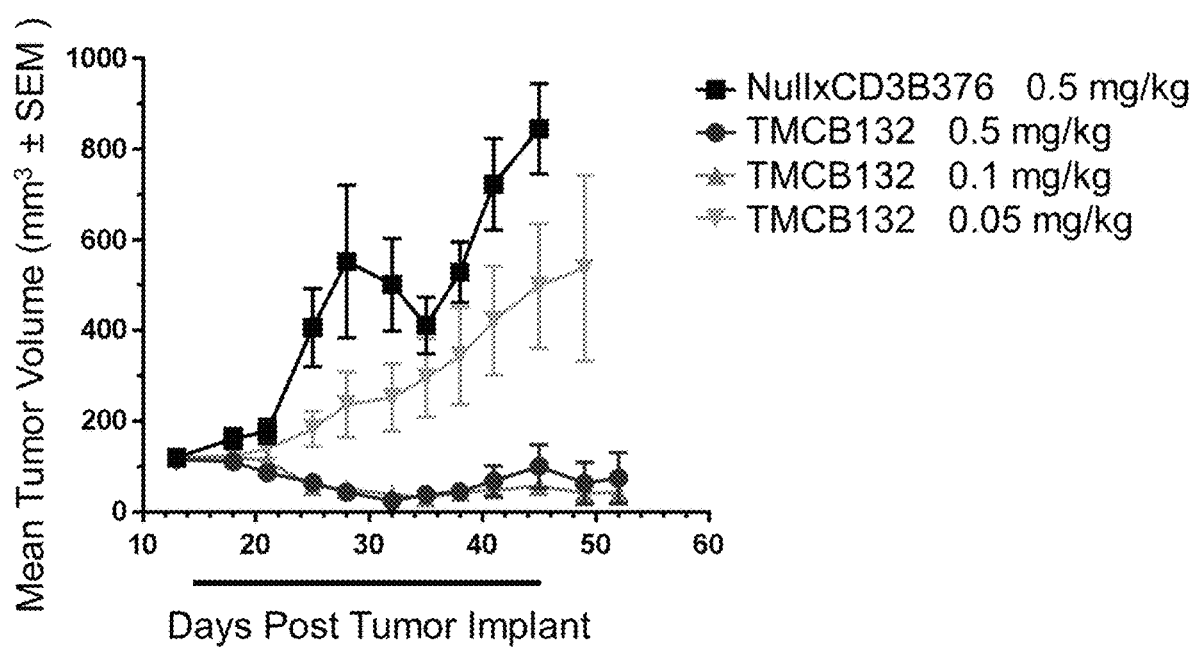
FIG. 9 shows the antitumor efficacity of TMCB132 in T-cell humanized mice.

The antitumor efficacy of TMCB132 was evaluated in established subcutaneous (SC) human prostate LNCaP xenografts in male NOD.Cg-Prkdc$^{scid}$ Il2rg$^{tm1Wjl}$/SzJ (NSG, The Jackson Laboratory, Bar Harbor, Me.) mice humanized with 20e$^6$ T cells. NSG male. Animals were randomized into groups of 10 animals each by mean tumor volume on day 13 post tumor implantation. TMCB132 at 0.5, 0.1 and 0.05 mg/kg or null×CD3B219 antibody control at 0.5 mg/kg were dosed IP twice weekly for 4 weeks. On day 45 post-tumor implantation, when at least seven animals remained per group, tumor growth inhibition (% TGI) as determined by tumor volume was calculated. Statistically significant tumor growth inhibition was observed with TMCB132 at 0.5 and 0.1 mg/kg and 0.05 mg/kg, as compared to null×CD3 control (FIG. 9, p≤0.0001). TMCB132 at 0.5, 0.1, and 0.05 mg/kg elicited tumor growth inhibition of 102%, 109% and 47%, respectively, as compared to null×CD3 treated controls. TMCB132 treatment resulted in three, two and one complete responses at 0.5, 0.1 and 0.05 mg/kg, respectively.

What is claimed:

1. An isolated bispecific anti-TMEFF2/anti-CD3 antibody or an antigen binding fragment thereof comprising a first domain that binds TMEFF2 and a second domain that binds CD3, wherein the antibody binds to the membrane proximal region of SEQ ID NO: 110 of TMEFF2 and wherein
the first domain comprises a HCDR1, a HCDR2, a HCDR3, a LCDR1, a LCDR2, and a LCDR3 of SEQ ID NOs: 10, 12, 15, 18, 20, and 86, respectively; and
the second domain comprises a HCDR1, a HCDR2, a HCDR3, a LCDR1, a LCDR2, and a LCDR3 of SEQ ID NOs: 68, 69, 70, 71, 72, and 73, respectively.

2. The isolated bispecific anti-TMEFF2/anti-CD3 antibody or the antigen binding fragment thereof of claim 1, wherein the antibody binds within residues DAGYTGQHCEKKDYSVL (SEQ ID NO: 58) to the membrane proximal region of TMEFF2.

3. The isolated bispecific anti-TMEFF2/anti-CD3 antibody or the antigen binding fragment thereof of claim 1, wherein the antibody binds to the membrane proximal region of TMEFF2 with a dissociation constant ($K_D$) of about $0.4 \times 10^{-9}$ M or less, wherein the $K_D$ is measured using surface plasmon resonance in acetate buffer at pH 4.5-5.0 at room temperature.

4. The isolated bispecific anti-TMEFF2/anti-CD3 antibody or the antigen binding fragment thereof of claim 3, wherein the antibody binds to the membrane proximal region of human TMEFF2 with the $K_D$ of between about $0.1 \times 10^{-10}$ M and about $0.4 \times 10^{-9}$ M.

5. The isolated bispecific anti-TMEFF2/anti-CD3 antibody or the antigen binding fragment thereof of claim 1, wherein the first domain comprises the VH of SEQ ID NO: 87 and the VL of SEQ ID NO: 88.

6. The isolated bispecific anti-TMEFF2/anti-CD3 antibody or the antigen binding fragment thereof of claim 1, wherein the second domain comprises a VH of SEQ ID NO: 74 and a VL of SEQ ID NO: 75.

7. An isolated bispecific anti-TMEFF2/anti-CD3 antibody or an antigen binding fragment thereof comprising a first domain that binds TMEFF2 and a second domain that binds CD3, wherein
a) the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises a HCDR1, a HCDR2, a HCDR3, a LCDR1, a LCDR2 and a LCDR3 of SEQ ID NOs: 68, 69, 70, 71, 72 and 73, respectively;
b) the first domain comprises a VH of SEQ ID NO: 87 and a VL of SEQ ID NO: 88, and the second domain comprises a VH of SEQ ID NO: 74 and a VL of SEQ ID NO: 75; or
c) the bispecific anti-TMEFF2/anti-CD3 antibody or an antigen binding fragment thereof comprises a HC1 of SEQ ID NO: 91, a LC1 of SEQ ID NO: 92, a HC2 of SEQ ID NO: 78 and a LC2 of SEQ ID NO: 79.

8. The isolated bispecific anti-TMEFF2/anti-CD3 antibody or the antigen binding fragment thereof of claim 1, wherein the antibody is an IgG1, an IgG2, an IgG3 or an IgG4 isotype.

9. The isolated bispecific anti-TMEFF2/anti-CD3 antibody or the antigen binding fragment thereof of claim 1, wherein the antibody comprises alanine at position 234, alanine at position 235 or alanine at position 234 and alanine at position 235 in the HC1, in the HC2, or in the HC1 and the HC2, wherein residue numbering is according to the EU Index.

10. The isolated bispecific anti-TMEFF2/anti-CD3 antibody or the antigen binding fragment thereof of claim 1, wherein the antibody comprises proline at position 228 in the HC1 and in the HC2, wherein residue numbering is according to the EU Index.

11. The isolated bispecific anti-TMEFF2/anti-CD3 antibody or the antigen binding fragment thereof of claim 1, wherein the antibody comprises phenylalanine at position 405 and arginine at position 409 in the HC1 and leucine at position 405 and lysine at position 409 in the HC2, wherein residue numbering is according to the EU Index.

12. A pharmaceutical composition comprising the bispecific anti-TMEFF2/anti-CD3 antibody or the antigen binding fragment thereof of claim 1 and a pharmaceutically acceptable carrier.

13. A polynucleotide
a) encoding the bispecific anti-TMEFF2/anti-CD3 antibody or an antigen binding fragment thereof of claim 1 or
b) comprising a polynucleotide sequence of SEQ ID NOs: 95, 96, 97, and 98.

14. A vector comprising the polynucleotide of claim 13.

15. A host cell comprising the vector of claim 14.

16. A method of producing a bispecific anti-TMEFF2/anti-CD3 antibody or an antigen binding fragment thereof, comprising culturing the host cell of claim 15 in conditions that the antibody is expressed, and recovering and purifying the bispecific anti-TMEFF2/anti-CD3 antibody or the antigen binding fragment thereof produced by the host cell.

17. A method of producing the bispecific anti-TMEFF2/anti-CD3 antibody or the antigen binding fragment thereof of claim 1, comprising:
combining a monospecific bivalent TMEFF2 antibody having two identical HC1 and two identical LC1 and a monospecific bivalent CD3 antibody having two identical HC2 and two identical LC2 in a mixture of about 1:1 molar ratio;
introducing a reducing agent into the mixture;
incubating the mixture comprising the reducing agent for about ninety minutes to about six hours;
removing the reducing agent after said incubating step; and
purifying the bispecific anti-TMEFF2/anti-CD3 antibody or an antigen binding fragment thereof that comprises the HC1, the LC1, the HC2 and the LC2 after the reducing agent has been removed,
wherein the HC1 and LC1 comprises a HCDR1, a HCDR2, a HCDR3, a LCDR1, a LCDR2, and a LCDR3 of SEQ ID NOs: 10, 12, 15, 18, 20, and 86, respectively, and the HC2 and LC2 comprises a HCDR1, a HCDR2, a HCDR3, a LCDR1, a LCDR2, and a LCDR3 of SEQ ID NOs: 68, 69, 70, 71, 72, and 73, respectively.

18. The method of claim 17, wherein the reducing agent is 2-mercaptoethanolamine (2-MEA).

19. The method of claim 18, wherein the 2-MEA is present at a concentration of about 25 mM to about 75 mM.

20. The method of claim 19, wherein the incubating step is performed at a temperature of about 25° C. to about 37° C.

21. The isolated bispecific anti-TMEFF2/anti-CD3 antibody or an antigen binding fragment thereof of claim 7 comprising a first domain that binds TMEFF2 and a second domain that binds CD3, wherein the first domain comprises a HCDR1, a HCDR2, a HCDR3, a LCDR1, a LCDR2 and a LCDR3 of SEQ ID NOs: 10, 12, 15, 18, 20 and 86, respectively, and the second domain comprises a HCDR1, a HCDR2, a HCDR3, a LCDR1, a LCDR2 and a LCDR3 of SEQ ID NOs: 68, 69, 70, 71, 72 and 73, respectively.

22. The isolated bispecific anti-TMEFF2/anti-CD3 antibody or an antigen binding fragment thereof of claim 7 comprising a first domain that binds TMEFF2 and a second domain that binds CD3, wherein the first domain comprises a VH of SEQ ID NO: 87 and a VL of SEQ ID NO: 88, and the second domain comprises a VH of SEQ ID NO: 74 and a VL of SEQ ID NO: 75.

23. The isolated bispecific anti-TMEFF2/anti-CD3 antibody or an antigen binding fragment thereof of claim 7 comprising a first domain that binds TMEFF2 and a second domain that binds CD3, wherein the first domain comprises a HC1 of SEQ ID NO: 91 and a LC1 of SEQ ID NO: 92, and the second domain comprises a HC2 of SEQ ID NO: 78 and a LC2 of SEQ ID NO: 79.

* * * * *

SEQUENCE LISTING

```
<160> NUMBER OF SEQ ID NOS: 112

<210> SEQ ID NO 1
<211> LENGTH: 374
<212> TYPE: PRT
<213> ORGANISM: Homo sapiens

<400> SEQUENCE: 1

Met Val Leu Trp Glu Ser Pro Arg Gln Cys Ser Ser Trp Thr Leu Cys
1               5                   10                  15

Glu Gly Phe Cys Trp Leu Leu Leu Pro Val Met Leu Leu Ile Val
            20                  25                  30

Ala Arg Pro Val Lys Leu Ala Ala Phe Pro Thr Ser Leu Ser Asp Cys
        35                  40                  45

Gln Thr Pro Thr Gly Trp Asn Cys Ser Gly Tyr Asp Asp Arg Glu Asn
    50                  55                  60

Asp Leu Phe Leu Cys Asp Thr Asn Thr Cys Lys Phe Asp Gly Glu Cys
65                  70                  75                  80

Leu Arg Ile Gly Asp Thr Val Thr Cys Val Cys Gln Phe Lys Cys Asn
                85                  90                  95

Asn Asp Tyr Val Pro Val Cys Gly Ser Asn Gly Glu Ser Tyr Gln Asn
            100                 105                 110

Glu Cys Tyr Leu Arg Gln Ala Ala Cys Lys Gln Gln Ser Glu Ile Leu
        115                 120                 125

Val Val Ser Glu Gly Ser Cys Ala Thr Asp Ala Gly Ser Gly Ser Gly
    130                 135                 140

Asp Gly Val His Glu Gly Ser Gly Glu Thr Ser Gln Lys Glu Thr Ser
145                 150                 155                 160

Thr Cys Asp Ile Cys Gln Phe Gly Ala Glu Cys Asp Glu Asp Ala Glu
                165                 170                 175
```

```
Asp Val Trp Cys Val Cys Asn Ile Asp Cys Ser Gln Thr Asn Phe Asn
            180                 185                 190

Pro Leu Cys Ala Ser Asp Gly Lys Ser Tyr Asp Asn Ala Cys Gln Ile
        195                 200                 205

Lys Glu Ala Ser Cys Gln Lys Gln Glu Lys Ile Glu Val Met Ser Leu
    210                 215                 220

Gly Arg Cys Gln Asp Asn Thr Thr Thr Thr Lys Ser Glu Asp Gly
225                 230                 235                 240

His Tyr Ala Arg Thr Asp Tyr Ala Glu Asn Ala Asn Lys Leu Glu Glu
                245                 250                 255

Ser Ala Arg Glu His His Ile Pro Cys Pro Glu His Tyr Asn Gly Phe
            260                 265                 270

Cys Met His Gly Lys Cys Glu His Ser Ile Asn Met Gln Glu Pro Ser
        275                 280                 285

Cys Arg Cys Asp Ala Gly Tyr Thr Gly Gln His Cys Glu Lys Lys Asp
    290                 295                 300

Tyr Ser Val Leu Tyr Val Pro Gly Pro Val Arg Phe Gln Tyr Val
305                 310                 315                 320

Leu Ile Ala Ala Val Ile Gly Thr Ile Gln Ile Ala Val Ile Cys Val
                325                 330                 335

Val Val Leu Cys Ile Thr Arg Lys Cys Pro Arg Ser Asn Arg Ile His
            340                 345                 350

Arg Gln Lys Gln Asn Thr Gly His Tyr Ser Ser Asp Asn Thr Thr Arg
        355                 360                 365

Ala Ser Thr Arg Leu Ile
        370

<210> SEQ ID NO 2
<211> LENGTH: 334
<212> TYPE: PRT
<213> ORGANISM: Homo sapiens

<400> SEQUENCE: 2

Phe Pro Thr Ser Leu Ser Asp Cys Gln Thr Pro Thr Gly Trp Asn Cys
1               5                   10                  15

Ser Gly Tyr Asp Asp Arg Glu Asn Asp Leu Phe Leu Cys Asp Thr Asn
                20                  25                  30

Thr Cys Lys Phe Asp Gly Glu Cys Leu Arg Ile Gly Asp Thr Val Thr
            35                  40                  45

Cys Val Cys Gln Phe Lys Cys Asn Asn Asp Tyr Val Pro Val Cys Gly
        50                  55                  60

Ser Asn Gly Glu Ser Tyr Gln Asn Glu Cys Tyr Leu Arg Gln Ala Ala
65                  70                  75                  80

Cys Lys Gln Gln Ser Glu Ile Leu Val Val Ser Glu Gly Ser Cys Ala
                85                  90                  95

Thr Asp Ala Gly Ser Gly Ser Gly Asp Gly Val His Glu Gly Ser Gly
            100                 105                 110

Glu Thr Ser Gln Lys Glu Thr Ser Thr Cys Asp Ile Cys Gln Phe Gly
        115                 120                 125

Ala Glu Cys Asp Glu Asp Ala Glu Asp Val Trp Cys Val Cys Asn Ile
    130                 135                 140

Asp Cys Ser Gln Thr Asn Phe Asn Pro Leu Cys Ala Ser Asp Gly Lys
145                 150                 155                 160

Ser Tyr Asp Asn Ala Cys Gln Ile Lys Glu Ala Ser Cys Gln Lys Gln
```

```
                165                 170                 175
Glu Lys Ile Glu Val Met Ser Leu Gly Arg Cys Gln Asp Asn Thr Thr
            180                 185                 190

Thr Thr Thr Lys Ser Glu Asp Gly His Tyr Ala Arg Thr Asp Tyr Ala
        195                 200                 205

Glu Asn Ala Asn Lys Leu Glu Glu Ser Ala Arg Glu His His Ile Pro
    210                 215                 220

Cys Pro Glu His Tyr Asn Gly Phe Cys Met His Gly Lys Cys Glu His
225                 230                 235                 240

Ser Ile Asn Met Gln Glu Pro Ser Cys Arg Cys Asp Ala Gly Tyr Thr
            245                 250                 255

Gly Gln His Cys Glu Lys Lys Asp Tyr Ser Val Leu Tyr Val Val Pro
        260                 265                 270

Gly Pro Val Arg Phe Gln Tyr Val Leu Ile Ala Ala Val Ile Gly Thr
    275                 280                 285

Ile Gln Ile Ala Val Ile Cys Val Val Leu Cys Ile Thr Arg Lys
290                 295                 300

Cys Pro Arg Ser Asn Arg Ile His Arg Gln Lys Gln Asn Thr Gly His
305                 310                 315                 320

Tyr Ser Ser Asp Asn Thr Thr Arg Ala Ser Thr Arg Leu Ile
            325                 330
```

<210> SEQ ID NO 3
<211> LENGTH: 41
<212> TYPE: PRT
<213> ORGANISM: Homo sapiens

<400> SEQUENCE: 3

```
His His Ile Pro Cys Pro Glu His Tyr Asn Gly Phe Cys Met His Gly
1               5                   10                  15

Lys Cys Glu His Ser Ile Asn Met Gln Glu Pro Ser Cys Arg Cys Asp
            20                  25                  30

Ala Gly Tyr Thr Gly Gln His Cys Glu
        35                  40
```

<210> SEQ ID NO 4
<211> LENGTH: 207
<212> TYPE: PRT
<213> ORGANISM: Homo sapiens

<400> SEQUENCE: 4

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
            85                  90                  95

Val Cys Tyr Pro Arg Gly Ser Lys Pro Glu Asp Ala Asn Phe Tyr Leu
        100                 105                 110

Tyr Leu Arg Ala Arg Val Cys Glu Asn Cys Met Glu Met Asp Val Met
```

```
                115                 120                 125
Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Arg Gln Arg Gly Gln Asn
                165                 170                 175

Lys Glu Arg Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
        195                 200                 205

<210> SEQ ID NO 5
<211> LENGTH: 104
<212> TYPE: PRT
<213> ORGANISM: Homo sapiens

<400> SEQUENCE: 5

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
                100

<210> SEQ ID NO 6
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Phe Pro Thr Ser Leu Ser Asp Cys Gln Thr Pro Thr Gly Trp Asn Cys
1               5                   10                  15

Ser Gly Tyr Asp Asp Arg Glu Asn Asp Leu Phe Leu Cys Asp Thr Asn
            20                  25                  30

Thr Cys Lys Phe Asp Gly Glu Cys Leu Arg Ile Gly Asp Thr Val Thr
        35                  40                  45

Cys Val Cys Gln Phe Lys Cys Asn Asn Asp Tyr Val Pro Val Cys Gly
    50                  55                  60

Ser Asn Gly Glu Ser Tyr Gln Asn Glu Cys Tyr Leu Arg Gln Ala Ala
65                  70                  75                  80

Cys Lys Gln Gln Ser Glu Ile Leu Val Val Ser Glu Gly Ser Cys Ala
                85                  90                  95

Thr Asp Ala Gly Ser Gly Ser Gly Asp Gly Val His Glu Gly Ser Gly
                100                 105                 110

Glu Thr Ser Gln Lys Glu Thr Ser Thr Cys Asp Ile Cys Gln Phe Gly
```

```
            115                 120                 125
Ala Glu Cys Asp Glu Asp Ala Glu Asp Val Trp Cys Val Cys Asn Ile
130                 135                 140

Asp Cys Ser Gln Thr Asn Phe Asn Pro Leu Cys Ala Ser Asp Gly Lys
145                 150                 155                 160

Ser Tyr Asp Asn Ala Cys Gln Ile Lys Glu Ala Ser Cys Gln Lys Gln
                165                 170                 175

Glu Lys Ile Glu Val Met Ser Leu Gly Arg Cys Gln Asp Asn Thr Thr
            180                 185                 190

Thr Thr Thr Lys Ser Glu Asp Gly His Tyr Ala Arg Thr Asp Tyr Ala
            195                 200                 205

Glu Asn Ala Asn Lys Leu Glu Glu Ser Ala Arg Glu His His Ile Pro
210                 215                 220

Cys Pro Glu His Tyr Asn Gly Phe Cys Met His Gly Lys Cys Glu His
225                 230                 235                 240

Ser Ile Asn Met Gln Glu Pro Ser Cys Arg Cys Asp Ala Gly Tyr Thr
                245                 250                 255

Gly Gln His Cys Glu Lys Lys Asp Tyr Ser Val Leu Tyr Val Val Pro
            260                 265                 270

Gly Pro Val Arg Phe Gln Tyr Val Gly Gly Ser His His His
            275                 280                 285

His His Leu Asn Asp Ile Phe Glu Ala Gln Lys Ile Glu Trp His Glu
290                 295                 300
```

<210> SEQ ID NO 7
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Ser Gly Glu Thr Ser Gln Lys Glu Thr Ser Thr Cys Asp Ile Cys Gln
1               5                   10                  15

Phe Gly Ala Glu Cys Asp Glu Asp Ala Glu Asp Val Trp Cys Val Cys
                20                  25                  30

Asn Ile Asp Cys Ser Gln Thr Asn Phe Asn Pro Leu Cys Ala Ser Asp
            35                  40                  45

Gly Lys Ser Tyr Asp Asn Ala Cys Gln Ile Lys Glu Ala Ser Cys Gln
        50                  55                  60

Lys Gln Glu Lys Ile Glu Val Met Ser Leu Gly Arg Cys Gln Asp Asn
65                  70                  75                  80

Thr Thr Thr Thr Thr Lys Ser Glu Asp Gly His Tyr Ala Arg Thr Asp
                85                  90                  95

Tyr Ala Glu Asn Ala Asn Lys Leu Glu Glu Ser Ala Arg Glu His His
            100                 105                 110

Ile Pro Cys Pro Glu His Tyr Asn Gly Phe Cys Met His Gly Lys Cys
        115                 120                 125

Glu His Ser Ile Asn Met Gln Glu Pro Ser Cys Arg Cys Asp Ala Gly
130                 135                 140

Tyr Thr Gly Gln His Cys Glu Lys Lys Asp Tyr Ser Val Leu Tyr Val
145                 150                 155                 160

Val Pro Gly Pro Val Arg Phe Gln Tyr Val Gly Ser Gly Ser Gly Ser
                165                 170                 175
```

```
Glu Asn Leu Tyr Phe Gln Gly Val Arg Ser Ser Ser Asp Ala His Lys
            180                 185                 190

Ser Glu Val Ala His Arg Phe Lys Asp Leu Gly Glu Glu Asn Phe Lys
        195                 200                 205

Ala Leu Val Leu Ile Ala Phe Ala Gln Tyr Leu Gln Gln Ser Pro Phe
    210                 215                 220

Glu Asp His Val Lys Leu Val Asn Glu Val Thr Glu Phe Ala Lys Thr
225                 230                 235                 240

Cys Val Ala Asp Glu Ser Ala Glu Asn Cys Asp Lys Ser Leu His Thr
                245                 250                 255

Leu Phe Gly Asp Lys Leu Cys Thr Val Ala Thr Leu Arg Glu Thr Tyr
            260                 265                 270

Gly Glu Met Ala Asp Cys Cys Ala Lys Gln Glu Pro Glu Arg Asn Glu
        275                 280                 285

Cys Phe Leu Gln His Lys Asp Asp Asn Pro Asn Leu Pro Arg Leu Val
    290                 295                 300

Arg Pro Glu Val Asp Val Met Cys Thr Ala Phe His Asp Asn Glu Glu
305                 310                 315                 320

Thr Phe Leu Lys Lys Tyr Leu Tyr Glu Ile Ala Arg Arg His Pro Tyr
                325                 330                 335

Phe Tyr Ala Pro Glu Leu Leu Phe Phe Ala Lys Arg Tyr Lys Ala Ala
            340                 345                 350

Phe Thr Glu Cys Cys Gln Ala Ala Asp Lys Ala Ala Cys Leu Leu Pro
        355                 360                 365

Lys Leu Asp Glu Leu Arg Asp Glu Gly Lys Ala Ser Ser Ala Lys Gln
    370                 375                 380

Arg Leu Lys Cys Ala Ser Leu Gln Lys Phe Gly Glu Arg Ala Phe Lys
385                 390                 395                 400

Ala Trp Ala Val Ala Arg Leu Ser Gln Arg Phe Pro Lys Ala Glu Phe
                405                 410                 415

Ala Glu Val Ser Lys Leu Val Thr Asp Leu Thr Lys Val His Thr Glu
            420                 425                 430

Cys Cys His Gly Asp Leu Leu Glu Cys Ala Asp Asp Arg Ala Asp Leu
        435                 440                 445

Ala Lys Tyr Ile Cys Glu Asn Gln Asp Ser Ile Ser Ser Lys Leu Lys
    450                 455                 460

Glu Cys Cys Glu Lys Pro Leu Leu Glu Lys Ser His Cys Ile Ala Glu
465                 470                 475                 480

Val Glu Asn Asp Glu Met Pro Ala Asp Leu Pro Ser Leu Ala Ala Asp
                485                 490                 495

Phe Val Glu Ser Lys Asp Val Cys Lys Asn Tyr Ala Glu Ala Lys Asp
            500                 505                 510

Val Phe Leu Gly Met Phe Leu Tyr Glu Tyr Ala Arg Arg His Pro Asp
        515                 520                 525

Tyr Ser Val Val Leu Leu Leu Arg Leu Ala Lys Thr Tyr Glu Thr Thr
    530                 535                 540

Leu Glu Lys Cys Cys Ala Ala Ala Asp Pro His Glu Cys Tyr Ala Lys
545                 550                 555                 560

Val Phe Asp Glu Phe Lys Pro Leu Val Glu Glu Pro Gln Asn Leu Ile
                565                 570                 575

Lys Gln Asn Cys Glu Leu Phe Glu Gln Leu Gly Glu Tyr Lys Phe Gln
            580                 585                 590

Asn Ala Leu Leu Val Arg Tyr Thr Lys Lys Val Pro Gln Val Ser Thr
```

```
                    595                 600                 605
Pro Thr Leu Val Glu Val Ser Arg Asn Leu Gly Lys Val Gly Ser Lys
610                 615                 620

Cys Cys Lys His Pro Glu Ala Lys Arg Met Pro Cys Ala Glu Asp Tyr
625                 630                 635                 640

Leu Ser Val Val Leu Asn Gln Leu Cys Val Leu His Glu Lys Thr Pro
                645                 650                 655

Val Ser Asp Arg Val Thr Lys Cys Cys Thr Glu Ser Leu Val Asn Arg
                660                 665                 670

Arg Pro Cys Phe Ser Ala Leu Glu Val Asp Glu Thr Tyr Val Pro Lys
                675                 680                 685

Glu Phe Asn Ala Glu Thr Phe Thr Phe His Ala Asp Ile Cys Thr Leu
                690                 695                 700

Ser Glu Lys Glu Arg Gln Ile Lys Lys Gln Thr Ala Leu Val Glu Leu
705                 710                 715                 720

Val Lys His Lys Pro Lys Ala Thr Lys Glu Gln Leu Lys Ala Val Met
                725                 730                 735

Asp Asp Phe Ala Ala Phe Val Glu Lys Cys Cys Lys Ala Asp Asp Lys
                740                 745                 750

Glu Thr Cys Phe Ala Glu Glu Gly Lys Lys Leu Val Ala Ala Ser Gln
                755                 760                 765

Ala Ala Leu Gly Leu Gly Gly Gly Ser His His His His His His Leu
770                 775                 780

Asn Asp Ile Phe Glu Ala Gln Lys Ile Glu Trp His Glu
785                 790                 795

<210> SEQ ID NO 8
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asn Thr Thr Thr Thr Thr Lys Ser Glu Asp Gly His Tyr Ala Arg Thr
1               5                   10                  15

Asp Tyr Ala Glu Asn Ala Asn Lys Leu Glu Glu Ser Ala Arg Glu His
                20                  25                  30

His Ile Pro Cys Pro Glu His Tyr Asn Gly Phe Cys Met His Gly Lys
            35                  40                  45

Cys Glu His Ser Ile Asn Met Gln Glu Pro Ser Cys Arg Cys Asp Ala
        50                  55                  60

Gly Tyr Thr Gly Gln His Cys Glu Lys Lys Asp Tyr Ser Val Leu Tyr
65                  70                  75                  80

Val Val Pro Gly Pro Val Arg Phe Gln Tyr Val Gly Gly Ser His
                85                  90                  95

His His His His
            100

<210> SEQ ID NO 9
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 9

```
Asn Thr Thr Thr Thr Thr Lys Ser Glu Asp Gly His Tyr Ala Arg Thr
1               5                   10                  15
Asp Tyr Ala Glu Asn Ala Asn Lys Leu Glu Glu Ser Ala Arg Glu His
            20                  25                  30
His Ile Pro Cys Pro Glu His Tyr Asn Gly Phe Cys Met His Gly Lys
        35                  40                  45
Cys Glu His Ser Ile Asn Met Gln Glu Pro Ser Cys Arg Cys Asp Ala
    50                  55                  60
Gly Tyr Thr Gly Gln His Cys Glu Lys Lys Asp Tyr Ser Val Leu Tyr
65                  70                  75                  80
Val Val Pro Gly Pro Val Arg Phe Gln Tyr Val Gly Gly Ser Pro
                85                  90                  95
Arg Asn Cys Gly Gly Asp Cys Lys Pro Cys Ile Cys Thr Gly Ser Glu
            100                 105                 110
Val Ser Ser Val Phe Ile Phe Pro Pro Lys Pro Lys Asp Val Leu Thr
        115                 120                 125
Ile Thr Leu Thr Pro Lys Val Thr Cys Val Val Val Asp Ile Ser Gln
130                 135                 140
Asp Asp Pro Glu Val His Phe Ser Trp Phe Val Asp Asp Val Glu Val
145                 150                 155                 160
His Thr Ala Gln Thr Arg Pro Pro Glu Glu Gln Phe Asn Ser Thr Phe
                165                 170                 175
Arg Ser Val Ser Glu Leu Pro Ile Leu His Gln Asp Trp Leu Asn Gly
            180                 185                 190
Arg Thr Phe Arg Cys Lys Val Thr Ser Ala Ala Phe Pro Ser Pro Ile
        195                 200                 205
Glu Lys Thr Ile Ser Lys Pro Glu Gly Arg Thr Gln Val Pro His Val
210                 215                 220
Tyr Thr Met Ser Pro Thr Lys Glu Glu Met Thr Gln Asn Glu Val Ser
225                 230                 235                 240
Ile Thr Cys Met Val Lys Gly Phe Tyr Pro Pro Asp Ile Tyr Val Glu
                245                 250                 255
Trp Gln Met Asn Gly Gln Pro Gln Glu Asn Tyr Lys Asn Thr Pro Pro
            260                 265                 270
Thr Met Asp Thr Asp Gly Ser Tyr Phe Leu Tyr Ser Lys Leu Asn Val
        275                 280                 285
Lys Lys Glu Lys Trp Gln Gln Gly Asn Thr Phe Thr Cys Ser Val Leu
290                 295                 300
His Glu Gly Leu His Asn His His Thr Glu Lys Ser Leu Ser His Ser
305                 310                 315                 320
Pro Gly Lys Gly Gly Gly Ser His His His His His
                325                 330
```

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

```
Ser Tyr Ser Met Ser
1               5
```

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Tyr Tyr Ile Ser
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Ile Ser Gly Ser Gly Gly Phe Thr Asp Tyr Ala Asp Ser Val Lys
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ile Ile Pro Ile Ser Gly Arg Ala Asn Tyr Ala Gln Lys Phe Gln
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ile Ser Gly Gly Gly Ser Phe Thr Ser Tyr Ala Asp Ser Val Lys
1               5                   10                  15

Gly

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Pro Leu Asn Ser Pro His Asp Tyr
1               5

<210> SEQ ID NO 16
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Gly Tyr Ser Ser Gly Arg Ser Thr Thr Tyr Ala Phe Asp Tyr
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Pro Leu Asn Ser Pro His Asp Cys
1               5

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Gln Gly Ile Arg Asn Asp Leu Gly
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ala Ser Gln Ser Val Ser Thr Tyr Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Ser Ser Leu Gln Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ala Ser Tyr Arg Ala Thr
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gln Asp Tyr Asn Tyr Ala Leu Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Tyr Gly His Ser Pro Ile Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Gln Asp Tyr Asn Tyr Ser Leu Thr
1               5

<210> SEQ ID NO 25
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Leu Glu Ser Gly Gly Gly Leu Val Gln Arg Gly Gly
1               5                   10                  15

Ser Leu Arg Pro Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Val Ile Ser Gly Ser Gly Gly Phe Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Arg Met Pro Leu Asn Ser Pro His Asp Tyr Trp Gly Gln Gly Thr
            100                 105                 110

Leu Val Thr Val Ser Ser
        115

<210> SEQ ID NO 26
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Ile Ser Trp Val Arg Gln Ala Pro Gly Gln Gly Leu Glu Trp Met
        35                  40                  45

Gly Gly Ile Ile Pro Ile Ser Gly Arg Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Ser Ser Gly Arg Ser Thr Thr Tyr Ala Phe Asp
            100                 105                 110

Tyr Trp Gly Gln Gly Thr Leu Val Thr Val Ser Ser
        115                 120

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Leu Glu Ser Gly Gly Gly Leu Val Gln Pro Pro Gly
1               5                   10                  15

Gly Ser Leu Arg Leu Ser Cys Ala Ala Ser Gly Phe Thr Phe Ser Ser
            20                  25                  30

Tyr Ser Met Ser Trp Val Arg Gln Ala Pro Lys Gly Leu Glu Trp
        35                  40                  45

Val Ser Val Ile Ser Gly Gly Ser Phe Thr Ser Tyr Ala Asp Ser
    50                  55                  60

Val Lys Gly Arg Phe Thr Ile Ser Arg Asp Asn Ser Asn Asn Thr Leu
65                  70                  75                  80

Tyr Leu Gln Met Ser Ser Leu Arg Ala Glu Asp Thr Ala Phe Tyr Tyr
                85                  90                  95

Cys Ala Arg Met Pro Leu Asn Ser Pro His Asp Cys Trp Gly Gln Gly
            100                 105                 110

Thr Leu Val Thr Val Ser Ser
        115

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Ala Leu
                85                  90                  95

Thr Phe Gly Gly Gly Thr Lys Val Glu Ile Lys
            100                 105

<210> SEQ ID NO 29
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Thr Tyr
            20                  25                  30

Tyr Leu Ala Trp Tyr Gln Gln Lys Pro Gly Gln Ala Pro Arg Leu Leu
        35                  40                  45

Ile Tyr Gly Ala Ser Tyr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly His Ser Pro
                85                  90                  95

Ile Thr Phe Gly Gln Gly Thr Lys Val Glu Ile Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Leu Gln Asp Tyr Asn Tyr Ser Leu
                    85                  90                  95

Thr Phe Gly Gly Gly Thr Lys Val Glu Ile Arg
                100                 105

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Thr Tyr
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Asn Pro
                85                  90                  95

Ile Thr Phe Gly Gln Gly Thr Lys Val Glu Ile Lys
                100                 105

<210> SEQ ID NO 32
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Leu Glu Ser Gly Gly Gly Leu Val Gln Arg Gly Gly
1               5                   10                  15

Ser Leu Arg Pro Ser Cys Ala Ala Ser Gly Phe Thr Phe Ser Ser Tyr
                20                  25                  30

Ser Met Ser Trp Val Arg Gln Ala Pro Gly Lys Gly Leu Glu Trp Val
            35                  40                  45

Ser Val Ile Ser Gly Ser Gly Gly Phe Thr Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Arg Met Pro Leu Asn Ser Pro His Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
```

Ser Gly Ala Leu Thr Ser Gly Val His Thr Phe Pro Ala Val Leu Gln
            165                 170                 175

Ser Ser Gly Leu Tyr Ser Leu Ser Ser Val Thr Val Pro Ser Ser
        180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 33
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Ile Ser Trp Val Arg Gln Ala Pro Gly Gln Gly Leu Glu Trp Met
        35                  40                  45

Gly Gly Ile Ile Pro Ile Ser Gly Arg Ala Asn Tyr Ala Gln Lys Phe
    50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Ser Ser Gly Arg Ser Thr Thr Tyr Ala Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 34
<211> LENGTH: 446
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 34

```
Glu Val Gln Leu Leu Glu Ser Gly Gly Gly Leu Val Gln Pro Pro Gly
1               5                   10                  15

Gly Ser Leu Arg Leu Ser Cys Ala Ala Ser Gly Phe Thr Phe Ser Ser
            20                  25                  30

Tyr Ser Met Ser Trp Val Arg Gln Ala Pro Gly Lys Gly Leu Glu Trp
        35                  40                  45

Val Ser Val Ile Ser Gly Gly Ser Phe Thr Ser Tyr Ala Asp Ser
50                  55                  60

Val Lys Gly Arg Phe Thr Ile Ser Arg Asp Asn Ser Asn Asn Thr Leu
65                  70                  75                  80

Tyr Leu Gln Met Ser Ser Leu Arg Ala Glu Asp Thr Ala Phe Tyr Tyr
                85                  90                  95

Cys Ala Arg Met Pro Leu Asn Ser Pro His Asp Cys Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380
```

```
Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 35
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Ala Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Thr Tyr
            20                  25                  30

Tyr Leu Ala Trp Tyr Gln Gln Lys Pro Gly Gln Ala Pro Arg Leu Leu
        35                  40                  45

Ile Tyr Gly Ala Ser Tyr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly His Ser Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 37
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Ser Leu
                85                  90                  95

Thr Phe Gly Gly Gly Thr Lys Val Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 38
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Thr Tyr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Asn Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 39
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaggtgcagc tgctggaaag cggcggaggc ctggtgcaga gaggaggaag cctgagaccc    60
```

| | | |
|---|---|---|
| agctgtgccg ccagcggctt caccttcagc agctacagca tgagctgggt caggcaggcc | 120 | |
| cctggcaaag gactggagtg ggtgagcgtg attagcggca gcggcggctt caccgattac | 180 | |
| gccgacagcg tgaagggcag gttcaccatc agcagggaca atagcaagaa cacccctgtac | 240 | |
| ctgcacatga acagcctgag ggccgaggac accgccgtgt actactgcgc caggatgccc | 300 | |
| ctgaacagcc ctcacgacta ctggggccag ggaaccctgg tgaccgtgtc cagc | 354 | |

<210> SEQ ID NO 40
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

| | | |
|---|---|---|
| caggtgcagc tggtgcagag cggcgcggaa gtgaaaaaac cgggcagcag cgtgaaagtg | 60 | |
| agctgcaaag cgagcggcgg caccttcagc tcctattaca ttagctgggt gcgccaggcg | 120 | |
| ccgggccagg gcctggaatg gatgggtggc attatcccaa tcagtgggcg tgctaattat | 180 | |
| gcgcagaaat ttcagggccg cgtgaccatt accgctgatg aaagcaccag caccgcgtat | 240 | |
| atggaactga gcagcctgcg cagcgaagat accgcggtgt attattgcgc gcgcgacggc | 300 | |
| tacagtagtg gacgtagcac aacatacgca tttgactatt ggggccaggg caccctggtg | 360 | |
| accgtgtcga gt | 372 | |

<210> SEQ ID NO 41
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

| | | |
|---|---|---|
| gaagtgcagc tgctggagag cggaggagga ctggtgcagc ctcctggcgg aagcctgaga | 60 | |
| ctgagctgcg ccgctagcgg cttcaccttc agcagctaca gcatgagctg ggtgagacag | 120 | |
| gctcctggca agggcctgga gtgggtgagc gtgatcagcg gcggaggcag ctttaccagc | 180 | |
| tacgccgaca gcgtgaaggg caggttcacc atcagcaggg acaacagcaa caaccccctg | 240 | |
| tacctgcaga tgagcagcct gagggccgag gacaccgcct ctactactg cgccaggatg | 300 | |
| cccctgaaca gccccatga ctgctgggga cagggcaccc tggtgaccgt gagcagc | 357 | |

<210> SEQ ID NO 42
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

| | | |
|---|---|---|
| gccatccaga tgacccagag ccctagcagc ctgagcgcta gcgtgggcga cagggtgacc | 60 | |
| atcacctgca gggccagcca gggcatcaga acgacctgg gctggtacca gcagaagccc | 120 | |
| ggcaaggccc ccaagctgct gatctacgcc gccagcagcc tgcagagcgg agtgcctagc | 180 | |
| aggttcagcg gaagcggcag cggcaccgac ttcaccctga ccatcagcag cctgcagccc | 240 | |
| gaggacttcg ccacctacta ctgcctgcag gactacaact acgccctgac attcggcggc | 300 | |

```
ggcaccaagg tggagatcaa g                                              321
```

```
<210> SEQ ID NO 43
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gaaattgtgc tgacccagag cccgggcacc ctgagcctga gcccgggcga acgcgcgacc    60
ctgagctgcc gcgcgagcca gagcgtttcc acatactacc tggcgtggta tcagcagaaa   120
ccgggccagg cgccgcgcct gctgatttac ggtgcctcct atcgcgcgac cggcattccg   180
gatcgcttta gcggcagcgg ttccggcacc gattttaccc tgaccattag ccgcctggaa   240
ccggaagatt ttgcggtgta ttattgccag cagtacggtc acagcccgat tacttttggc   300
cagggcacca aagtggaaat caaa                                           324
```

```
<210> SEQ ID NO 44
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gccatccaga tgacccagag ccctagcagc ctgagcgcta gcgtgggcga cagggtgacc    60
atcacctgca gggccagcca gggcatcagg aacgacctgg gctggtacca gcagaagccc   120
ggcaaggccc ccaagctgct gatctacgcc gccagcagcc tgcagagcgg agtgcctagc   180
aggttcagcg gcagcggaag cggcaccgac ttcaccctga ccatctccag cctgcagccc   240
gaggacttcg ccacctacta ctgcctgcag gactacaact acagcctgac cttcggcggc   300
ggcaccaagg tggagatcag g                                              321
```

```
<210> SEQ ID NO 45
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gaaattgtgc tgacccagag cccgggcacc ctgagcctga gcccgggcga acgcgcgacc    60
ctgagctgcc gcgcgagcca gagcgttgcc acctattatc ttgcgtggta tcagcagaaa   120
ccgggccagg cgccgcgcct gctgatttac ggtgcatcct cccgtgcgac cggcattccg   180
gatcgcttta gcggcagcgg ttccggcacc gattttaccc tgaccattag ccgcctggaa   240
ccggaagatt ttgcggtgta ttattgccag cagtacggct ataacccaat tacctttggc   300
cagggcacca aagtggaaat caaa                                           324
```

```
<210> SEQ ID NO 46
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 46

```
gaggtgcagc tgctggaaag cggcggaggc ctggtgcaga gaggaggaag cctgagaccc      60
agctgtgccg ccagcggctt caccttcagc agctacagca tgagctgggt caggcaggcc     120
cctggcaaag gactggagtg ggtgagcgtg attagcggca gcggcggctt caccgattac     180
gccgacagcg tgaagggcag gttcaccatc agcagggaca atagcaagaa cacctgtac      240
ctgcacatga acagcctgag ggccgaggac accgccgtgt actactgcgc caggatgccc     300
ctgaacagcc ctcacgacta ctggggccag ggaaccctgg tgaccgtgtc cagcgcttcc     360
accaagggcc catccgtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacgaa  acctacacc      600
tgcaacgtag atcacaagcc cagcaacacc aaggtggaca gagagttga  gtccaaatat     660
ggtccccat gcccaccatg cccagcacct gaggccgccg gggaccatc  agtcttcctg     720
ttcccccaa  acccaagga  cactctcatg atctcccgga cccctgaggt cacgtgcgtg     780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaa                                                     1335
```

<210> SEQ ID NO 47
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
caggtgcagc tggtgcagag cggcgcggaa gtgaaaaaac cgggcagcag cgtgaaagtg      60
agctgcaaag cgagcggcgg caccttcagc tcctattaca ttagctgggt gcgccaggcg     120
ccgggccagg gcctggaatg gatgggtggc attatcccaa tcagtgggcg tgctaattat     180
gcgcagaaat tcagggccg  cgtgaccatt accgctgatg aaagcaccag caccgcgtat     240
atggaactga gcagcctgcg cagcgaagat accgcggtgt attattgcgc gcgcgacggc     300
tacagtagtg gacgtagcac aacatacgca tttgactatt ggggccaggg caccctggtg     360
accgtgtcga gtgcttccac caagggccca tccgtcttcc ccctggcgcc ctgctccagg     420
agcacctccg agagcacagc cgccctgggc tgcctggtca aggactactt ccccgaaccg     480
gtgacggtgt cgtggaactc aggcgccctg accagcggcg tgcacacctt cccggctgtc     540
ctacagtcct caggactcta ctccctcagc agcgtggtga ccgtgccctc cagcagcttg     600
```

```
ggcacgaaaa cctacacctg caacgtagat cacaagccca gcaacaccaa ggtggacaag      660
agagttgagt ccaaatatgg tcccccatgc ccaccatgcc cagcacctga ggccgccggg      720
ggaccatcag tcttcctgtt cccccaaaa cccaaggaca ctctcatgat ctcccggacc       780
cctgaggtca cgtgcgtggt ggtggacgtg agccaggaag accccgaggt ccagttcaac      840
tggtacgtgg atggcgtgga ggtgcataat gccaagacaa agccgcggga ggagcagttc      900
aacagcacgt accgtgtggt cagcgtcctc accgtcctgc accaggactg gctgaacggc      960
aaggagtaca agtgcaaggt ctccaacaaa ggcctcccgt cctccatcga gaaaaccatc     1020
tccaaagcca aagggcagcc ccgagagcca caggtgtaca ccctgccccc atcccaggag     1080
gagatgacca agaaccaggt cagcctgacc tgcctggtca aaggcttcta ccccagcgac     1140
atcgccgtgg agtgggagag caatgggcag ccggagaaca actacaagac cacgcctccc     1200
gtgctggact ccgacggctc cttcttcctc tacagcaggc taaccgtgga caagagcagg     1260
tggcaggagg ggaatgtctt ctcatgctcc gtgatgcatg aggctctgca caaccactac     1320
acacagaaga gcctctccct gtctctgggt aaa                                  1353
```

<210> SEQ ID NO 48
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
gaagtgcagc tgctggagag cggaggagga ctggtgcagc ctcctggcgg aagcctgaga       60
ctgagctgcg ccgctagcgg cttcaccttc agcagctaca gcatgagctg ggtgagacag      120
gctcctggca agggcctgga gtgggtgagc gtgatcagcg gcggaggcag ctttaccagc      180
tacgccgaca gcgtgaaggg caggttcacc atcagcaggg acaacagcaa caacaccctg      240
tacctgcaga tgagcagcct gagggccgag gacaccgcct tctactactg cgccaggatg      300
cccctgaaca gcccccatga ctgctgggga caggcaccc tggtgaccgt gagcagcgct       360
tccaccaagg gcccatccgt cttccccctg gcgccctgct ccaggagcac ctccgagagc      420
acagccgccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac gaaaacctac      600
acctgcaacg tagatcacaa gcccagcaac accaaggtgg acaagagagt tgagtccaaa      660
tatggtcccc catgcccacc atgcccagca cctgaggccg ccgggggacc atcagtcttc      720
ctgttccccc caaaacccaa ggacactctc atgatctccc ggacccctga ggtcacgtgc      780
gtggtggtgg acgtgagcca ggaagacccc gaggtccagt tcaactggta cgtggatggc      840
gtggaggtgc ataatgccaa gacaaagccg cgggaggagc agttcaacag cacgtaccgt      900
gtggtcagcg tcctcaccgt cctgcaccag gactggctga acggcaagga gtacaagtgc      960
aaggtctcca acaaaggcct cccgtcctcc atcgagaaaa ccatctccaa agccaaaggg     1020
cagccccgag agccacaggt gtacaccctg cccccatccc aggaggagat gaccaagaac     1080
caggtcagcc tgacctgcct ggtcaaaggc ttctacccca gcgacatcgc cgtggagtgg     1140
gagagcaatg gcagccgga gaacaactac aagaccacgc ctcccgtgct ggactccgac     1200
ggctccttct tcctctacag caggctaacc gtggacaaga gcaggtggca ggaggggaat     1260
```

-continued

```
gtcttctcat gctccgtgat gcatgaggct ctgcacaacc actacacaca gaagagcctc      1320
tccctgtctc tgggtaaa                                                    1338
```

<210> SEQ ID NO 49
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
gccatccaga tgacccagag ccctagcagc ctgagcgcta gcgtgggcga cagggtgacc        60
atcacctgca gggccagcca gggcatcaga aacgacctgg gctggtacca gcagaagccc       120
ggcaaggccc ccaagctgct gatctacgcc gccagcagcc tgcagagcgg agtgcctagc       180
aggttcagcg gaagcggcag cggcaccgac ttcaccctga ccatcagcag cctgcagccc       240
gaggacttcg ccacctacta ctgcctgcag gactacaact acgccctgac attcggcggc       300
ggcaccaagg tggagatcaa gcgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gt                         642
```

<210> SEQ ID NO 50
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
gaaattgtgc tgacccagag cccgggcacc ctgagcctga gcccgggcga acgcgcgacc        60
ctgagctgcc gcgcgagcca gagcgtttcc acatactacc tggcgtggta tcagcagaaa       120
ccgggccagg cgccgcgcct gctgatttac ggtgcctcct atcgcgcgac cggcattccg       180
gatcgcttta gcggcagcgg ttccggcacc gattttaccc tgaccattag ccgcctggaa       240
ccggaagatt ttgcggtgta ttattgccag cagtacggtc acagcccgat tacttttggc       300
cagggcacca agtggaaat caaacgtacg gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca aagcagacta cgagaaacac aaagtctacg cctgcgaagt cacccatcag       600
ggcctgagct cgcccgtcac aaagagcttc aacaggggag agtgt                      645
```

<210> SEQ ID NO 51
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
gccatccaga tgacccagag ccctagcagc ctgagcgcta cgtgggcga cagggtgacc      60
atcacctgca gggccagcca gggcatcagg aacgacctgg gctggtacca gcagaagccc     120
ggcaaggccc ccaagctgct gatctacgcc gccagcagcc tgcagagcgg agtgcctagc     180
aggttcagcg gcagcggaag cggcaccgac ttcaccctga ccatctccag cctgcagccc     240
gaggacttcg ccacctacta ctgcctgcag gactacaact acagcctgac cttcggcggc     300
ggcaccaagg tggagatcag cgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg ataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc     600
ctgagctcgc ccgtcacaaa gagcttcaac aggggagagt gt                       642
```

<210> SEQ ID NO 52
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
gaaattgtgc tgacccagag cccgggcacc ctgagcctga gcccgggcga acgcgcgacc     60
ctgagctgcc gcgcgagcca gagcgttgcc acctattatc ttgcgtggta tcagcagaaa    120
ccgggccagg cgccgcgcct gctgatttac ggtgcatcct cccgtgcgac cggcattccg    180
gatcgcttta gcggcagcgg ttccggcacc gattttaccc tgaccattag ccgcctggaa    240
ccggaagatt ttgcggtgta ttattgccag cagtacggct ataacccaat tacctttggc    300
cagggcacca agtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 53
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Gly Gln Gly Thr Leu Val Thr Val Ser Ser
            100                 105
```

<210> SEQ ID NO 54
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg
```

<210> SEQ ID NO 55
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro
                 85                  90                  95
```

<210> SEQ ID NO 56
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 57
<211> LENGTH: 15
<212> TYPE: PRT
<213> ORGANISM: Homo sapiens

<400> SEQUENCE: 57

His Gly Lys Cys Glu His Ser Ile Asn Met Gln Glu Pro Ser Cys
1               5                   10                  15

<210> SEQ ID NO 58
<211> LENGTH: 17
<212> TYPE: PRT
<213> ORGANISM: Homo sapiens

<400> SEQUENCE: 58

Asp Ala Gly Tyr Thr Gly Gln His Cys Glu Lys Lys Asp Tyr Ser Val
1               5                   10                  15

Leu

<210> SEQ ID NO 59
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Phe Asn Asn
            20                  25                  30

Asn Ala Ala Trp Ser Trp Ile Arg Gln Ser Pro Ser Arg Gly Leu Glu
        35                  40                  45

Trp Leu Gly Arg Thr Tyr Tyr Arg Ser Lys Trp Leu Tyr Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Tyr Ser Ser Ser Phe Asp Tyr Trp Gly Gln
            100                 105                 110

Gly Thr Leu Val Thr Val Ser Ser
        115                 120
```

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Tyr Ala Met Asn
1               5

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ile Arg Ser Lys Tyr Asn Asn Tyr Ala Thr Tyr Tyr Ala Ala Ser
1               5                   10                  15

Val Lys Gly

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Gly Asn Phe Gly Asn Ser Tyr Val Ser Trp Phe Ala Tyr
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser Ser Thr Gly Ala Val Thr Thr Ser Asn Tyr Ala Asn
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Thr Asn Lys Arg Ala Pro
1               5

<210> SEQ ID NO 65
<211> LENGTH: 9
<212> TYPE: PRT
<213> ORGANISM: Artificial Sequence
<220> FEATURE:

<223> OTHER INFORMATION: Description of Artificial Sequence: Synthetic
    peptide

<400> SEQUENCE: 65

Ala Leu Trp Tyr Ser Asn Leu Trp Val
1               5

<210> SEQ ID NO 66
<211> LENGTH: 125
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 67

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 68
<211> LENGTH: 7
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 68

Asn Asn Asn Ala Ala Trp Ser
1               5

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Thr Tyr Tyr Arg Ser Lys Trp Leu Tyr Asp Tyr Ala Val Ser Val
1               5                   10                  15

Lys Ser

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Tyr Ser Ser Ser Phe Asp Tyr
1               5

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Gly Thr Ser Ser Asn Ile Gly Thr Tyr Lys Phe Val Ser
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Val Ser Lys Arg Pro Ser
1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Val Ser Tyr Ala Gly Ser Gly Thr Leu Leu
1               5                   10
```

<210> SEQ ID NO 74
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Gln Val Gln Leu Gln Gln Ser Gly Pro Arg Leu Val Arg Pro Ser Gln
1               5                   10                  15

Thr Leu Ser Leu Thr Cys Ala Ile Ser Gly Asp Ser Val Phe Asn Asn
            20                  25                  30

Asn Ala Ala Trp Ser Trp Ile Arg Gln Ser Pro Ser Arg Gly Leu Glu
        35                  40                  45

Trp Leu Gly Arg Thr Tyr Tyr Arg Ser Lys Trp Leu Tyr Asp Tyr Ala
    50                  55                  60

Val Ser Val Lys Ser Arg Ile Thr Val Asn Pro Asp Thr Ser Arg Asn
65                  70                  75                  80

Gln Phe Thr Leu Gln Leu Asn Ser Val Thr Pro Glu Asp Thr Ala Leu
                85                  90                  95

Tyr Tyr Cys Ala Arg Gly Tyr Ser Ser Phe Asp Tyr Trp Gly Gln
            100                 105                 110

Gly Thr Leu Val Thr Val Ser Ser
        115                 120
```

<210> SEQ ID NO 75
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Ile Gly Thr Tyr
            20                  25                  30

Lys Phe Val Ser Trp Tyr Gln Gln His Pro Asp Lys Ala Pro Lys Val
        35                  40                  45

Leu Leu Tyr Glu Val Ser Lys Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Gln Ala Asp Tyr His Cys Val Ser Tyr Ala Gly Ser
                85                  90                  95

Gly Thr Leu Leu Phe Gly Gly Gly Thr Lys Leu Thr Val Leu
            100                 105                 110
```

<210> SEQ ID NO 76
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415
```

```
Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 77
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 78
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Gln Gln Ser Gly Pro Arg Leu Val Arg Pro Ser Gln
1               5                   10                  15

Thr Leu Ser Leu Thr Cys Ala Ile Ser Gly Asp Ser Val Phe Asn Asn
            20                  25                  30
```

-continued

```
Asn Ala Ala Trp Ser Trp Ile Arg Gln Ser Pro Ser Arg Gly Leu Glu
         35                  40                  45

Trp Leu Gly Arg Thr Tyr Tyr Arg Ser Lys Trp Leu Tyr Asp Tyr Ala
 50                  55                  60

Val Ser Val Lys Ser Arg Ile Thr Val Asn Pro Asp Thr Ser Arg Asn
 65                  70                  75                  80

Gln Phe Thr Leu Gln Leu Asn Ser Val Thr Pro Glu Asp Thr Ala Leu
                 85                  90                  95

Tyr Tyr Cys Ala Arg Gly Tyr Ser Ser Phe Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
         180                 185                 190

Ser Ser Ser Leu Gly Thr Lys Thr Tyr Thr Cys Asn Val Asp His Lys
         195                 200                 205

Pro Ser Asn Thr Lys Val Asp Lys Arg Val Glu Ser Lys Tyr Gly Pro
         210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser Gln Glu Asp Pro Glu
                 260                 265                 270

Val Gln Phe Asn Trp Tyr Val Asp Gly Val Glu Val His Asn Ala Lys
         275                 280                 285

Thr Lys Pro Arg Glu Glu Gln Phe Asn Ser Thr Tyr Arg Val Val Ser
         290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                 325                 330                 335

Ser Lys Ala Lys Gly Gln Pro Arg Glu Pro Gln Val Tyr Thr Leu Pro
                 340                 345                 350

Pro Ser Gln Glu Glu Met Thr Lys Asn Gln Val Ser Leu Thr Cys Leu
         355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Leu Leu Tyr Ser Lys Leu Thr Val Asp Lys Ser Arg
                 405                 410                 415

Trp Gln Glu Gly Asn Val Phe Ser Cys Ser Val Met His Glu Ala Leu
                 420                 425                 430

His Asn His Tyr Thr Gln Lys Ser Leu Ser Leu Ser Leu Gly Lys
         435                 440                 445
```

<210> SEQ ID NO 79
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Ile Gly Thr Tyr
            20                  25                  30

Lys Phe Val Ser Trp Tyr Gln Gln His Pro Asp Lys Ala Pro Lys Val
        35                  40                  45

Leu Leu Tyr Glu Val Ser Lys Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Gln Ala Asp Tyr His Cys Val Ser Tyr Ala Gly Ser
                85                  90                  95

Gly Thr Leu Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 80
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80
gaagtgcagc tggtggaatc tggcggcgga ctggtgcagc ctggcggatc tctgagactg      60
agctgtgccg ccagcggctt caccttcaac acctacgcca tgaactgggt gcgccaggcc     120
cctggcaaag gcctggaatg ggtggcccgg atcagaagca agtacaacaa ttacgccacc     180
tactacgccg cctccgtgaa gggcagattc accatcagcc gggacgacag caagaacagc     240
ctgtacctgc agatgaactc cctgaaaacc gaggacaccg ccgtgtacta ctgcgccaga     300
cacggcaact tcggcaacag ctatgtgtct tggtttgcct actggggcca gggcaccctc     360
gtgaccgtgt catctgcttc caccaagggc ccatccgtct tccccctggc gccctgctcc     420
aggagcacct ccgagagcac agccgccctg ggctgcctgg tcaaggacta cttccccgaa     480

```
ccggtgacgg tgtcgtggaa ctcaggcgcc ctgaccagcg gcgtgcacac cttcccggct      540
gtcctacagt cctcaggact ctactccctc agcagcgtgg tgaccgtgcc ctccagcagc      600
ttgggcacga aaacctacac ctgcaacgta gatcacaagc ccagcaacac caaggtggac      660
aagagagttg agtccaaata tggtccccca tgcccaccat gcccagcacc tgaggccgcc      720
gggggaccat cagtcttcct gttccccca aaacccaagg acactctcat gatctcccgg       780
acccctgagg tcacgtgcgt ggtggtggac gtgagccagg aagaccccga ggtccagttc      840
aactggtacg tggatggcgt ggaggtgcat aatgccaaga caaagccgcg ggaggagcag      900
ttcaacagca cgtaccgtgt ggtcagcgtc ctcaccgtcc tgcaccagga ctggctgaac      960
ggcaaggagt acaagtgcaa ggtctccaac aaaggcctcc cgtcctccat cgagaaaacc     1020
atctccaaag ccaaagggca gccccgagag ccacaggtgt acaccctgcc cccatcccag     1080
gaggagatga ccaagaacca ggtcagcctg acctgcctgg tcaaaggctt ctaccccagc     1140
gacatcgccg tggagtggga gagcaatggg cagccggaga acaactacaa gaccacgcct     1200
cccgtgctgg actccgacgg ctccttcctc ctctacagca agctaaccgt ggacaagagc     1260
aggtggcagg aggggaatgt cttctcatgc tccgtgatgc atgaggctct gcacaaccac     1320
tacacacaga agagcctctc cctgtctctg ggtaaa                               1356
```

<210> SEQ ID NO 81
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
cagaccgtcg tgacccagga acctagcctg accgtgtctc ctggcggcac cgtgaccctg       60
acctgcagat cttctacagg cgccgtgacc accagcaact acgccaactg ggtgcagcag      120
aagccaggcc aggctcccag aggactgatc ggcggcacca acaagagagc ccctggcacc      180
cctgccagat tcagcggatc tctgctggga ggaaaggccg ccctgacact gtctggcgtg      240
cagcctgaag atgaggccga gtactactgc gccctgtggt acagcaacct gtgggtgttc      300
ggcggaggca ccaagctgac agtgctgggt cagcccaagg ctgcacccag tgtcactctg      360
ttcccgccct cctctgagga gcttcaagcc aacaaggcca cactggtgtg tctcataagt      420
gacttctacc cgggagccgt gacagtggcc tggaaggccg atagcagccc cgtcaaggcg      480
ggagtggaga ccaccacacc ctccaaacaa agcaacaaca gtacgcggc cagcagctat       540 ctgagcctga cgcctgagca gtggaagtcc cacagaagct acagctgcca ggtcacgcat      600
gaagggagca ccgtggagaa gacagtggcc cctacagaat gttca                     645
```

<210> SEQ ID NO 82
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
caggtgcagc tgcagcagtc tggccctaga ctcgtgcggc cttcccagac cctgtctctg       60
acctgtgcca tctccggcga ctccgtgttc aacaacaacg ccgcctggtc ctggatccgg      120
```

```
cagagccctt ctagaggcct ggaatggctg ggccggacct actaccggtc caagtggctg      180
tacgactacg ccgtgtccgt gaagtcccgg atcaccgtga accctgacac ctcccggaac      240
cagttcaccc tgcagctgaa ctccgtgacc cctgaggaca ccgccctgta ctactgcgcc      300
agaggctact cctcctcctt cgactattgg ggccagggca ccctcgtgac cgtgtcctct      360
gcttccacca agggcccatc cgtcttcccc ctggcgccct gctccaggag cacctccgag      420
agcacagccg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacgaaaacc      600
tacacctgca acgtagatca caagcccagc aacaccaagg tggacaagag agttgagtcc      660
aaatatggtc ccccatgccc accatgccca gcacctgagg ccgccggggg accatcagtc      720
ttcctgttcc ccccaaaacc caaggacact ctcatgatct cccggacccc tgaggtcacg      780
tgcgtggtgg tggacgtgag ccaggaagac cccgaggtcc agttcaactg gtacgtggat      840
ggcgtggagg tgcataatgc caagacaaag ccgcgggagg agcagttcaa cagcacgtac      900
cgtgtggtca gcgtcctcac cgtcctgcac caggactggc tgaacggcaa ggagtacaag      960
tgcaaggtct ccaacaaagg cctcccgtcc tccatcgaga aaaccatctc caaagccaaa     1020
gggcagcccc gagagccaca ggtgtacacc ctgcccccat cccaggagga tgaccaag      1080 aaccaggtca gcctgacctg cctggtcaaa ggcttctacc ccagcgacat cgccgtggag     1140
tgggagagca atgggcagcc ggagaacaac tacaagacca cgcctcccgt gctggactcc     1200
gacggctcct tcttcctcta cagcaagcta accgtggaca agagcaggtg gcaggagggg     1260
aatgtcttct catgctccgt gatgcatgag gctctgcaca accactacac acagaagagc     1320 ctctcccctgt ctctgggtaa a                                              1341
```

<210> SEQ ID NO 83
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
cagtctgctc tgacccagcc tgcctccgtg tctggctctc ccggccagtc catcaccatc       60
agctgtaccg gcacctcctc caacatcggc acctacaagt tcgtgtcctg gtatcagcag      120
caccccgaca ggcccccaa agtgctgctg tacgaggtgt ccaagcggcc ctctggcgtg      180
tcctccagat ctccggctc caagtctggc aacaccgcct ccctgaccat cagcggactg      240
caggctgagg accaggccga ctaccactgt gtgtcctacg ctggctctgg caccctgctg      300
tttggcggag gcaccaagct gaccgtgctg ggtcagccca aggctgcacc cagtgtcact      360
ctgttcccgc cctcctctga ggagcttcaa gccaacaagg ccacactggt gtgtctcata      420
agtgacttct acccgggagc cgtgacagtg gcctggaagg ccgatagcag ccccgtcaag      480
gcgggagtgg agaccaccac accctccaaa caaagcaaca caagtacgc ggccagcagc      540 tatctgagcc tgacgcctga gcagtggaag tcccacagaa gctacagctg ccaggtcacg      600
catgaaggga gcaccgtgga agacagtg ccccctacag aatgttca                    648
```

<210> SEQ ID NO 84
<211> LENGTH: 330
<212> TYPE: PRT

```
<213> ORGANISM: Unknown
<220> FEATURE:
<223> OTHER INFORMATION: Description of Unknown:
      wild-type IgG1 sequence

<400> SEQUENCE: 84
```

| | | | | | | | | | | | | | | | |
|---|---|---|---|---|---|---|---|---|---|---|---|---|---|---|---|
|Ala|Ser|Thr|Lys|Gly|Pro|Ser|Val|Phe|Pro|Leu|Ala|Pro|Ser|Ser|Lys|
|1| | | |5| | | | |10| | | | |15| |

| | | | | | | | | | | | | | |
|---|---|---|---|---|---|---|---|---|---|---|---|---|---|
|Ser|Thr|Ser|Gly|Gly|Thr|Ala|Ala|Leu|Gly|Cys|Leu|Val|Lys|Asp|Tyr|
| | | | |20| | | | |25| | | | |30| |

|Phe|Pro|Glu|Pro|Val|Thr|Val|Ser|Trp|Asn|Ser|Gly|Ala|Leu|Thr|Ser|
| | | | |35| | | | |40| | | | |45| |

|Gly|Val|His|Thr|Phe|Pro|Ala|Val|Leu|Gln|Ser|Ser|Gly|Leu|Tyr|Ser|
|50| | | | |55| | | | |60| | | | | |

|Leu|Ser|Ser|Val|Val|Thr|Val|Pro|Ser|Ser|Ser|Leu|Gly|Thr|Gln|Thr|
|65| | | | |70| | | | |75| | | | |80|

|Tyr|Ile|Cys|Asn|Val|Asn|His|Lys|Pro|Ser|Asn|Thr|Lys|Val|Asp|Lys|
| | | | |85| | | | |90| | | | |95| |

|Lys|Val|Glu|Pro|Lys|Ser|Cys|Asp|Lys|Thr|His|Thr|Cys|Pro|Pro|Cys|
| | | | |100| | | | |105| | | | |110| |

|Pro|Ala|Pro|Glu|Leu|Leu|Gly|Gly|Pro|Ser|Val|Phe|Leu|Phe|Pro|Pro|
| | | | |115| | | | |120| | | | |125| |

|Lys|Pro|Lys|Asp|Thr|Leu|Met|Ile|Ser|Arg|Thr|Pro|Glu|Val|Thr|Cys|
|130| | | | |135| | | | |140| | | | | |

|Val|Val|Val|Asp|Val|Ser|His|Glu|Asp|Pro|Glu|Val|Lys|Phe|Asn|Trp|
|145| | | | |150| | | | |155| | | | |160|

|Tyr|Val|Asp|Gly|Val|Glu|Val|His|Asn|Ala|Lys|Thr|Lys|Pro|Arg|Glu|
| | | | |165| | | | |170| | | | |175| |

|Glu|Gln|Tyr|Asn|Ser|Thr|Tyr|Arg|Val|Val|Ser|Val|Leu|Thr|Val|Leu|
| | | | |180| | | | |185| | | | |190| |

|His|Gln|Asp|Trp|Leu|Asn|Gly|Lys|Glu|Tyr|Lys|Cys|Lys|Val|Ser|Asn|
| | | | |195| | | | |200| | | | |205| |

|Lys|Ala|Leu|Pro|Ala|Pro|Ile|Glu|Lys|Thr|Ile|Ser|Lys|Ala|Lys|Gly|
| | | | |210| | | | |215| | | | |220| |

|Gln|Pro|Arg|Glu|Pro|Gln|Val|Tyr|Thr|Leu|Pro|Pro|Ser|Arg|Asp|Glu|
|225| | | | |230| | | | |235| | | | |240|

|Leu|Thr|Lys|Asn|Gln|Val|Ser|Leu|Thr|Cys|Leu|Val|Lys|Gly|Phe|Tyr|
| | | | |245| | | | |250| | | | |255| |

|Pro|Ser|Asp|Ile|Ala|Val|Glu|Trp|Glu|Ser|Asn|Gly|Gln|Pro|Glu|Asn|
| | | | |260| | | | |265| | | | |270| |

|Asn|Tyr|Lys|Thr|Thr|Pro|Pro|Val|Leu|Asp|Ser|Asp|Gly|Ser|Phe|Phe|
| | | | |275| | | | |280| | | | |285| |

|Leu|Tyr|Ser|Lys|Leu|Thr|Val|Asp|Lys|Ser|Arg|Trp|Gln|Gln|Gly|Asn|
|290| | | | |295| | | | |300| | | | | |

|Val|Phe|Ser|Cys|Ser|Val|Met|His|Glu|Ala|Leu|His|Asn|His|Tyr|Thr|
|305| | | | |310| | | | |315| | | | |320|

|Gln|Lys|Ser|Leu|Ser|Leu|Ser|Pro|Gly|Lys| | | | | | |
| | | | |325| | | | |330| | | | | | |

```
<210> SEQ ID NO 85
<211> LENGTH: 327
<212> TYPE: PRT
<213> ORGANISM: Unknown
<220> FEATURE:
<223> OTHER INFORMATION: Description of Unknown:
      wild-type IgG4 sequence
```

<400> SEQUENCE: 85

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Gln Asp Tyr Asn Tyr Pro Leu Thr
1               5

```
<210> SEQ ID NO 87
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Val Ile Ser Gly Ser Gly Gly Phe Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Pro Leu Asn Ser Pro His Asp Tyr Trp Gly Gln Gly Thr
            100                 105                 110

Leu Val Thr Val Ser Ser
        115

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys
            100                 105

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Leu Glu Ser Gly Gly Gly Leu Val Gln Pro Gly Gly
```

```
                1               5                  10                 15
Ser Leu Arg Leu Ser Cys Ala Ala Ser Gly Phe Thr Phe Ser Ser Tyr
                20                 25                 30

Ser Met Ser Trp Val Arg Gln Ala Pro Gly Lys Gly Leu Glu Trp Val
                35                 40                 45

Ser Val Ile Ser Gly Ser Gly Gly Phe Thr Asp Tyr Ala Asp Ser Val
                50                 55                 60

Lys Gly Arg Phe Thr Ile Ser Arg Asp Asn Ser Lys Asn Thr Leu Tyr
 65                 70                 75                 80

Leu His Met Asn Ser Leu Arg Ala Glu Asp Thr Ala Val Tyr Tyr Cys
                85                 90                 95

Ala Arg Met Pro Leu Asn Ser Pro His Asp Tyr Trp Gly Gln Gly Thr
                100                105                110

Leu Val Thr Val Ser Ser
                115
```

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Ala Ile Gln Met Thr Gln Ser Pro Ser Ser Leu Ser Ala Ser Val Gly
 1               5                  10                 15

Asp Arg Val Thr Ile Thr Cys Arg Ala Ser Gln Gly Ile Arg Asn Asp
                20                 25                 30

Leu Gly Trp Tyr Gln Gln Lys Pro Gly Lys Ala Pro Lys Leu Leu Ile
                35                 40                 45

Tyr Ala Ala Ser Ser Leu Gln Ser Gly Val Pro Ser Arg Phe Ser Gly
                50                 55                 60

Ser Gly Ser Gly Thr Asp Phe Thr Leu Thr Ile Ser Ser Leu Gln Pro
 65                 70                 75                 80

Glu Asp Phe Ala Thr Tyr Tyr Cys Leu Gln Asp Tyr Asn Tyr Pro Leu
                85                 90                 95

Thr Phe Gly Gly Gly Thr Lys Val Glu Ile Lys
                100                105
```

<210> SEQ ID NO 91
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Ser Ser Tyr
                20                 25                 30

Ser Met Ser Trp Val Arg Gln Ala Pro Gly Lys Gly Leu Glu Trp Val
                35                 40                 45

Ser Val Ile Ser Gly Ser Gly Gly Phe Thr Asp Tyr Ala Asp Ser Val
                50                 55                 60

Lys Gly Arg Phe Thr Ile Ser Arg Asp Asn Ser Lys Asn Thr Leu Tyr
```

Leu Gln Met Asn Ser Leu Arg Ala Glu Asp Thr Ala Val Tyr Tyr Cys
65                  70                  75                  80

Ala Arg Met Pro Leu Asn Ser Pro His Asp Tyr Trp Gly Gln Gly Thr
                85                  90                  95

Leu Val Thr Val Ser Ser Ala Ser Thr Lys Gly Pro Ser Val Phe Pro
            100                 105                 110

Leu Ala Pro Cys Ser Arg Ser Thr Ser Glu Ser Thr Ala Ala Leu Gly
        115                 120                 125

Cys Leu Val Lys Asp Tyr Phe Pro Glu Pro Val Thr Val Ser Trp Asn
130                 135                 140

Ser Gly Ala Leu Thr Ser Gly Val His Thr Phe Pro Ala Val Leu Gln
145                 150                 155                 160

Ser Ser Gly Leu Tyr Ser Leu Ser Ser Val Val Thr Val Pro Ser Ser
                165                 170                 175

Ser Leu Gly Thr Lys Thr Tyr Thr Cys Asn Val Asp His Lys Pro Ser
            180                 185                 190

Asn Thr Lys Val Asp Lys Arg Val Glu Ser Lys Tyr Gly Pro Pro Cys
        195                 200                 205

Pro Pro Cys Pro Ala Pro Glu Ala Ala Gly Gly Pro Ser Val Phe Leu
210                 215                 220

Phe Pro Pro Lys Pro Lys Asp Thr Leu Met Ile Ser Arg Thr Pro Glu
225                 230                 235                 240

Val Thr Cys Val Val Val Asp Val Ser Gln Glu Asp Pro Glu Val Gln
                245                 250                 255

Phe Asn Trp Tyr Val Asp Gly Val Glu Val His Asn Ala Lys Thr Lys
            260                 265                 270

Pro Arg Glu Glu Gln Phe Asn Ser Thr Tyr Arg Val Val Ser Val Leu
        275                 280                 285

Thr Val Leu His Gln Asp Trp Leu Asn Gly Lys Glu Tyr Lys Cys Lys
290                 295                 300

Val Ser Asn Lys Gly Leu Pro Ser Ser Ile Glu Lys Thr Ile Ser Lys
305                 310                 315                 320

Ala Lys Gly Gln Pro Arg Glu Pro Gln Val Tyr Thr Leu Pro Pro Ser
                325                 330                 335

Gln Glu Glu Met Thr Lys Asn Gln Val Ser Leu Thr Cys Leu Val Lys
            340                 345                 350

Gly Phe Tyr Pro Ser Asp Ile Ala Val Glu Trp Glu Ser Asn Gly Gln
        355                 360                 365

Pro Glu Asn Asn Tyr Lys Thr Thr Pro Pro Val Leu Asp Ser Asp Gly
370                 375                 380

Ser Phe Phe Leu Tyr Ser Arg Leu Thr Val Asp Lys Ser Arg Trp Gln
385                 390                 395                 400

Glu Gly Asn Val Phe Ser Cys Ser Val Met His Glu Ala Leu His Asn
                405                 410                 415

His Tyr Thr Gln Lys Ser Leu Ser Leu Ser Leu Gly Lys
            420                 425                 430

435                 440                 445

<210> SEQ ID NO 92
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 92

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 93
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Val Ile Ser Gly Ser Gly Gly Phe Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Arg Met Pro Leu Asn Ser Pro His Asp Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 94
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
```

```
                35                  40                  45
Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 95
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gaggtgcagc tgctggaaag cggcggaggc ctggtgcagc ccggaggaag cctgagactc        60
agctgtgccg ccagcggctt caccttcagc agctacagca tgagctgggt caggcaggcc       120
cctggcaaag gactggagtg ggtgagcgtg attagcggca gcggcggctt caccgattac       180
gccgacagcg tgaagggcag gttcaccatc agcagggaca tagcaagaa cacccctgtac       240 ctgcagatga acagcctgag ggccgaggac accgccgtgt actactgcgc caggatgccc       300
ctgaacagcc tcacgactac tggggccag ggaaccctgg tgaccgtgtc cagc              354

<210> SEQ ID NO 96
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gacatccaga tgacccagag ccctagcagc ctgagcgcta gcgtgggcga cagggtgacc        60
atcacctgca gggccagcca gggcatcaga aacgacctgg ctggtacca gcagaagccc       120 ggcaaggccc ccaagctgct gatctacgcc gccagcagcc tgcagagcgg agtgcctagc       180
aggttcagcg gaagcggcag cggcaccgac ttcaccctga ccatcagcag cctgcagccc       240
gaggacttcg ccacctacta ctgcctgcag gactacaact accccctgac attcggcggc       300
```
ggcaccaagg tggagatcaa g                                             321

<210> SEQ ID NO 97
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gaggtgcagc tgctggaaag cggcggaggc ctggtgcagc ccggaggaag cctgagactc        60
agctgtgccg ccagcggctt caccttcagc agctacagca tgagctgggt caggcaggcc       120
cctggcaaag gactggagtg ggtgagcgtg attagcggca gcggcggctt caccgattac       180
gccgacagcg tgaagggcag gttcaccatc agcagggaca tagcaagaa caccctgtac        240 ctgcagatga acagcctgag ggccgaggac accgccgtgt actactgcgc caggatgccc       300
ctgaacagcc ctcacgacta ctggggccag ggaaccctgg tgaccgtgtc cagcgcttcc       360
accaagggcc catccgtctt ccccctggcg ccctgctcca ggagcacctc cgagagcaca       420
gccgccctgg gctgcctggt caaggactac ttccccgaac cggtgacggt gtcgtggaac       480
tcaggcgccc tgaccagcgg cgtgcacacc ttcccggctg tcctacagtc ctcaggactc       540
tactccctca gcagcgtggt gaccgtgccc tccagcagct gggcacgaa aacctacact        600 tgcaacgtag atcacaagcc cagcaacacc aaggtggaca agagagttga gtccaaatat       660
ggtcccccat gcccaccatg cccagcacct gaggccgccg ggggaccatc agtcttcctg       720
ttccccccaa aacccaagga cactctcatg atctcccgga cccctgaggt cacgtgcgtg       780
gtggtggacg tgagccagga agacccgag gtccagttca actggtacgt ggatggcgtg       840
gaggtgcata atgccaagac aaagccgcgg gaggagcagt tcaacagcac gtaccgtgtg       900
gtcagcgtcc tcaccgtcct gcaccaggac tggctgaacg gcaaggagta caagtgcaag       960
gtctccaaca aaggcctccc gtcctccatc gagaaaacca tctccaaagc caaagggcag      1020
ccccgagagc cacaggtgta caccctgccc ccatcccagg aggagatgac caagaaccag      1080
gtcagcctga cctgcctggt caaaggcttc taccccagcg acatcgccgt ggagtgggag      1140
agcaatgggc agccggagaa caactacaag accacgcctc ccgtgctgga ctccgacggc      1200
tccttcttcc tctacagcag gctaaccgtg gacaagagca gatggcagga ggggaatgtc      1260
ttctcatgct ccgtgatgca tgaggctctg cacaaccact acacacagaa gagcctctcc      1320
ctgtctctgg gtaaa                                                      1335

<210> SEQ ID NO 98
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gacatccaga tgacccagag ccctagcagc ctgagcgcta gcgtgggcga cagggtgacc        60
atcacctgca gggccagcca gggcatcaga aacgacctgg gctggtacca gcagaagccc       120
ggcaaggccc ccaagctgct gatctacgcc gccagcagcc tgcagagcgg agtgcctagc       180
aggttcagcg gaagcggcag cggcaccgac ttcaccctga ccatcagcag cctgcagccc       240
gaggacttcg ccacctacta ctgcctgcag gactacaact accccctgac attcggcggc       300

```
ggcaccaagg tggagatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 99
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
gaggtgcagc tgctggaaag cggcggaggc ctggtgcagc ccggaggaag cctgagactc     60
agctgtgccg ccagcggctt caccttcagc agctacagca tgagctgggt caggcaggcc    120
cctggcaaag gactggagtg ggtgagcgtg attagcggag gcggcggctt caccgattac    180
gccgacagcg tgaagggcag gttcaccatc agcagggaca atagcaagaa cacccctgtac   240 ctgcacatga acagcctgag ggccgaggac accgccgtgt actactgcgc caggatgccc    300
ctgaacagcc ctcacgacta ctggggccag ggaaccctgg tgaccgtgtc cagc          354
```

<210> SEQ ID NO 100
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
gccatccaga tgacccagag ccctagcagc ctgagcgcta gcgtgggcga cagggtgacc     60
atcacctgca gggccagcca gggcatcaga aacgacctgg gctggtacca gcagaagccc    120
ggcaaggccc ccaagctgct gatctacgcc gccagcagcc tgcagagcgg agtgcctagc    180
aggttcagcg gaagcggcag cggcaccgac ttcaccctga ccatcagcag cctgcagccc    240
gaggacttcg ccacctacta ctgcctgcag gactacaact accccctgac attcggcggc    300
ggcaccaagg tggagatcaa g                                              321
```

<210> SEQ ID NO 101
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
gaggtgcagc tgctggaaag cggcggaggc ctggtgcagc ccggaggaag cctgagactc     60
agctgtgccg ccagcggctt caccttcagc agctacagca tgagctgggt caggcaggcc    120
cctggcaaag gactggagtg ggtgagcgtg attagcggca gcggcggctt caccgattac    180
gccgacagcg tgaagggcag gttcaccatc agcagggaca atagcaagaa cacccctgtac   240 ctgcacatga acagcctgag ggccgaggac accgccgtgt actactgcgc caggatgccc    300
```

```
ctgaacagcc ctcacgacta ctggggccag ggaaccctgg tgaccgtgtc cagcgcttcc      360
accaagggcc catccgtctt cccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttccggctg tcctacagtc ctcaggactc      540
tactccctca gcagcgtggt gaccgtgccc tccagcagct gggcacgaa aacctacact      600 tgcaacgtag atcacaagcc cagcaacacc aaggtggaca agagagttga gtccaaatat     660
ggtcccccat gcccaccatg cccagcacct gaggccgccg ggggaccatc agtcttcctg     720 ttcccccca aacccaagga cactctcatg atctcccgga cccctgaggt cacgtgcgtg      780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaa                                                     1335
```

<210> SEQ ID NO 102
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
gccatccaga tgacccagag ccctagcagc ctgagcgcta gcgtgggcga cagggtgacc       60
atcacctgca gggccagcca gggcatcaga aacgacctgg gctggtacca gcagaagccc      120
ggcaaggccc ccaagctgct gatctacgcc gccagcagcc tgcagagcgg agtgcctagc      180
aggttcagcg gaagcggcag cggcaccgac ttcaccctga ccatcagcag cctgcagccc      240
gaggacttcg ccacctacta ctgcctgcag gactacaact ccccctgac attcggcggc      300 ggcaccaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct cgaagtcac ccatcagggc      600 ctgagctcgc ccgtcacaaa gagcttcaac aggggagagt gttag                     645
```

<210> SEQ ID NO 103
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 104
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Ser Thr Lys Gly Pro Ser Val Phe Pro Leu Ala Pro Cys Ser Arg
1               5                   10                  15

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
         115                 120                 125

Asp Thr Leu Met Ile Ser Arg Thr Pro Glu Val Thr Cys Val Val Val
     130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                 165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
         195                 200                 205

Pro Ser Ser Ile Glu Lys Thr Ile Ser Lys Ala Lys Gly Gln Pro Arg
     210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                 245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Leu Leu Tyr Ser
         275                 280                 285

Lys Leu Thr Val Asp Lys Ser Arg Trp Gln Glu Gly Asn Val Phe Ser
     290                 295                 300

Cys Ser Val Met His Glu Ala Leu His Asn His Tyr Thr Gln Lys Ser
305                 310                 315                 320

Leu Ser Leu Ser Leu Gly Lys
                 325

<210> SEQ ID NO 105
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gaagtgcagc tggtggaatc tggcggcgga ctggtgcagc ctggcggatc tctgagactg     60
agctgtgccg ccagcggctt caccttcaac acctacgcca tgaactgggt gcgccaggcc    120
cctggcaaag gcctggaatg gtggcccgg atcagaagca agtacaacaa ttacgccacc    180
tactacgccg cctccgtgaa gggcagattc accatcagcc gggacgacag caagaacagc    240
```

```
ctgtacctgc agatgaactc cctgaaaacc gaggacaccg ccgtgtacta ctgcgccaga    300
cacggcaact tcggcaacag ctatgtgtct tggtttgcct actggggcca gggcaccctc    360
gtgaccgtgt catct                                                     375

<210> SEQ ID NO 106
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
cagaccgtcg tgacccagga acctagcctg accgtgtctc ctggcggcac cgtgaccctg     60
acctgcagat cttctacagg cgccgtgacc accagcaact acgccaactg ggtgcagcag    120
aagccaggcc aggctcccag aggactgatc ggcggcacca caagagagc ccctggcacc     180 cctgccagat tcagcggatc tctgctggga ggaaaggccg ccctgacact gtctggcgtg    240
cagcctgaag atgaggccga gtactactgc gccctgtggt acagcaacct gtgggtgttc    300
ggcggaggca ccaagctgac agtgctg                                        327

<210> SEQ ID NO 107
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
caggtgcagc tgcagcagtc tggccctaga ctcgtgcggc cttcccagac cctgtctctg     60
acctgtgcca tctccggcga ctccgtgttc aacaacaacg ccgcctggtc ctggatccgg    120
cagagccctt ctagaggcct ggaatggctg ggccggacct actaccgtc caagtggctg    180 tacgactacg ccgtgtccgt gaagtcccgg atcaccgtga accctgacac ctcccggaac    240
cagttcaccc tgcagctgaa ctccgtgacc cctgaggaca ccgccctgta ctactgcgcc    300
agaggctact cctcctcctt cgactattgg ggccagggca ccctcgtgac cgtgtcctct    360

<210> SEQ ID NO 108
<211> LENGTH: 329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
agtctgctct gacccagcct gcctccgtgt ctggctctcc cggccagtcc atcaccatca     60
gctgtaccgg cacctcctcc aacatcggca cctacaagtt cgtgtcctgg tatcagcagc    120
accccgacaa ggcccccaaa gtgctgctgt acgaggtgtc caagcggccc tctggcgtgt    180
cctccagatt ctccggctcc aagtctggca caccgcctc cctgaccatc agcggactgc    240
aggctgagga ccaggccgac taccactgtg tgtcctacgc tggctctggc accctgctgt    300
ttggcggagg caccaagctg accgtgctg                                      329

<210> SEQ ID NO 109
<211> LENGTH: 330
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 110
<211> LENGTH: 91
<212> TYPE: PRT
<213> ORGANISM: Homo sapiens

<400> SEQUENCE: 110

Asn Thr Thr Thr Thr Thr Lys Ser Glu Asp Gly His Tyr Ala Arg Thr

```
1               5                   10                  15
Asp Tyr Ala Glu Asn Ala Asn Lys Leu Glu Glu Ser Ala Arg Glu His
                20                  25                  30

His Ile Pro Cys Pro Glu His Tyr Asn Gly Phe Cys Met His Gly Lys
            35                  40                  45

Cys Glu His Ser Ile Asn Met Gln Glu Pro Ser Cys Arg Cys Asp Ala
        50                  55                  60

Gly Tyr Thr Gly Gln His Cys Glu Lys Lys Asp Tyr Ser Val Leu Tyr
65                  70                  75                  80

Val Val Pro Gly Pro Val Arg Phe Gln Tyr Val
                85                  90

<210> SEQ ID NO 111
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Ile Gly Thr Tyr
                20                  25                  30

Lys Phe Val Ser Trp Tyr Gln Gln His Pro Gly Lys Ala Pro Lys Val
            35                  40                  45

Met Ile Tyr Glu Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Val Ser Tyr Ala Gly Ser
                85                  90                  95

Gly Thr Leu Leu Phe Gly Gly Gly Thr Lys Leu Thr Val Leu
            100                 105                 110

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 112

His His His His His His
1               5
```